US012758384B2

(12) United States Patent
Quinn

(10) Patent No.: US 12,758,384 B2
(45) **Date of Patent: *Oct. 13, 2026**

(54) HEART VALVE TREATMENT DEVICE AND METHOD

(71) Applicant: THE PROVOST, FELLOWS FOUNDATION SCHOLARS, AND THE OTHER MEMBERS OF THE BOARD, OF THE COLLEGE OF THE HOLY AND UNDIVIDED TRINITY OF QUEEN ELIZABETH NEAR DUBLIN (TCD), Dublin (IE)

(72) Inventor: Martin Quinn, Blackrock (IE)

(73) Assignee: The Provost, Fellows Foundation Scholars, and the other Members of Board, of the College of the Holy and Undivided Trinity of Queen Elizabeth near Dublin (TCD), Dublin (IE)

( * ) Notice: Subject to any disclaimer, the term of this patent is extended or adjusted under 35 U.S.C. 154(b) by 1251 days.

This patent is subject to a terminal disclaimer.

(21) Appl. No.: 17/238,060

(22) Filed: Apr. 22, 2021

(65) Prior Publication Data

US 2021/0259829 A1 Aug. 26, 2021

Related U.S. Application Data

(63) Continuation of application No. 16/900,791, filed on Jun. 12, 2020, now Pat. No. 10,987,220, which is a (Continued)

(30) Foreign Application Priority Data

Sep. 29, 2014 (EP) .................................... 14186930
Oct. 29, 2014 (EP) .................................... 14190855
May 22, 2015 (EP) .................................... 15168947

(51) Int. Cl.
*A61F 2/24* (2006.01)
*A61B 17/04* (2006.01)
*A61B 17/22* (2006.01)

(52) U.S. Cl.
CPC ............ *A61F 2/246* (2013.01); *A61F 2/2412* (2013.01); *A61F 2/2436* (2013.01); (Continued)

(58) Field of Classification Search
CPC ........ A61F 2/24; A61F 2/2454; A61F 2/2463; A61F 2/2445; A61F 2/2418
See application file for complete search history.

(56) References Cited

U.S. PATENT DOCUMENTS 2,684,069 A 7/1954 Shearman et al.
3,689,942 A 9/1972 Rapp
(Continued)

FOREIGN PATENT DOCUMENTS

AU 2016200392 B2 12/2017
CA 2705942 A1 5/2009
(Continued)

OTHER PUBLICATIONS

U.S. Appl. No. 15/514,204 / U.S. Pat. No. 10,383,729, filed Mar. 24, 2017 / Aug. 20, 2019.
U.S. Appl. No. 16/443,792 / U.S. Pat. No. 10,682,231, filed Jun. 17, 2019 / Jun. 16, 2020.
U.S. Appl. No. 16/900,791 / U.S. Pat. No. 10,987,220 filed Jun. 12, 2020 / Nov. 5, 2020.
(Continued)

*Primary Examiner* — Jason-Dennis N Stewart
(74) *Attorney, Agent, or Firm* — Greenberg Traurig, LLP; Christopher C. Bolten; Albert K. Heng

(57) ABSTRACT

A heart valve therapeutic device (1) has an elongate anchor (7) wherein the anchor has a stiffness to hold its shape and location to support the valve element. The anchor may have a stylet or a shaped or stiff collar (70) arranged to provide a desired shape to the anchor (7) and it may be lockable. A prosthetic valve element (15) has leaflets (17) and is sup-
(Continued)

ported on the anchor by coupler (16, 50) at a desired location. There is an actuator for changing relative axial position of the proximal and distal couplers (16, 50) on the anchor. The anchor stiffness may be sufficient to provide sufficient support to resist axial forces from the ventricle in use without necessarily having a fixing element engaging heart tissue. The prosthetic leaflets (240) may extend proximally and radially outwardly, so that there is excellent co-apting of the native leaflets (NL) against the prosthetic leaflets (240).

17 Claims, 56 Drawing Sheets

Related U.S. Application Data continuation of application No. 16/443,792, filed on Jun. 17, 2019, now Pat. No. 10,682,231, which is a continuation of application No. 15/514,204, filed as application No. PCT/EP2015/072388 on Sep. 29, 2015, now Pat. No. 10,383,729.

(52) U.S. Cl.
CPC .......... *A61F 2/2451* (2013.01); *A61F 2/2457* (2013.01); *A61F 2/2466* (2013.01); *A61B 2017/0419* (2013.01); *A61B 2017/044* (2013.01); *A61B 2017/0464* (2013.01); *A61B 2017/22044* (2013.01); *A61B 2017/22047* (2013.01); *A61F 2220/0016* (2013.01); *A61F 2250/006* (2013.01)

(56) References Cited

U.S. PATENT DOCUMENTS

| | | | |
|---|---|---|---|
| 3,746,003 | A | 7/1973 | Blake et al. |
| 5,509,428 | A | 4/1996 | Dunlop |
| 5,792,179 | A | 8/1998 | Sideris |
| 6,168,614 | B1 | 1/2001 | Andersen et al. |
| 6,241,762 | B1 | 6/2001 | Shanley |
| 6,332,893 | B1 | 12/2001 | Mortier et al. |
| 6,425,916 | B1 * | 7/2002 | Garrison ............... A61F 2/2436 623/2.11 |
| 6,461,366 | B1 | 10/2002 | Seguin |
| 6,527,800 | B1 | 3/2003 | McGuckin, Jr. et al. |
| 6,540,782 | B1 | 4/2003 | Snyders |
| 6,582,462 | B1 | 6/2003 | Andersen et al. |
| 6,629,534 | B1 | 10/2003 | St. Goar et al. |
| 6,752,813 | B2 | 6/2004 | Goldfarb et al. |
| 6,755,812 | B2 | 6/2004 | Peterson et al. |
| 6,764,510 | B2 | 7/2004 | Vidlund et al. |
| 6,821,297 | B2 | 11/2004 | Snyders |
| 6,869,414 | B2 | 3/2005 | Simpson et al. |
| 6,893,459 | B1 | 5/2005 | Macoviak |
| 6,955,689 | B2 | 10/2005 | Ryan et al. |
| 7,077,862 | B2 | 7/2006 | Vidlund et al. |
| 7,542,808 | B1 | 6/2009 | Peterson et al. |
| 7,678,145 | B2 | 3/2010 | Vidlund et al. |
| 7,704,277 | B2 | 4/2010 | Zakay et al. |
| 7,785,366 | B2 | 8/2010 | Maurer et al. |
| 7,854,762 | B2 | 12/2010 | Speziali et al. |
| 7,901,454 | B2 | 3/2011 | Kapadia et al. |
| 8,070,805 | B2 | 12/2011 | Vidlund et al. |
| 8,216,302 | B2 | 7/2012 | Wilson et al. |
| 8,216,303 | B2 | 7/2012 | Navia |
| 8,449,606 | B2 | 5/2013 | Eliasen et al. |
| 8,460,370 | B2 | 6/2013 | Zakay et al. |
| 8,470,028 | B2 | 6/2013 | Thornton et al. |
| 8,475,525 | B2 | 7/2013 | Maisano et al. |
| 8,480,730 | B2 | 7/2013 | Maurer et al. |
| 8,486,136 | B2 | 7/2013 | Maurer et al. |
| 8,506,624 | B2 | 8/2013 | Vidlund et al. |
| 8,579,967 | B2 | 11/2013 | Webler et al. |
| 8,758,432 | B2 | 6/2014 | Solem |
| 8,888,844 | B2 | 11/2014 | Eliasen et al. |
| 8,894,705 | B2 | 11/2014 | Eliasen et al. |
| 8,923,973 | B2 | 12/2014 | Gross |
| 8,932,348 | B2 | 1/2015 | Solem et al. |
| 8,961,596 | B2 | 2/2015 | Maisano et al. |
| 8,968,395 | B2 | 3/2015 | Hauser et al. |
| 8,979,922 | B2 | 3/2015 | Jayasinghe et al. |
| 8,992,605 | B2 | 3/2015 | Zakai et al. |
| 9,005,279 | B2 | 4/2015 | Gabbay |
| 9,011,523 | B2 | 4/2015 | Seguin |
| 9,132,007 | B2 | 9/2015 | Menk et al. |
| 9,161,837 | B2 | 10/2015 | Kapadia |
| 9,232,998 | B2 | 1/2016 | Wilson et al. |
| 9,232,999 | B2 | 1/2016 | Maurer et al. |
| 9,289,297 | B2 | 3/2016 | Wilson et al. |
| 9,358,112 | B2 | 6/2016 | Hlavka et al. |
| 9,370,424 | B2 | 6/2016 | Call et al. |
| 9,414,918 | B2 | 8/2016 | Chau et al. |
| 9,474,605 | B2 | 10/2016 | Rowe et al. |
| 9,492,634 | B2 | 11/2016 | Moehle et al. |
| 9,498,330 | B2 | 11/2016 | Solem |
| 9,510,946 | B2 | 12/2016 | Chau et al. |
| 9,545,305 | B2 | 1/2017 | Wilson et al. |
| 9,579,199 | B2 | 2/2017 | Hauser et al. |
| 9,629,720 | B2 | 4/2017 | Nguyen et al. |
| 9,636,223 | B2 | 5/2017 | Khalil et al. |
| 9,763,781 | B2 | 9/2017 | Kramer |
| 9,763,782 | B2 | 9/2017 | Solem |
| 9,827,101 | B2 | 11/2017 | Solem et al. |
| 10,047,421 | B2 | 8/2018 | Khan et al. |
| 10,300,286 | B2 | 5/2019 | Ward et al. |
| 10,383,729 | B2 | 8/2019 | Quinn |
| 10,682,231 | B2 | 6/2020 | Quinn |
| 10,952,854 | B2 | 3/2021 | Heneghan et al. |
| 10,987,220 | B2 | 4/2021 | Quinn |
| 11,207,182 | B2 | 12/2021 | Heneghan et al. |
| 11,219,525 | B2 | 1/2022 | Vesely et al. |
| 11,364,365 | B2 | 6/2022 | Regnier et al. |
| 12,036,121 | B2 | 7/2024 | Heneghan et al. |
| 12,226,314 | B2 | 2/2025 | Reimer et al. |
| 12,420,067 | B2 | 9/2025 | Balkovec |
| 12,433,750 | B2 | 10/2025 | Vesely et al. |
| 2002/0103532 | A1 | 8/2002 | Langberg et al. |
| 2003/0105520 | A1 | 6/2003 | Alferness et al. |
| 2003/0109852 | A1 | 6/2003 | Peterson et al. |
| 2003/0181855 | A1 | 9/2003 | Simpson et al. |
| 2004/0059351 | A1 | 3/2004 | Eigler et al. |
| 2004/0102830 | A1 | 5/2004 | Williams |
| 2004/0127981 | A1 | 7/2004 | Rahdert et al. |
| 2004/0138744 | A1 | 7/2004 | Lashinski et al. |
| 2004/0153146 | A1 | 8/2004 | Lashinski et al. |
| 2004/0210307 | A1 | 10/2004 | Khairkhahan |
| 2004/0225354 | A1 | 11/2004 | Allen et al. |
| 2004/0243229 | A1 | 12/2004 | Vidlund et al. |
| 2005/0033446 | A1 | 2/2005 | Deem et al. |
| 2005/0070999 | A1 * | 3/2005 | Spence ................ A61F 2/2448 623/2.37 |
| 2005/0075723 | A1 | 4/2005 | Schroeder et al. |
| 2005/0107810 | A1 | 5/2005 | Morales et al. |
| 2005/0107871 | A1 | 5/2005 | Realyvasquez et al. |
| 2005/0187616 | A1 | 8/2005 | Realyvasquez |
| 2005/0222488 | A1 | 10/2005 | Chang et al. |
| 2005/0228495 | A1 | 10/2005 | Macoviak |
| 2005/0230039 | A1 | 10/2005 | Austin et al. |
| 2006/0058871 | A1 | 3/2006 | Zakay et al. |
| 2006/0178700 | A1 | 8/2006 | Quinn |
| 2006/0193899 | A1 | 8/2006 | Sawhney |
| 2006/0241745 | A1 | 10/2006 | Solem |
| 2007/0093890 | A1 | 4/2007 | Eliasen et al. |
| 2007/0185571 | A1 | 8/2007 | Kapadia et al. |
| 2007/0198082 | A1 | 8/2007 | Kapadia et al. |
| 2007/0232992 | A1 | 10/2007 | Kutsko et al. |
| 2007/0255399 | A1 | 11/2007 | Eliasen et al. |
| 2007/0265700 | A1 | 11/2007 | Eliasen et al. |
| 2008/0033541 | A1 | 2/2008 | Gelbart et al. |
| 2008/0243245 | A1 | 10/2008 | Thambar et al. |
| 2009/0076600 | A1 | 3/2009 | Quinn |

(56) References Cited

U.S. PATENT DOCUMENTS

2009/0149949 A1 6/2009 Quinn
2009/0240326 A1 9/2009 Wilson et al.
2009/0281618 A1* 11/2009 Hill ...................... A61F 2/2457 623/1.26
2010/0185276 A1 7/2010 Vidlund et al.
2010/0217382 A1 8/2010 Chau et al.
2010/0262233 A1 10/2010 He
2010/0298929 A1 11/2010 Thornton et al.
2010/0298930 A1 11/2010 Orlov
2011/0022004 A1 1/2011 Kipperman
2011/0022164 A1 1/2011 Quinn et al.
2011/0060407 A1 3/2011 Ketai et al.
2011/0112632 A1 5/2011 Chau et al.
2011/0224784 A1 9/2011 Quinn
2011/0257721 A1 10/2011 Tabor
2012/0010700 A1 1/2012 Spenser
2012/0046739 A1 2/2012 Von Oepen et al.
2012/0109079 A1 5/2012 Asleson et al.
2012/0150290 A1* 6/2012 Gabbay ................ A61F 2/2466 623/2.37
2012/0232563 A1 9/2012 Williams et al.
2013/0018459 A1 1/2013 Maisano et al.
2013/0090728 A1* 4/2013 Solem .................. A61F 2/2418 623/2.12
2013/0172978 A1 7/2013 Vidlund et al.
2013/0310928 A1 11/2013 Morriss et al.
2013/0325110 A1* 12/2013 Khalil .................. A61F 2/2427 623/2.11
2013/0338763 A1 12/2013 Rowe et al.
2014/0031928 A1 1/2014 Murphy et al.
2014/0039615 A1 2/2014 Padala et al.
2014/0135910 A1 5/2014 Hauser et al.
2014/0200657 A1 7/2014 Maurer et al.
2014/0207230 A1 7/2014 Wilson et al.
2014/0243968 A1 8/2014 Padala
2014/0257347 A1 9/2014 Eidenschink
2014/0276395 A1 9/2014 Wilson et al.
2014/0276971 A1 9/2014 Kovach
2014/0277427 A1 9/2014 Ratz et al.
2014/0336751 A1 11/2014 Kramer
2014/0350662 A1 11/2014 Vaturi
2014/0379075 A1 12/2014 Maurer et al.
2015/0051693 A1 2/2015 Bertolino et al.
2015/0073547 A1 3/2015 Eliasen et al.
2015/0112429 A1 4/2015 Khairkhahan et al.
2015/0127097 A1 5/2015 Neumann et al.
2015/0134050 A1 5/2015 Solem et al.
2015/0202043 A1 7/2015 Zakai et al.
2015/0223934 A1 8/2015 Vidlund et al.
2015/0257884 A1 9/2015 Subramanian et al.
2015/0305861 A1 10/2015 Annest
2015/0327994 A1 11/2015 Morriss et al.
2016/0030166 A1 2/2016 Kapadia
2016/0074164 A1 3/2016 Naor
2016/0081798 A1 3/2016 Kocaturk
2016/0089233 A1 3/2016 Lee et al.
2016/0089239 A1 3/2016 Hauser et al.
2016/0113762 A1 4/2016 Clague et al.
2016/0166380 A1 6/2016 Seguin et al.
2016/0166382 A1 6/2016 Nguyen
2016/0166416 A1 6/2016 Yacoby et al.
2016/0175122 A1 6/2016 O'Shaughnessy et al.
2016/0184098 A1 6/2016 Vaturi
2016/0193043 A1 7/2016 Kim
2016/0199181 A1 7/2016 Kramer
2016/0242909 A1 8/2016 Ketai et al.
2016/0262741 A1 9/2016 Gilmore et al.
2016/0262886 A1 9/2016 Wang
2016/0278920 A1 9/2016 Braido et al.
2016/0287387 A1 10/2016 Wei
2016/0317788 A1 11/2016 Merkel
2017/0035561 A1 2/2017 Rowe et al.
2017/0143478 A1 5/2017 Schwartz et al.
2017/0196687 A1 7/2017 Braido et al.
2017/0209265 A1 7/2017 Karapetian et al.
2017/0216575 A1 8/2017 Asleson et al.
2017/0224444 A1 8/2017 Viecilli et al.
2017/0224477 A1 8/2017 Seguin
2017/0239041 A1 8/2017 Quinn
2017/0266003 A1 9/2017 Hammer et al.
2018/0028779 A1 2/2018 Von Oepen et al.
2018/0168803 A1 6/2018 Pesce et al.
2018/0228610 A1 8/2018 Lashinski et al.
2018/0235791 A1 8/2018 Kang et al.
2019/0029811 A1 1/2019 Bishop et al.
2019/0083263 A1 3/2019 Hariton et al.
2019/0209297 A1 7/2019 Metchik et al.
2020/0155332 A1 5/2020 Longo et al.
2020/0155798 A1 5/2020 Yang et al.
2020/0155804 A1 5/2020 Von Oepen et al.
2020/0254160 A1 8/2020 Stack et al.
2020/0297491 A1 9/2020 Argento et al.
2020/0367871 A1 11/2020 Van Hoven et al.
2021/0001085 A1 1/2021 Schmidt et al.
2021/0077257 A1 3/2021 Vesely et al.
2021/0283373 A1 9/2021 Porter
2021/0322166 A1 10/2021 Von Oepen et al.
2022/0054269 A1 2/2022 Khairkhahan
2022/0160997 A1 5/2022 Hou et al.
2022/0192630 A1 6/2022 Schmidt et al.
2022/0280297 A1 9/2022 Zhang et al.
2023/0001150 A1 1/2023 Tang et al.
2023/0080273 A1 3/2023 Winston et al.
2023/0330390 A1 10/2023 Schmidt et al.
2024/0091491 A1 3/2024 Davis et al.
2024/0261101 A1 8/2024 Mulligan et al.
2024/0350772 A1 10/2024 Shao et al.
2025/0049424 A1 2/2025 Willenbrink
2025/0249215 A1 8/2025 Gabay et al.
2025/0352342 A1 11/2025 Vesely et al.
2025/0367408 A1 12/2025 Monteon et al.
2026/0048236 A1 2/2026 Slam et al.

FOREIGN PATENT DOCUMENTS

CA 2729027 A1 12/2009
CA 2863939 A1 8/2012
CA 2842288 A1 1/2013
CA 2871156 A1 11/2013
CA 2872611 A1 11/2013
CN 101484093 A 7/2009
CN 102781371 A 11/2012
CN 102858272 A 1/2013
CN 202821715 U 3/2013
CN 105455924 A 4/2016
CN 104768500 B 10/2017
CN 109846579 A 6/2019
DE 102013017750 A1 4/2015
DE 102013017993 A1 6/2015
EP 1796597 A2 6/2007
EP 2032078 A1 3/2009
EP 2032080 A2 3/2009
EP 2150206 A1 2/2010
EP 2465568 A1 6/2012
EP 2849681 A1 3/2015
EP 1871300 B1 4/2016
EP 3023117 A1 5/2016
EP 3042615 A1 7/2016
EP 3056170 A1 8/2016
EP 2023858 B1 10/2016
EP 3081195 A1 10/2016
EP 2032080 B1 5/2017
EP 3187150 A1 7/2017
EP 3241525 A1 11/2017
ES 2586111 T3 10/2016
JP 2013517830 A 5/2013
JP 2016512721 A 5/2016
JP 2016512726 A 5/2016
JP 2016521633 A 7/2016
RU 2014153781 A 7/2016
WO WO-9640347 A1 12/1996
WO WO-2000032137 A1 6/2000
WO WO-0060995 A2 10/2000
WO WO-03059209 A2 7/2003

(56) References Cited

FOREIGN PATENT DOCUMENTS

| | | | |
|---|---|---|---|
| WO | WO-2004105647 | A1 | 12/2004 |
| WO | WO-2004112658 | A1 | 12/2004 |
| WO | WO-2005087140 | A1 | 9/2005 |
| WO | WO-2006064490 | A1 | 6/2006 |
| WO | WO-2006102329 | A1 | 9/2006 |
| WO | WO-2006111391 | A1 | 10/2006 |
| WO | WO-2007016097 | A2 | 2/2007 |
| WO | WO-2007050256 | A2 | 5/2007 |
| WO | WO-2007078772 | A1 | 7/2007 |
| WO | WO-2007144865 | A1 | 12/2007 |
| WO | WO-2008141322 | A1 | 11/2008 |
| WO | WO-2009026563 | A2 | 2/2009 |
| WO | WO-2009053952 | A2 | 4/2009 |
| WO | WO-2011034973 | A3 | 5/2011 |
| WO | WO-2012035279 | A1 | 3/2012 |
| WO | WO-2013016618 | A2 | 1/2013 |
| WO | WO-2013028387 | A2 | 2/2013 |
| WO | WO-2015123597 | A1 | 8/2015 |
| WO | WO-2016000274 | A1 | 1/2016 |
| WO | WO-2016050751 | A1 | 4/2016 |
| WO | WO-2016059533 | A1 | 4/2016 |
| WO | WO-2016079734 | A1 | 5/2016 |
| WO | WO-2016114719 | A1 | 7/2016 |
| WO | WO-2016130706 | A1 | 8/2016 |
| WO | WO-2016178136 | A1 | 11/2016 |
| WO | WO-2017079234 | A1 | 5/2017 |
| WO | WO-2017091605 | A1 | 6/2017 |
| WO | WO-2019119674 | A1 | 6/2019 |
| WO | WO-2019154927 | A1 | 8/2019 |
| WO | WO-2020197854 | A1 | 10/2020 |
| WO | WO-2021024183 | A1 | 2/2021 |
| WO | WO-2022261022 | A1 | 12/2022 |
| WO | WO-2023026113 | A1 | 3/2023 |
| WO | WO-2023122695 | A1 | 6/2023 |
| WO | WO-2024161309 | A1 | 8/2024 |

OTHER PUBLICATIONS

U.S. Appl. No. 16/943,621 / U.S. Pat. No. 10,952,854, filed Jul. 30, 2020 / Mar. 22, 2021.

U.S. Appl. No. 17/107,565, filed Nov. 30, 2020.

U.S. Appl. No. 17/205,813, filed Mar. 18, 2021.

International Search Report & Written Opinion dated Dec. 20, 2022 in Int'l PCT Patent Appl. Serial No. PCT/IB2022/056960 (0510).

Berger et al., Comparison of results and complications of surgical and Amplatzer device closure of atrial septal defects, J. Thorac. Cardiovasc. Surg., 118(4):674-8 (1999).

Campelo-Parada, et al., First-in-Man Experience of a Novel Transcatheter Repair System For Treating Severe Tricuspid Regurgitation, J. Am. Coll. Cardiol., 66(22):2475-83 (2015).

Espiritu, et al., Transcatheter Mitral Valve Repair Therapies: Evolution, Status and Challenges, Annals of Biomedical Engineering, 45(2):332-359 (2017).

Extended EP Search Report dated Sep. 7, 2018 in EP Patent Application Serial No. 18165070.6.

International Search Report & Written Opinion dated Nov. 17, 2020 in Int'l PCT Patent Appl. Serial No. PCT/IB2020/057368 (0410).

International Search Report and Written Opinion dated Jul. 10, 2019 in Int'l PCT Patent Appl. Serial No. PCT/EP2019/053038 (0310).

International Search Report dated Dec. 1, 2015 in Intl PCT Patent Appl. No. PCT/EP2015/072388 (0210).

Peppas, et al., Preclinical in vivo long-term evaluation of the novel Mitra-Spacer technology: experimental validation in the ovine model, EuroIntervention, 13(3):272-279 (2017).

International Search Report & Written Opinion dated May 3, 2024 in Int'l PCT Patent Appl. Serial No. PCT/IB2024/050858.

International Search Report & Written Opinion dated Mar. 12, 2026 in Int'l PCT Patent Appl. Serial No. PCT/IB2025/059446.

Invitation to Pay Additional Fees/Partial Search Report dated Apr. 20, 2026 in Int'l PCT Patent Appl. Serial No. PCT/IB2026/050522.

* cited by examiner

HEART VALVE TREATMENT DEVICE AND METHOD

CROSS-REFERENCE TO RELATED APPLICATIONS

This application is a continuation of U.S. patent application Ser. No. 16/900,791, filed Jun. 12, 2020, now U.S. Pat. No. 10,987,220, which is a continuation of U.S. patent application Ser. No. 16/443,792, filed Jun. 17, 2019, now U.S. Pat. No. 10,682,231, which is a continuation of U.S. patent application Ser. No. 15/514,204, filed Mar. 24, 2017, now U.S. Pat. No. 10,383,729, which is a national phase of International PCT Patent Application Serial No. PCT/EP2015/072388, filed Sep. 29, 2015, which claims the benefit of EP Patent Application Serial No. 15168947.8, filed May 22, 2015, EP Patent Application Serial No. 14190855.8, filed Oct. 29, 2014 and EP Patent Application Serial No. 14186930.4, filed Sep. 29, 2014, the entire contents of each of which are incorporated herein by reference.

FIELD OF THE INVENTION

The invention relates to surgical devices and methods, specifically for treating the heart.

In particular the invention relates to treating leaking heart valves, such as the atrioventricular (AV) valves.

The heart contains four valves, two semilunar, the aortic and pulmonary valves, and two AV valves, the mitral and tricuspid valves. The heart fills with blood from the lungs and body when the AV valves are open. When the heart pumps or contracts, the AV valves close and prevent the blood from regurgitating backwards. The semilunar valves open when the heart pumps allowing the blood to flow into the aorta and main pulmonary artery.

PRIOR ART DISCUSSION

Dysfunction of the cardiac AV valves is common and can have profound clinical consequences. Failure of the AV valves to prevent regurgitation leads to an increase in the pressure of blood in the lungs or liver and reduces forward blood flow. Valvular dysfunction either results from a defect in the valve leaflet or supporting structure, or dilation of the fibrous ring supporting the valve. These factors lead to a failure of valve leaflets to meet one another, known as co-aptation, allowing the blood to travel in the wrong direction.

Conventional treatment of leaking AV valves often involves replacement or operative repair of the valves. These treatments are considerable surgical operations requiring cardiopulmonary bypass and are associated with significant morbidity. In many instances patients are too sick or too frail to undergo these operations and hospital stays and recovery phases after such operations are prolonged.

Percutaneous techniques of valve repair have the advantage of being significantly less traumatic for the patient. During such procedures the valve repair is performed from within the heart, accessing the heart through a vein in the neck or the groin. Percutaneous procedures are performed under local anaesthetic and the incisions required to perform the procedures are extremely small. In addition, procedural times and recovery phases are also expected to be significantly less. Current attempts at percutaneous repair of leaking heart valves include insertion of a mitral valve support structure into a large cardiac vein known as the coronary sinus. Another is insertion of a stitch or clip into the mitral valve leaflets to hold them together*. Another is insertion of a new prosthetic valve percutaneously.

WO2006/064490 (Mednua) describes a device with a generally cylindrical treatment element for location between a pair of valve leaflets. The device occludes tire valve opening to resist retrograde flow. A tether extends into the ventricle and is connected to an anchor engaging the ventricle wall to support the device.

WO2007/144865 (Mednua) also describes a device for treatment of a mitral valve, located in the region of co-aptation of the native leaflets. An anchor element anchors the device to the ventricle wall at the apex of the ventricle.

WO2009/053952 (Mednua) describes a percutaneous approach in which a treatment element is located between a pair of valve leaflets. A support has an anchor with for example a screw for engaging heart wall tissue. The treatment element comprises a hydrogel.

US2013/0090728 (Edwards Lifesciences AG) describes an approach in which a mitral valve flow improvement device is percutaneously inserted. It has a prosthetic mitral valve leaflet, and a tissue-penetrating anchor. Blood flow from the left ventricle to the left atrium expands the prosthetic leaflet into the closed state so that it is umbrella-shaped. Support for the device is provided by either a stent-like support or by anchors which engage tissue within the heart.

US2013/0325110 (Edwards Lifesciences Corp.) describes devices for improving the functioning of a defective heart valve. A locking mechanism locks position of a co-apting element within the tricuspid valve (TV) and relative to a fixed anchor rail. The locking mechanism is a collet mechanism which locks a catheter onto the anchor rail, which runs through the catheter. The catheter and rail exit the subclavian vein (SV) at a puncture and remain implanted. The locking mechanism remains external, on a coil of the catheter/rail. An alternative arrangement is crimping the catheter onto the rail near the entry point.

US2013/0338763 (Edwards Lifesciences) also describes a heart valve co-aptation system with a locking collet. It also discloses anchoring of the co-aptation element using stent structures which straddle the tricuspid valve.

The invention is directed towards providing an improved heart valve treatment device for percutaneous delivery.

SUMMARY OF THE INVENTION

According to the invention, there is provided a heart valve therapeutic device comprising:

- a support comprising an elongate anchor configured to percutaneously extend through a blood vessel to the heart, and
- a prosthetic valve element comprising a coupler for coupling the valve element to the anchor, and
- a user actuator for allowing user coupling of the valve element on the anchor at a desired location.

In one embodiment, the anchor has a stiffness to hold its shape and location to support the valve element. Preferably, the device comprises a stylet or a shaped or stiff collar arranged to provide a desired shape to the anchor. Preferably, the anchor has a variable and lockable shape.

In one embodiment, the elongate anchor comprises a distal fixing element for fixing to a heart wall.

In one embodiment, the user actuator is at a proximal end of the device and is configured to adjust orientation and/or shape of the valve element on the anchor.

In one embodiment, the valve element comprises at least one coupler connecting the valve element to tire elongate anchor at a distal location adjacent the valve element.

In one embodiment, the device comprises a user actuator for allowing user control of the valve element shape and/or location, and wherein the actuator is arranged to change axial position of the or each coupler on the elongate anchor.

In one embodiment, the actuator comprises control cables which are arranged to be moved axially under surgeon control. Preferably, the coupler comprises an annular spring or clip which contracts around the elongate anchor, the device further comprises a delivery catheter, and said coupler is configured to support the valve element after removal of the delivery catheter.

In one embodiment, the device comprises an adjustment mechanism for varying individual chords connecting at least one coupler to the prosthetic valve element, and wherein the mechanism is arranged to shorten one or more chords and lengthen one or more other chords. Preferably, the device comprises at least two couplers supporting the valve element on the anchor and the actuator is configured to set mutual separation of the couplers for configuration of the valve element.

In one embodiment, the device comprises a user actuator for allowing user control of the valve element shape and/or location and said actuator is arranged to control said adjustment mechanism. Preferably, the actuator comprises a mechanism which shortens or lengthens linking of a support ring to the anchor, for tilting of the valve element. Preferably, said ring is configured to engage atrium tissue and the valve element further comprises arms extending distally and axially.

In one embodiment, the device comprises an adjustment mechanism for varying said chords to adjust angle of the valve element with respect to the axis of the elongate anchor In one embodiment, the valve element comprises prosthetic leaflets shaped for co-apting with native leaflets, and said prosthetic leaflets have together a smaller radial dimension for at least some of their length when the native leaflets are closed and a larger radial dimension when the native leaflets are open. Preferably, the valve element comprises prosthetic valve leaflets that are supported to extend axially and radially outwardly towards the proximal end, with an apex facing into a heart chamber in use. In one embodiment, the prosthetic valve leaflets are supported at their proximal end on a ring.

In one embodiment, the prosthetic valve leaflets are arranged so that in use blood flows through the centre of the valve.

In one embodiment, the support includes a radial support part which is radially distant from the anchor and is configured to engage atrial tissue on a proximal side of a valve. Preferably, the radial support part comprises a ring extending around a device axis. In one embodiment, the ring is on spokes.

In one embodiment, the ring is connected to chords extending from a coupler on an anchor.

In one embodiment, the radial support comprises at least one fixation device for engaging tissue radially of the anchor. In one embodiment, each radial fixation device has at least one hook or barb, for example in a Y-shape with barbs.

In one embodiment, the radial support is spring-loaded in the radial direction.

In one embodiment, the radial support is adapted to engage on both sides of a native valve, comprising a proximal ring for engagement on the atrium side and a fixation device on radial arms for engagement on the ventricular side.

In one embodiment, the ring comprises a proximal skirt arranged to prevent regurgitation between the native leaflets and the valve element. In one embodiment, said skirt comprises a rim of material. In one embodiment, said rim is of material which is the same material as material of valve element leaflets sewn or glued to a distal side of the radial support.

In one embodiment, said radial support is configured to engage atrial tissue to provide support for the anchor, and the anchor is not configured to directly engage tissue for support.

In one embodiment, the anchor is configured to rest against a posterior atrial wall upon deployment.

In one embodiment, the distal end of the support is deflectable such that position of the support can be altered to position the valve element to provide maximum reduction in regurgitation, the device comprising a mechanism for altering tension in elements within the support.

In one embodiment, the radial support abuts against a coupler of the valve attached to the anchor.

In one embodiment, the actuator further comprises a controller arranged to be implanted subcutaneously on the anchor to allow the position of the valve element to be changed after insertion.

In one embodiment, the device comprises an element for clamping the anchor to a wall through which the anchor passes.

In one embodiment, the valve element comprises leaflets shaped like native leaflets and having a ring-shaped support around its circumference.

In one embodiment, the valve is only supported by a support in the form of the anchor without a fixing element, In one embodiment, the valve element is connected to the anchor by a coupler so that rotation of the support moves the valve to fit to the shape of the native valve.

In one embodiment, the support comprises a ring and one or more members extending distally such that they cross an AV valve in use, said members including a member interconnecting opposed sides of the ring.

In one embodiment, the support includes a ring which is circular or oval or crescent-shaped.

In one embodiment, the device further comprises a delivery catheter for delivering and positioning the valve element on the anchor.

In one embodiment, the device further comprises a sheath for delivering the anchor.

In one embodiment, the valve element comprises at least one fenestration configured to, in use, provide central flow such as washing jets to prevent or reduce thrombosis, wherein the fenestrations are at or adjacent to the base of the prosthetic valve element.

In one embodiment, there are a plurality of fenestrations arranged circumferentially around a valve element axis, and wherein the fenestrations each have a cross-sectional area in the range of 0.5 $mm^2$ to 3 $mm^2$, and they may have any suitable shape to suit the available areas such as circular, triangular, square or slit-like.

In one embodiment, the valve element comprises leaflets which are cup-shaped and are secured directly to a support frame which attaches to the anchor.

In another aspect, the invention provides a heart valve therapeutic kit comprising a plurality of devices as defined above in any embodiment, at least some of which are of different sizes to suit different sizes of patient valve defects.

In another aspect, the invention provides a pacemaker comprising a device as defined above in any embodiment and pacemaker electrodes mounted on the anchor at a distal end of the anchor.

In a further aspect, the invention provides a method of delivering a device as defined above in any embodiment into a patient's heart, the method comprising inserting the anchor by moving it along a blood vessel until a distal end of the anchor traverses an AV valve in the heart, delivering the valve element to the area of the AV valve, and causing the valve element to engage the anchor at a desired location for co-aptation with native leaflets of the AV valve.

In one embodiment, the anchor is deflectable and the method comprises adjusting shape of the anchor for optimum positioning of the valve element. Preferably the anchor is locked at the optimum configuration.

In one embodiment, the guide sheath is dedicated to insertion of the anchor.

In one embodiment, the valve element is delivered by moving the valve element along the anchor until a desired position is reached, and withdrawing a delivery sheath to expose the valve and allow it to couple to the anchor at said position.

In one embodiment, the delivery sheath withdrawal removes a radial support for a coupler, allowing the coupler to contract around the anchor.

In one embodiment, the anchor is shaped to have a bend at an atrial wall, so that the atrial wall provides axial support against movement in the proximal direction upon closing of the ventricle.

In one embodiment, the anchor is shaped to have a fixed bend as it crosses the interatrial septum.

Additional Summary Aspects According to the invention, there is provided a heart valve therapeutic device comprising:

- a support, and
- a prosthetic valve being arranged to be supported by the support,
- wherein the prosthetic valve is arranged to have a shape and/or location to suit the nature of defect in the heart valve.

In one embodiment, the support comprises an elongate anchor having a distal fixing element for fixing to a heart wall, and the prosthetic valve is supported on the anchor by at least one coupler at a desired location. In one embodiment, the device comprises a user actuator for allowing user-control of the valve shape and/or location. In one embodiment, the actuator is at a proximal end of the device, hi one embodiment, the prosthetic valve comprises a proximal coupler, and leaflets connected to the coupler by chords. Preferably, the prosthetic valve comprises proximal and distal couplers connecting the valve to the elongate anchor. In one embodiment, the device comprises a user actuator for allowing user control of the valve shape and/or location, and wherein the actuator is arranged to change relative axial position of the proximal and distal couplers. In one embodiment, the actuator comprises control cables which are arranged to be moved axially under surgeon control. Preferably, at least one of the proximal and distal couplers comprises an annular spring which contracts around the elongate anchor.

In one embodiment, the device comprises an adjustment mechanism for varying individual chords connecting at least one coupler to the prosthetic valve leaflets. In one embodiment, the mechanism is arranged to shorten one or more chords while lengthening one or more other chords or chords. In one embodiment, the device comprises a user actuator for allowing user control of the valve shape and/or location and said actuator is arranged to control said adjustment mechanism. In one embodiment, the actuator comprises a rotating mechanism which shortens or lengthens chords upon rotation of one or more actuator devices in a selected direction. In one embodiment, the chords are attached to a coupler within the anchor which can be locked down onto the anchor.

In one embodiment, the device comprises an adjustment mechanism for varying said chords to adjust angle of the leaflets with respect to the axis of the elongate anchor.

In one embodiment, the prosthetic valve comprises valve leaflets that are supported to extend axially and radially outwardly towards the proximal end, with an apex facing into a heart chamber in use. In one embodiment, the leaflets are supported at their proximal end on a ring. In one embodiment, the leaflets are arranged so that in use blood flows through the centre of the valve.

In one embodiment, the device comprises a stylet arranged to be introduced by sliding along the anchor to provide a desired shape at the prosthetic valve.

In one embodiment, the chords have fixation elements and are arranged to be fixed to a heart wall. In one embodiment, the actuator comprises an actuator device which upon rotation causes one or more chords to be fixed to the wall of the heart.

In one embodiment, the prosthetic valve comprises a deformable element which is adapted to deform to seal the chamber. Preferably, the deformable element is adapted to deform under heart chamber pressure. In one embodiment, the device comprises an actuator for assisting or solely causing deformation of the deformable element.

In one embodiment, the deformable element comprises a stem which is configured to extend into a heart chamber, and a head which remains outside, the stem decreasing in volume and expanding the head during chamber higher pressure.

In one embodiment, the prosthetic valve comprises at least one fenestration configured to, in use, provide central flow such as washing jets to prevent or reduce thrombosis. In one embodiment, the fenestrations are at or adjacent to the base of the prosthetic valve.

In one embodiment, there are a plurality of fenestrations arranged circumferentially around a device axis.

In one embodiment, the fenestrations each have a cross-sectional area in the range of 0.5 $mm^2$ to 3 $mm^2$, and they may have any suitable shape to suit the available areas such as circular, triangular, square or slit-like.

In one embodiment, the device comprises a support at least part of which is radially distant from the anchor and is configured to engage tissue. In one embodiment, the support comprises a ring extending around the device axis. In one embodiment, the ring is on spokes.

In one embodiment, the ring is on chords extending from a coupler on an anchor. In one embodiment, the support comprises at least one fixation device for engaging tissue.

In one embodiment, each fixation device has at least one hook or barb, for example in a Y-shape with two barbs, In one embodiment, the fastener is spring loaded. In one embodiment, the support is arranged to engage atrium tissue.

In one embodiment, the support is arranged to engage ventricle tissue.

In one embodiment, the support is adapted to engage on both sides of a native valve, preferably with a ring on the atrium side and fixation devices on radial arms on the ventricular side. In one embodiment, the ring comprises proximal skirt arranged to prevent regurgitation between the native leaflets and the prosthetic valve. In one embodiment, said support which engages atrial tissue is a sole support for the prosthetic device.

In one embodiment, the support is arranged to be delivered over an anchor to rest against the posterior atrial wall.

In one embodiment, the distal end of the support is deflectable by means of a mechanism that alters the tension in elements within its wall, and preferably the shape of the distal end of the support is lockable.

In one embodiment, the support abuts against a coupler of the valve attached to the anchor.

In another aspect, the invention provides a heart valve therapeutic kit comprising a plurality of devices as described above in any embodiment, at least some of which are of different sizes to suit different sizes of patient valve defects.

In various embodiments we describe a percutaneously-delivered valve made up of one or more leaflets, which can be made from porcine or bovine pericardium of other materials, which is attached to an anchor by one or more supports either on a ring on the atrial side of the native valve or directly to the anchor. The leaflets may be supported by chords which can be varied in length and position and may also be fixed to the wall of the heart. The valve may be supported by an anchor which is fixed to the wall of the heart. The valve may be supported by the proximal portion of the anchor against the atrial wall. This can be inforced by the use of stylets within the anchor. The valve may be additionally or alternatively be supported by struts or hooks on the LV (distal) side of the valve. There may be a compressive force between these and the atrial ring or they may rest against the AV groove to resist the valve moving back into the atrium. Such a support may do away with the need for the anchor and the anchor could be removed at the end of the case. In some embodiments of the device there may be fenestrations at the base of the valve to allow a small amount of blood flow back into the atrium to prevent clot formation.

In one embodiment, the support comprises an elongate wire anchor having a stiffness allowing it to provide support without fixing to a heart wall.

In one embodiment, the anchor has a variable shape.

In one embodiment, the anchor shape is lockable.

In one embodiment, the device further comprises a controller arranged to be implanted sub-cutaneously on the supports.

In one embodiment, the support comprises an element for clamping the support to a wall through which it passes.

In one embodiment, the valve comprises leaflets shaped like native leaflets and having a ring-shaped support around its circumference.

In one embodiment, the valve is only supported in a support in the form of a wire, whereby rotation of the support moves the valve to fit to the shape of the native valve structure.

In one embodiment, the support comprises a wire and a plurality of support members extending distally and radially from a location at or near a distal end of the wire.

In one embodiment, the support comprises a ring and one or more members extending distally such that they cross an AV valve in use.

In one embodiment, said members include a member interconnecting opposed sides of the ring.

In one embodiment, the support includes a ring which is circular or oval or crescent-shaped.

DETAILED DESCRIPTION OF THE INVENTION

The invention will be more clearly understood from the following description of some embodiments thereof, given by way of example only with reference to the accompanying drawings in which:—

FIGS. 1 to 6 are a series of diagrams illustrating deployment of a device of the invention to treat a patient's AV valve;

FIGS. 7(*a*) and 7(*b*) are diagrams illustrating adjustment of a prosthetic valve of the device when deployed;

Figure 21A:
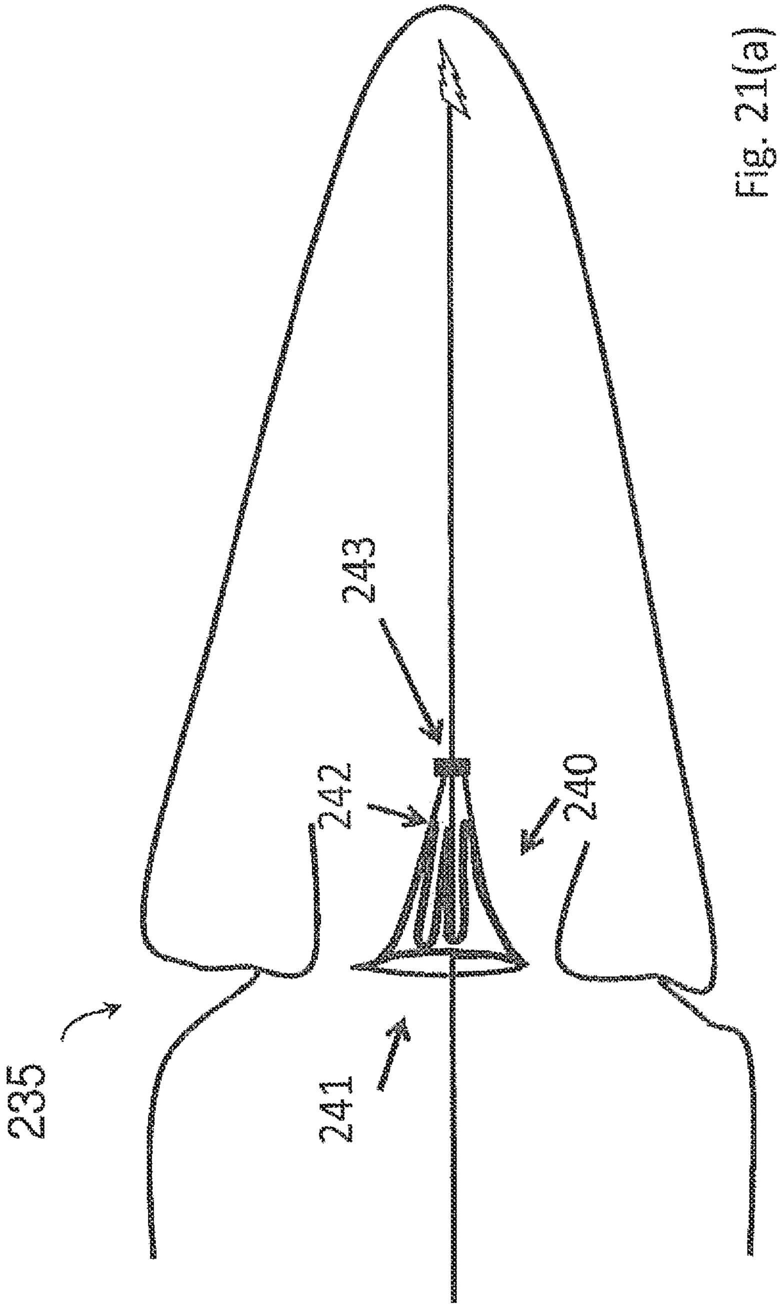
Figure 21B:
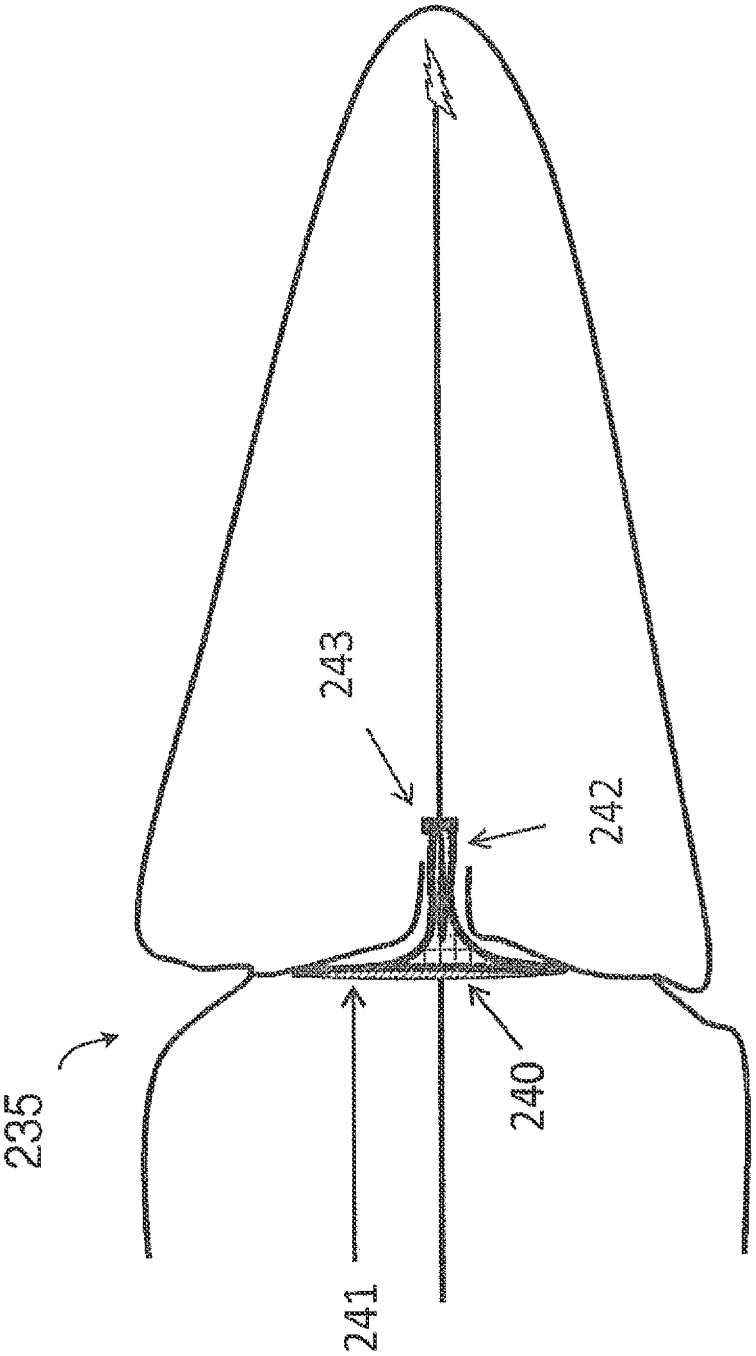
Figure 22:
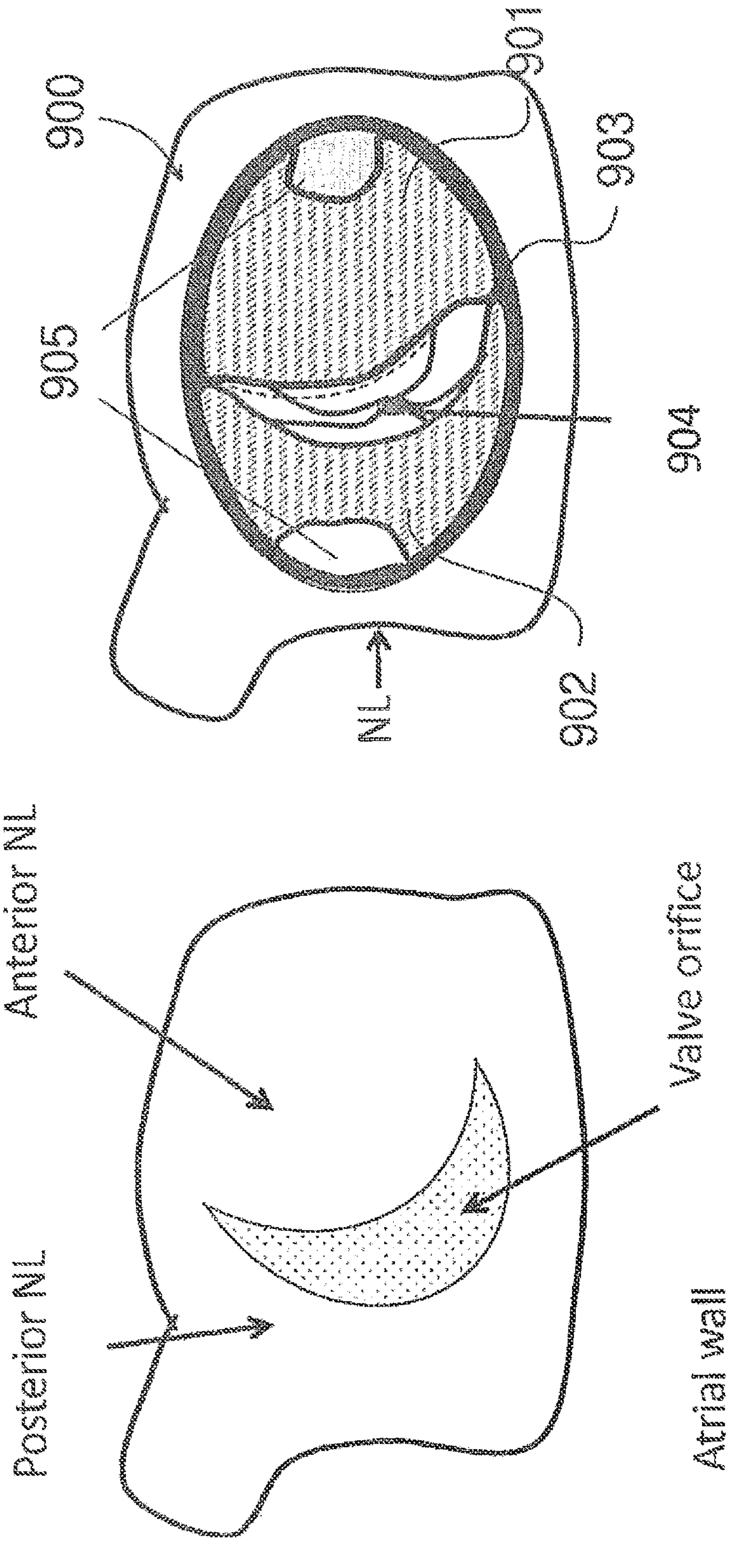
Figure 23:
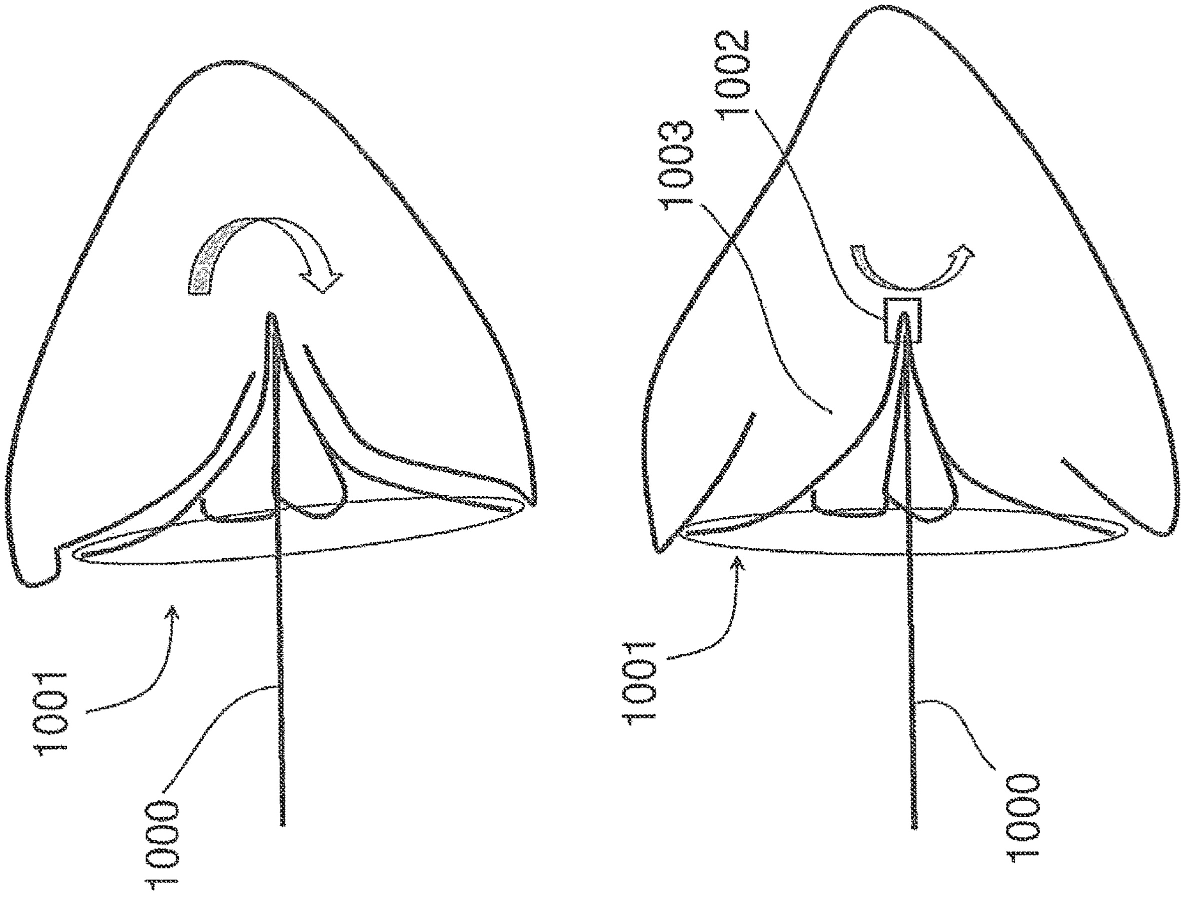
Figure 24:
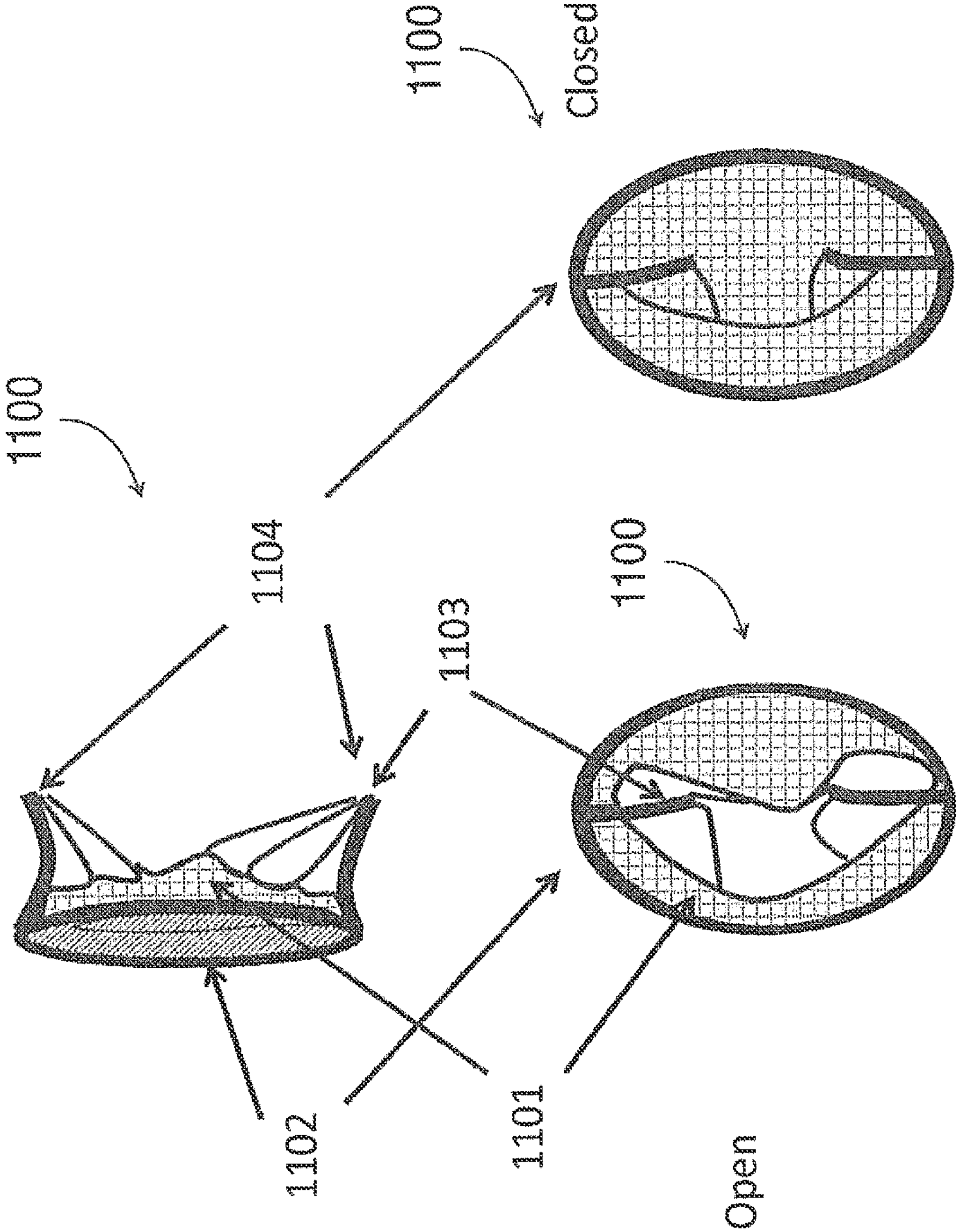
Figure 25:
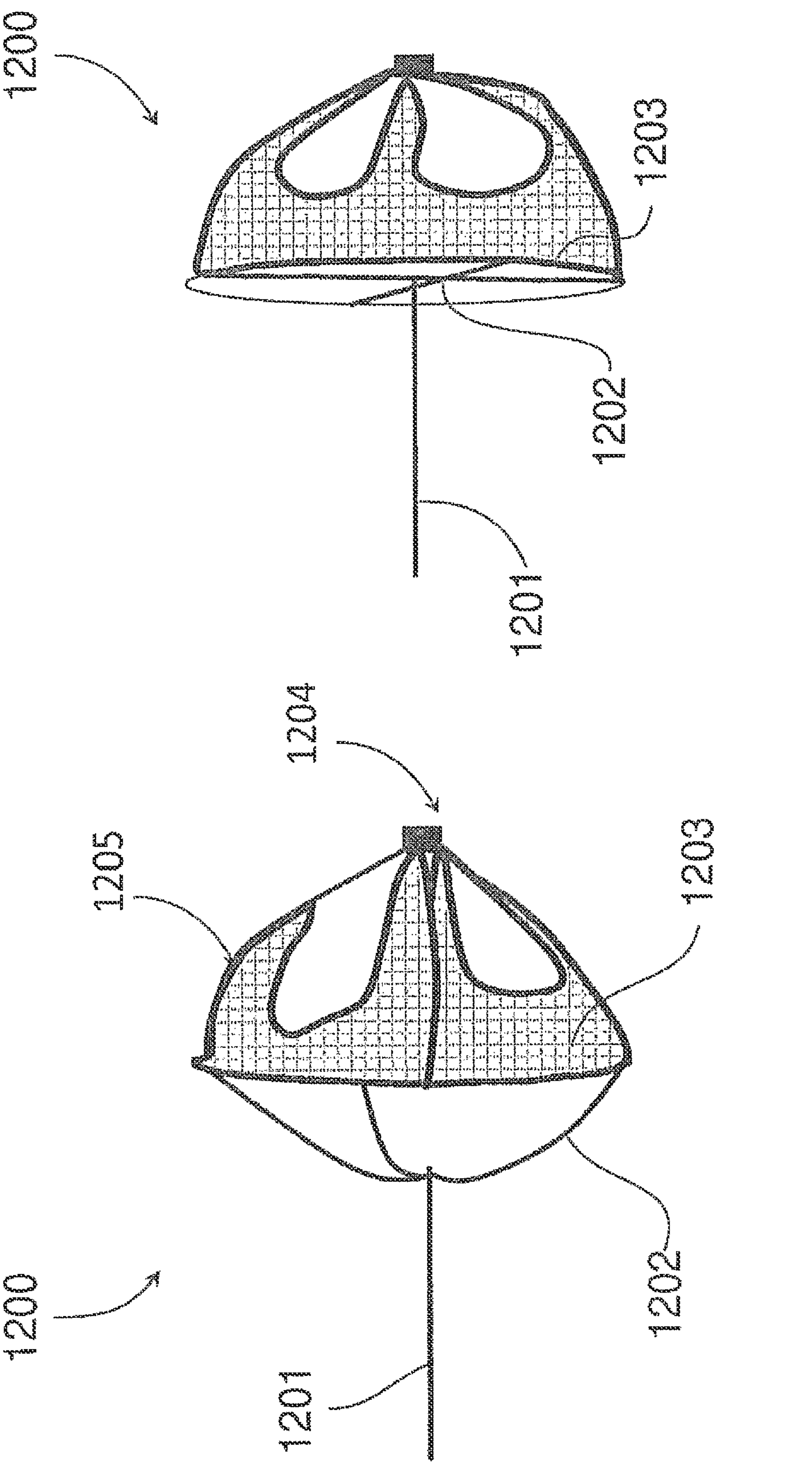
Figure 26:
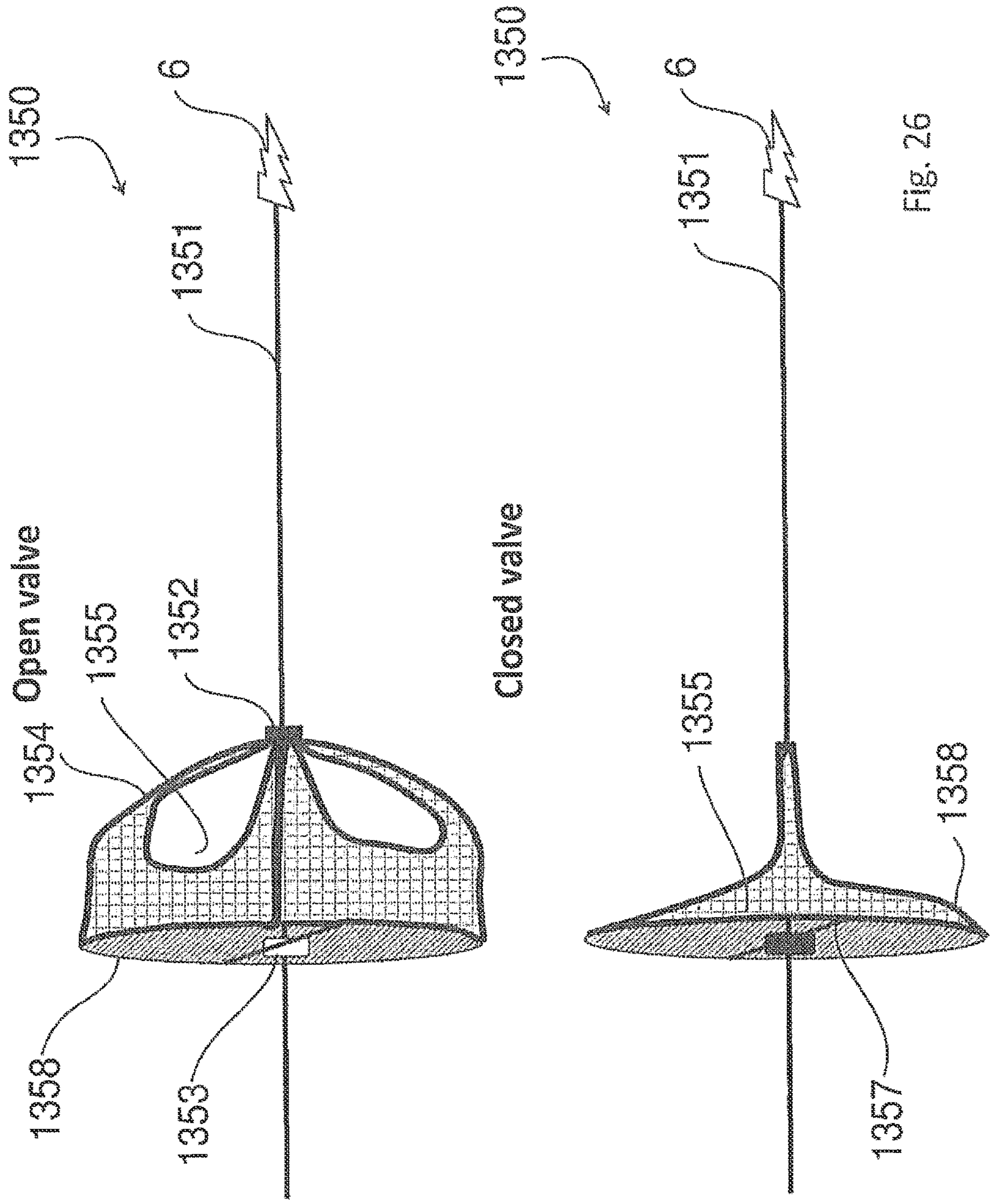
Figure 27:
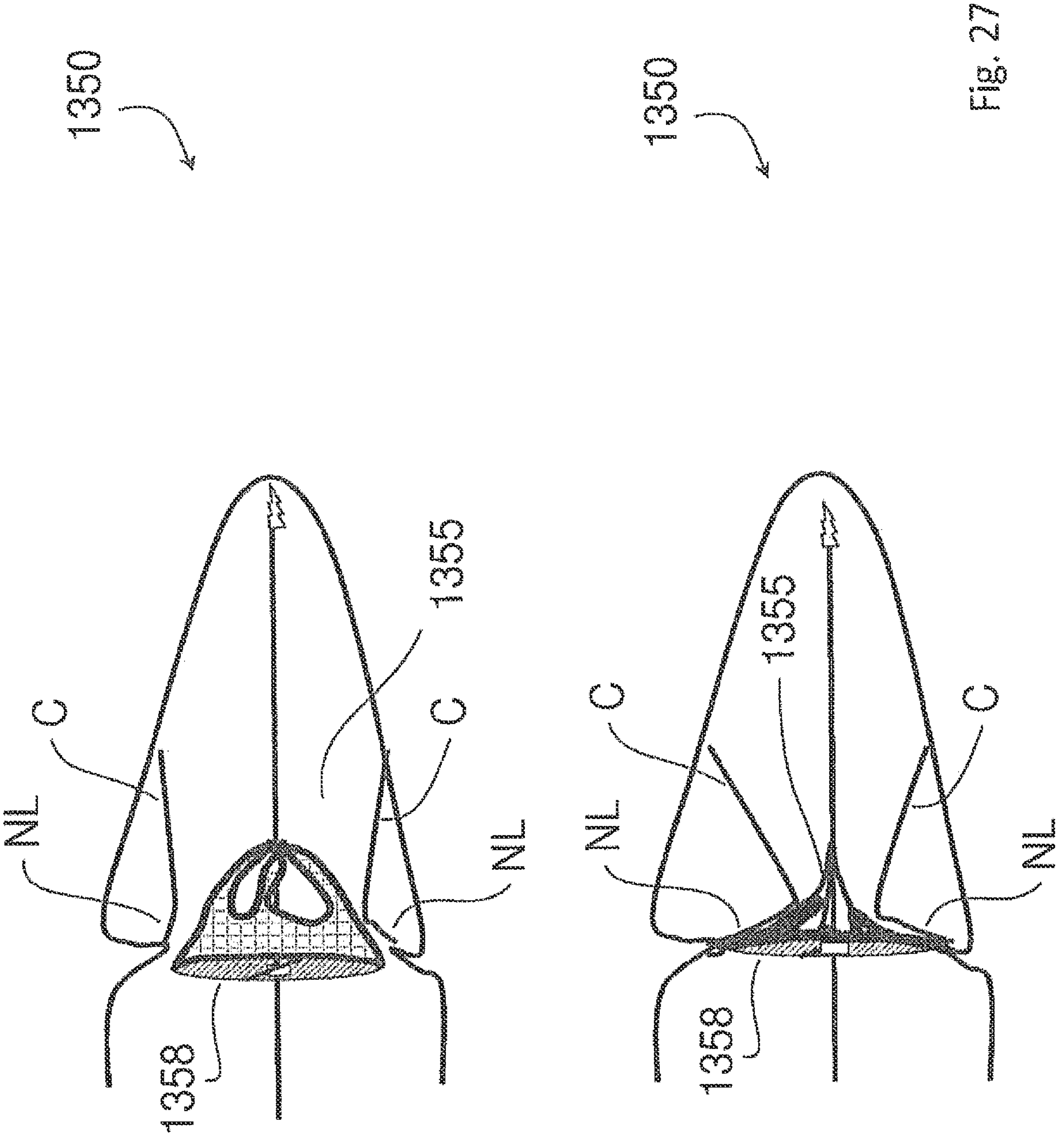
Figure 28:
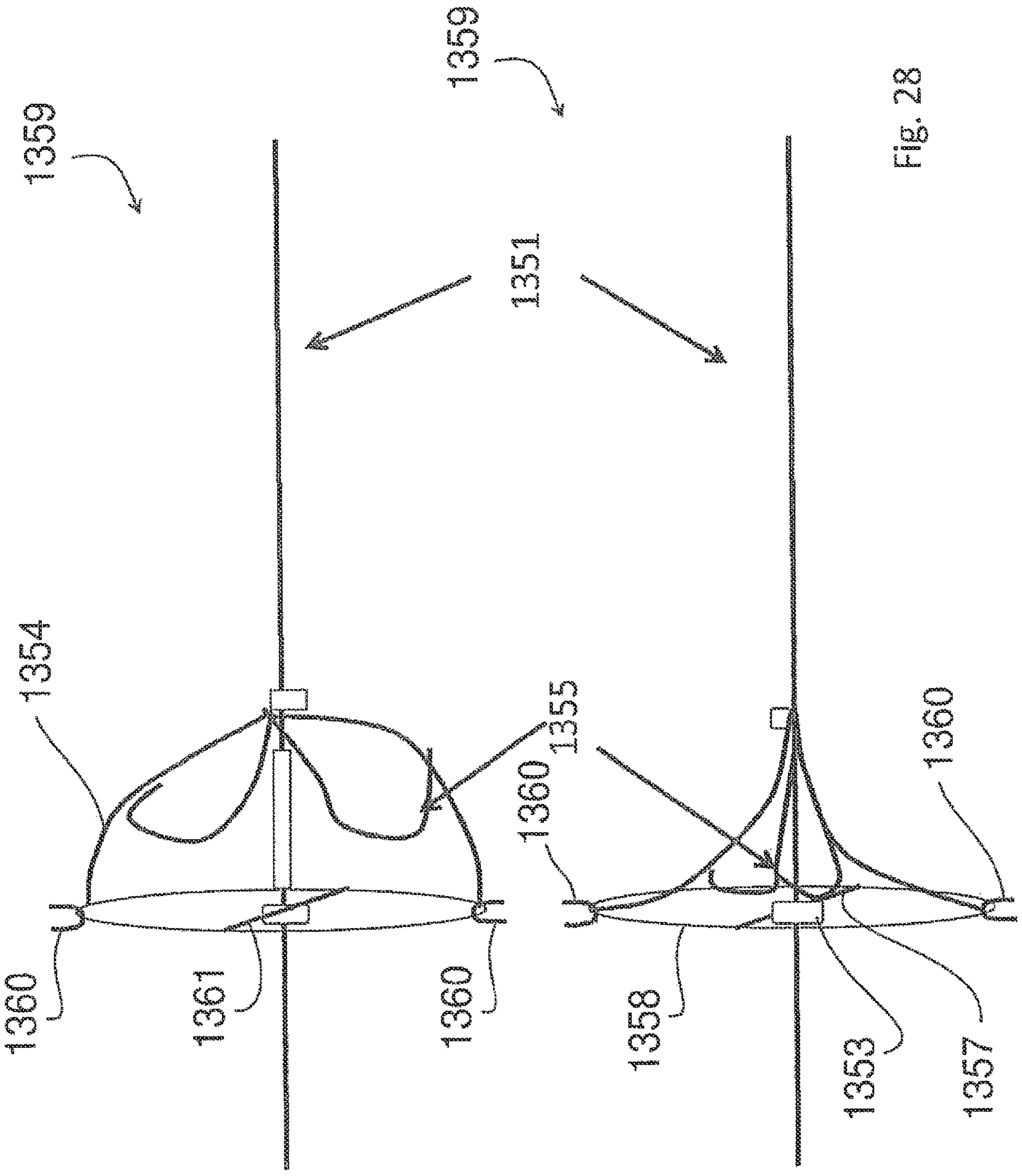
Figure 29:
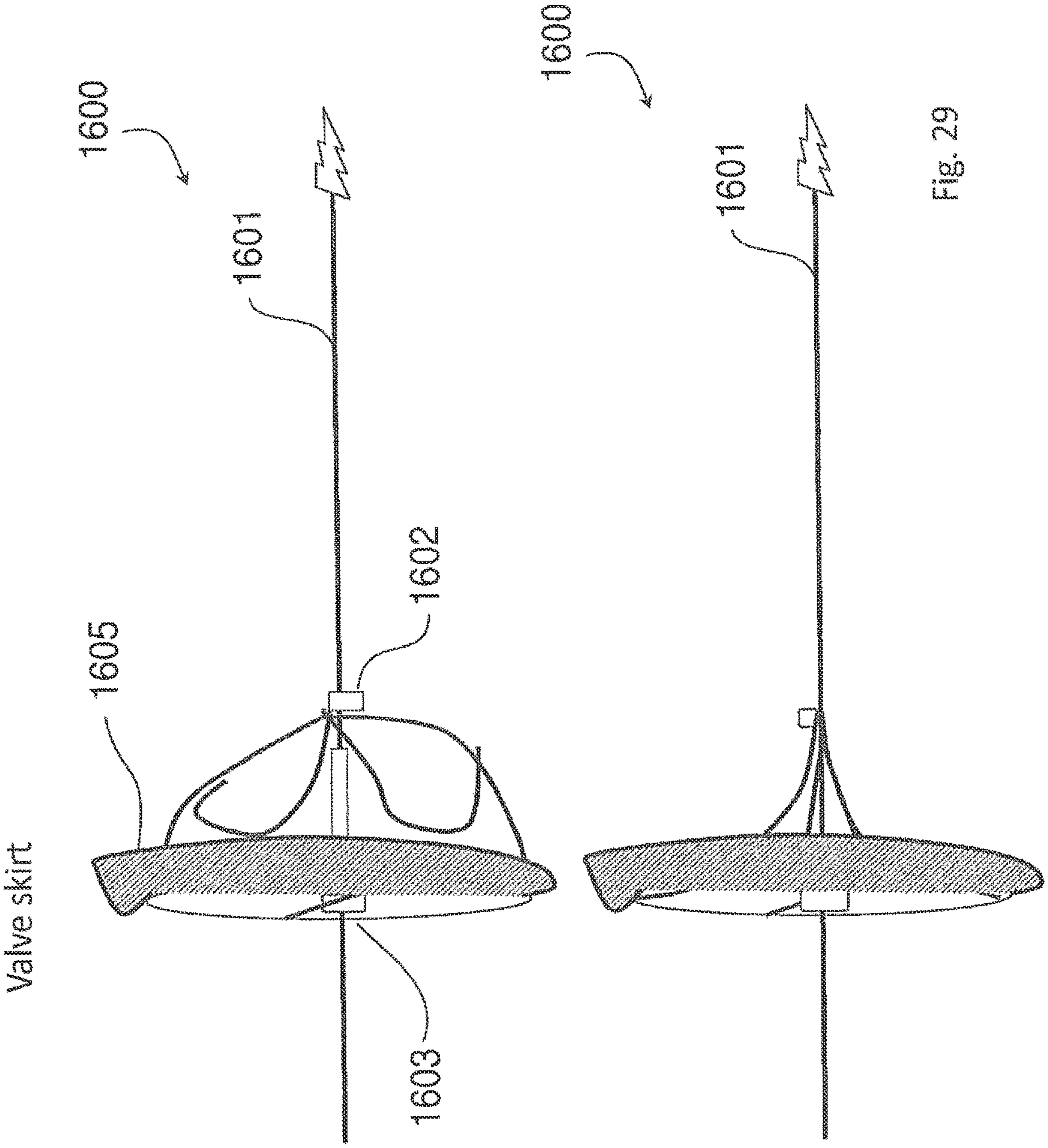
Figure 30:
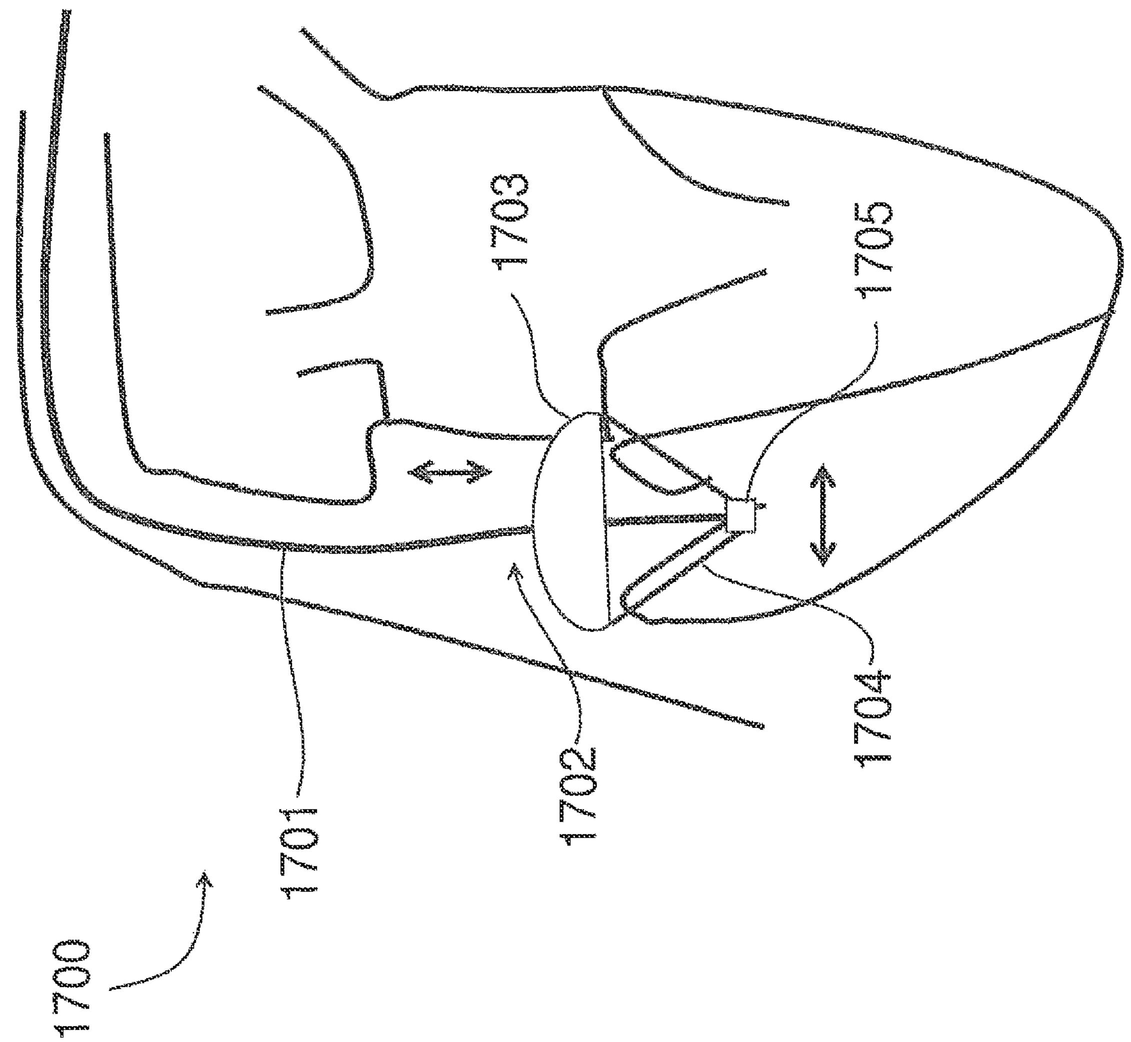
Figure 31:
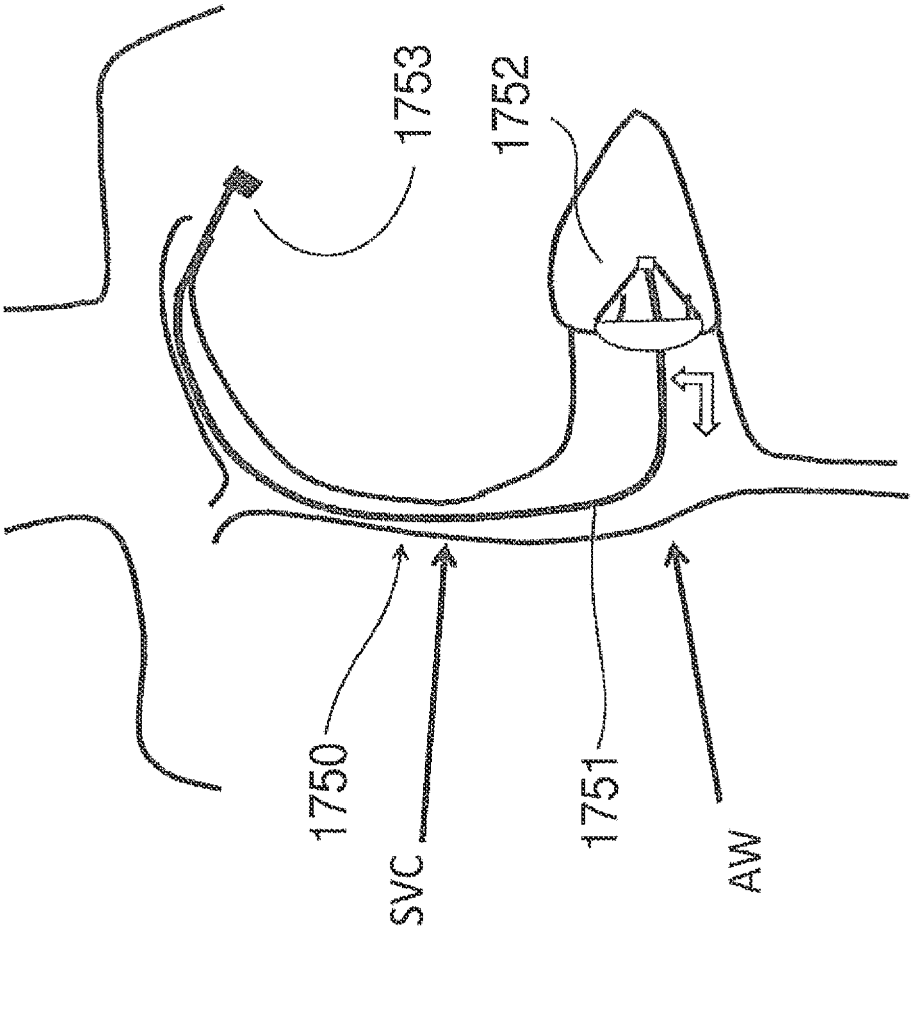
Figure 32:
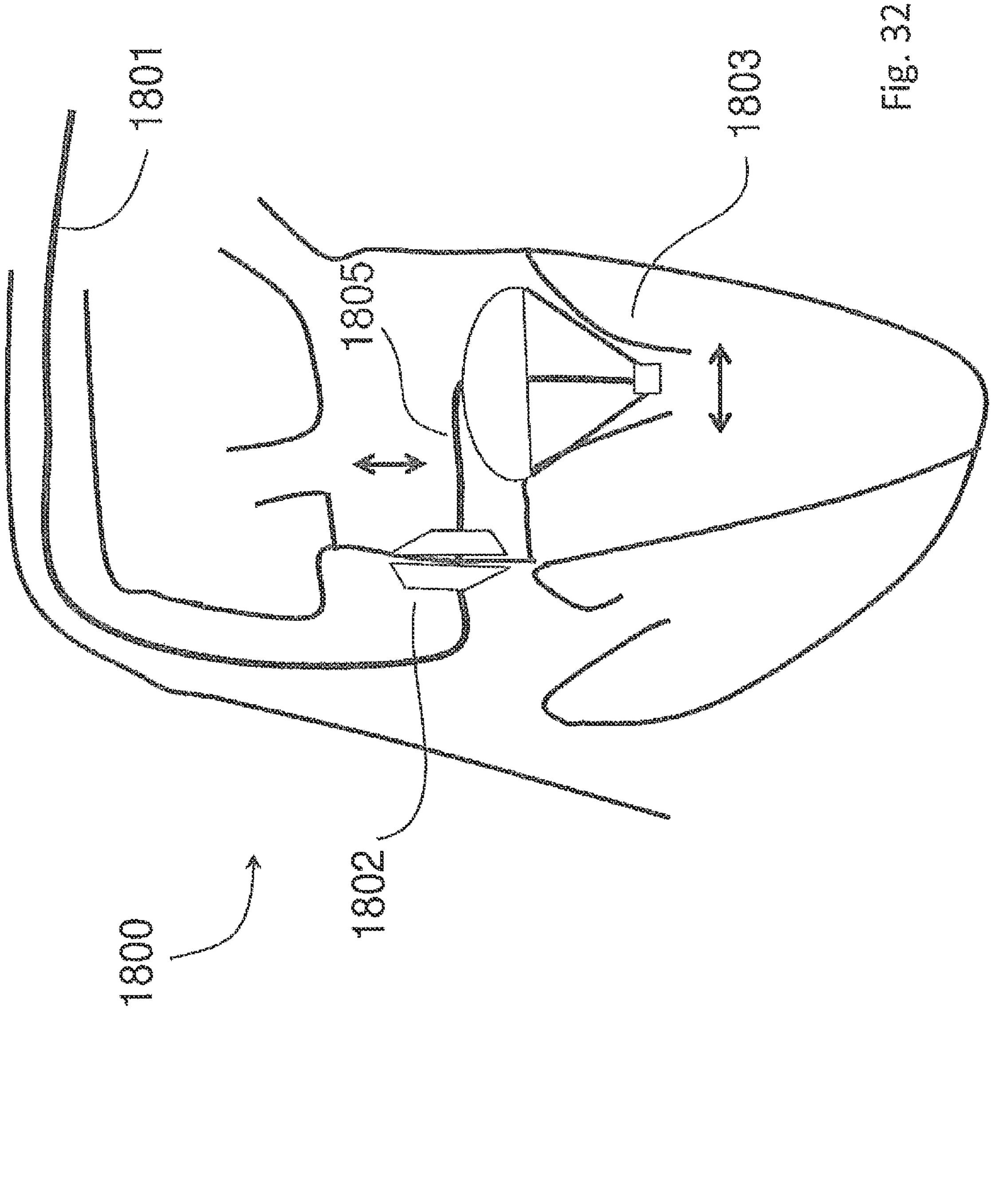
Figure 33:
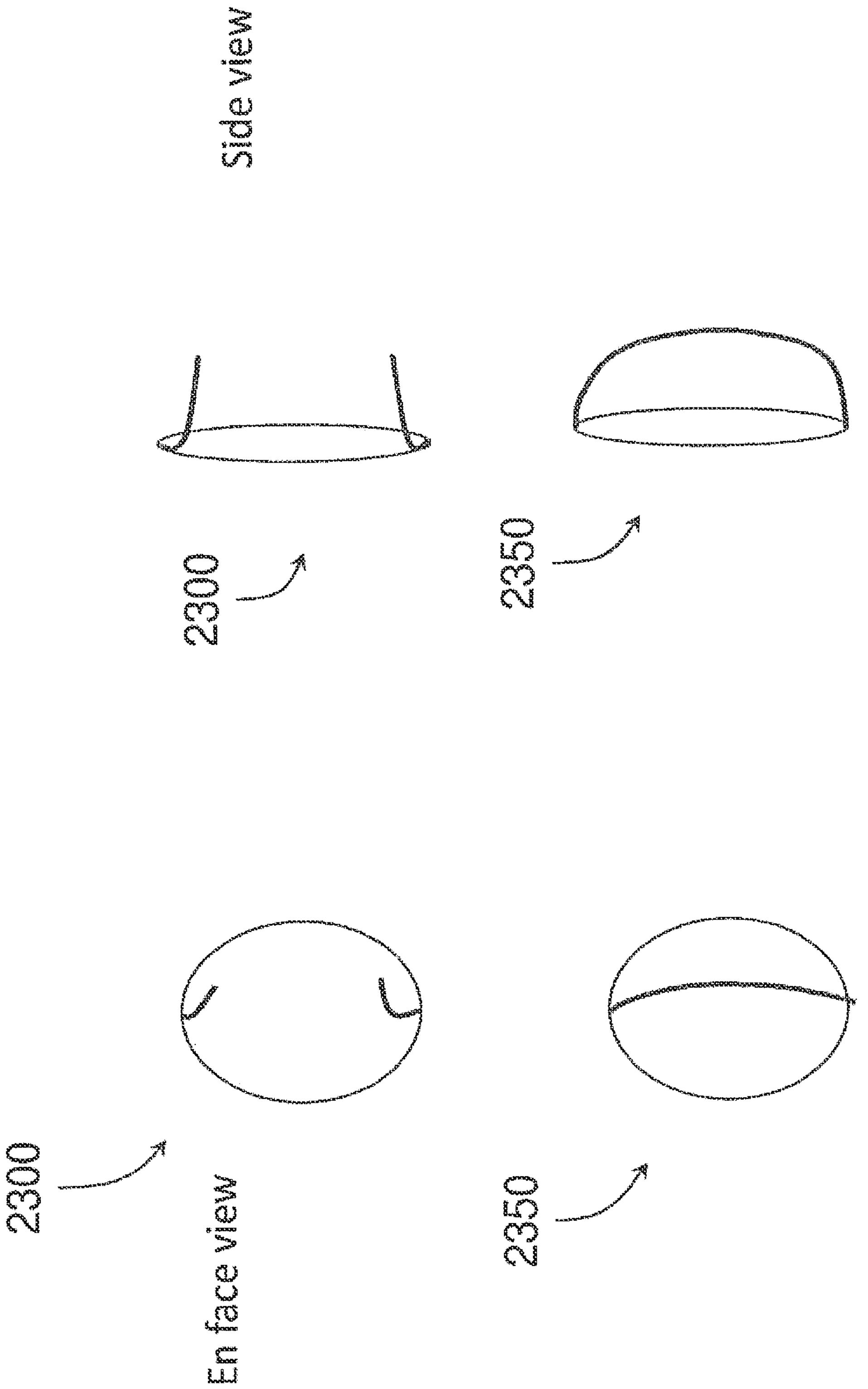
Figure 34:
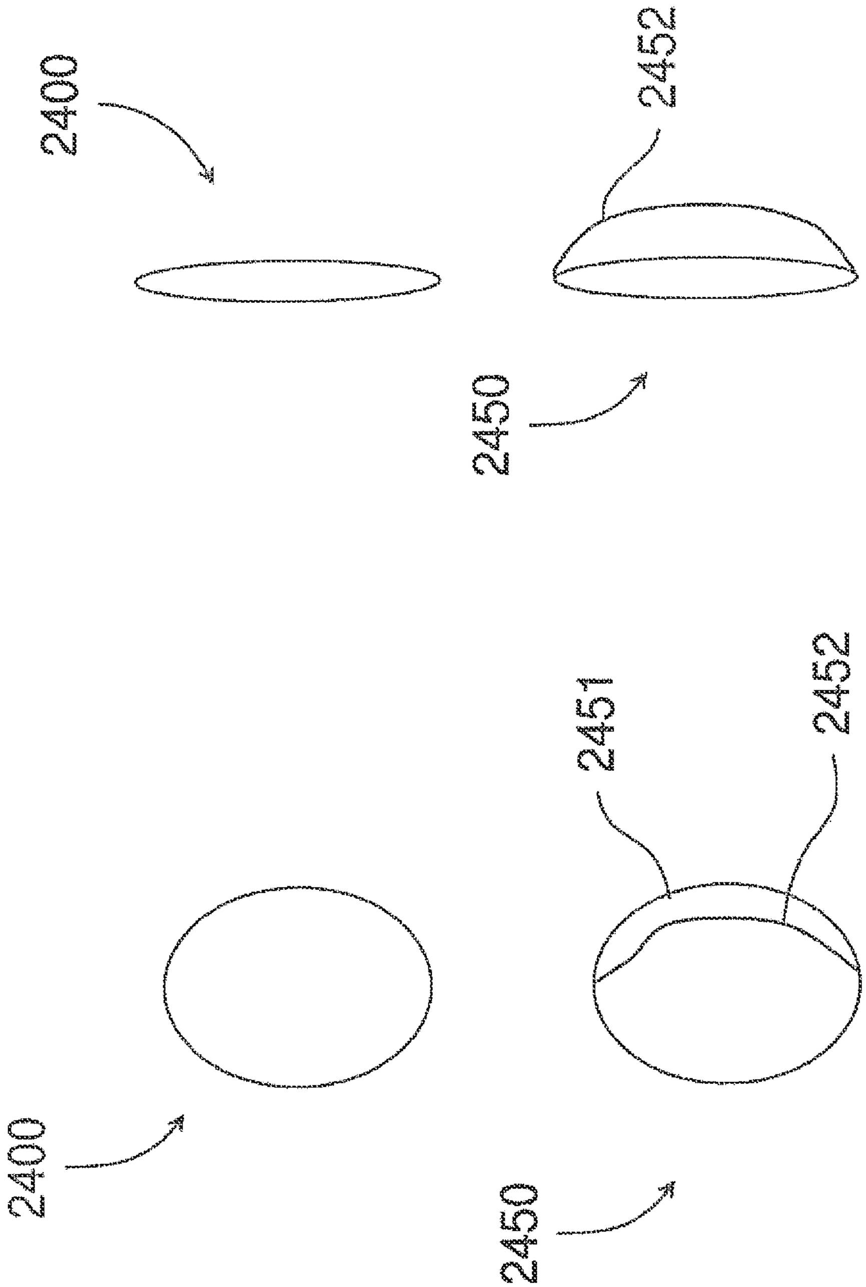
Figure 35:
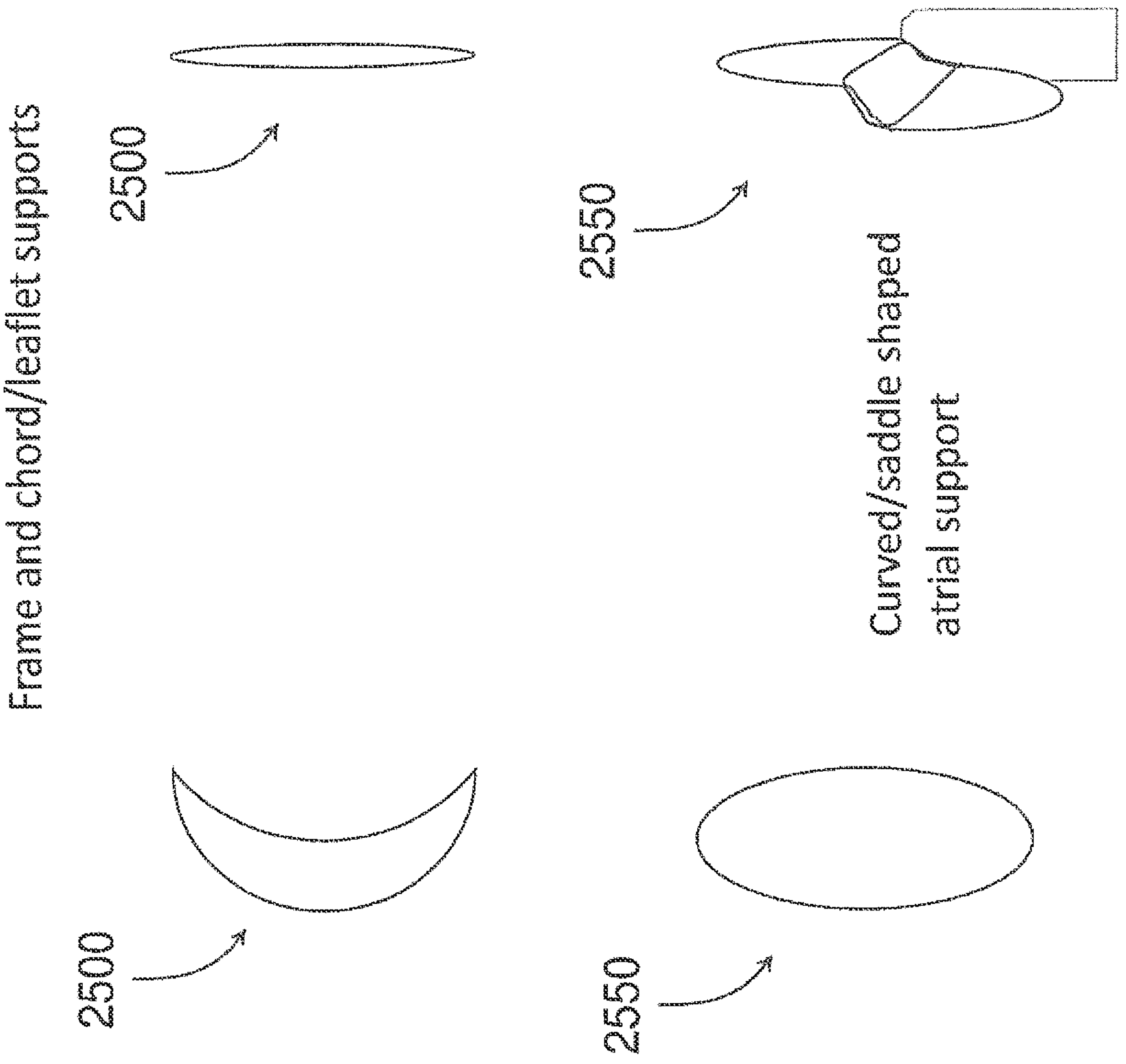
Figure 36A:
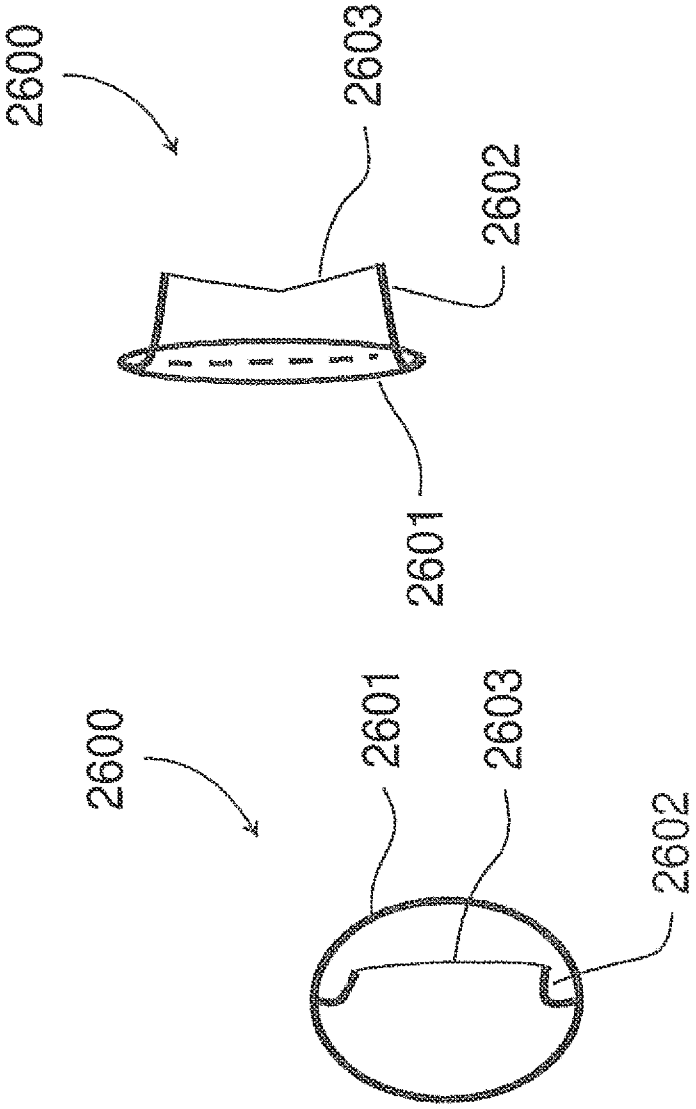
Figure 36B:
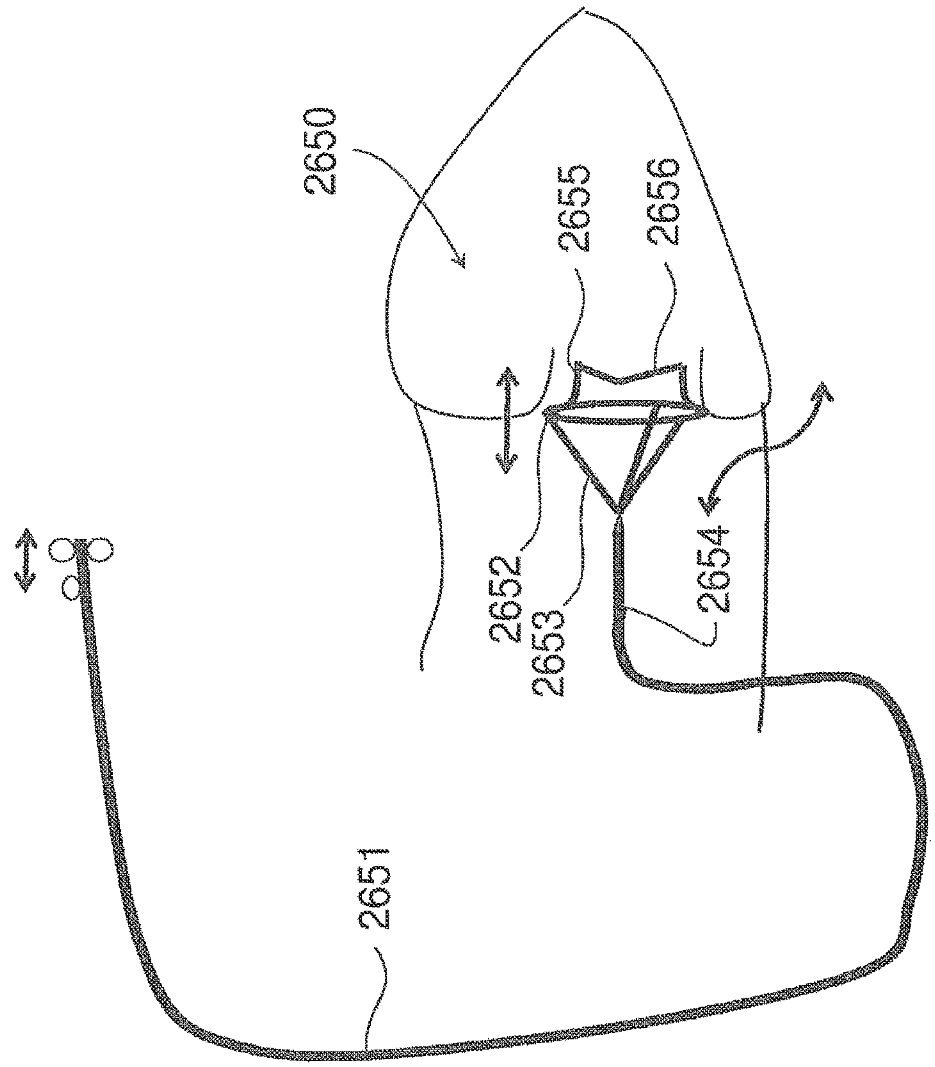
Figure 36C:
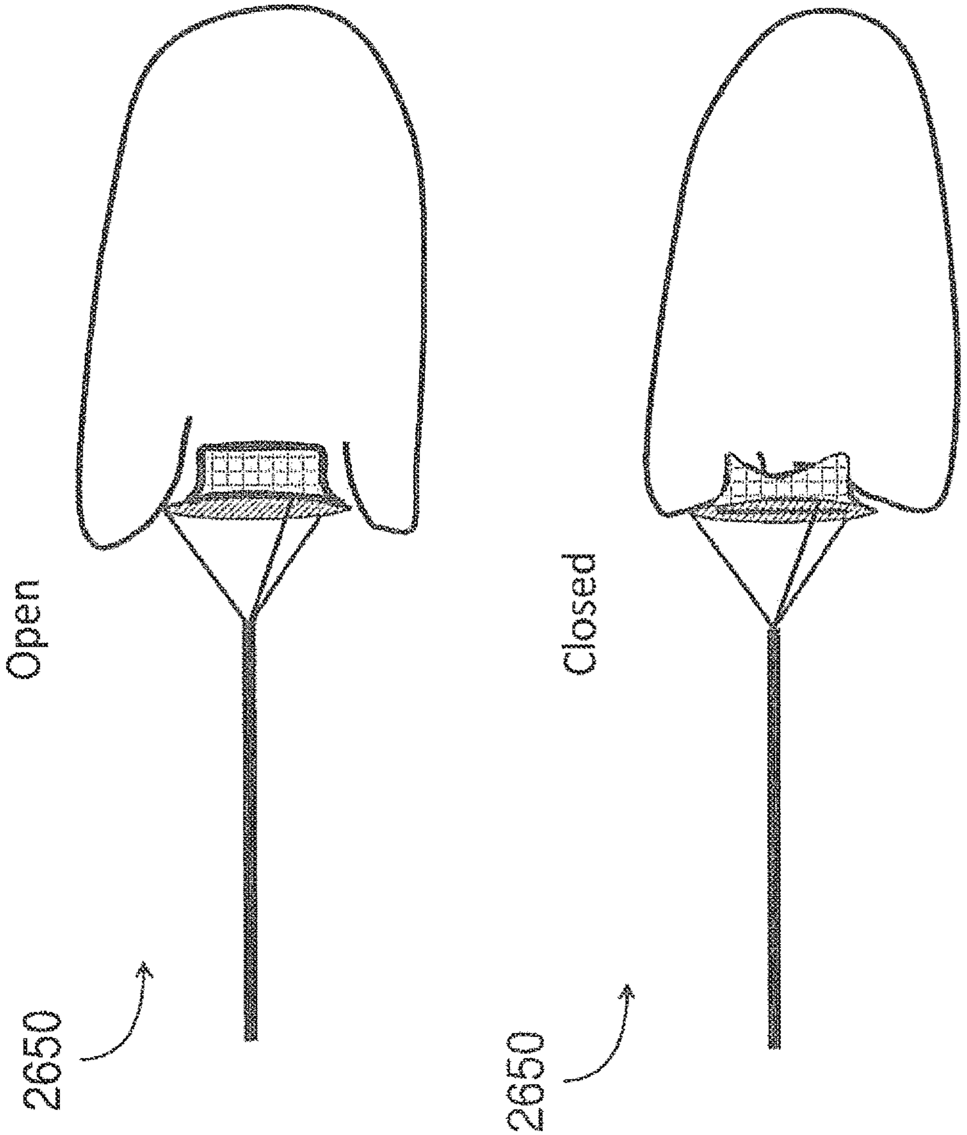
Figure 36D:
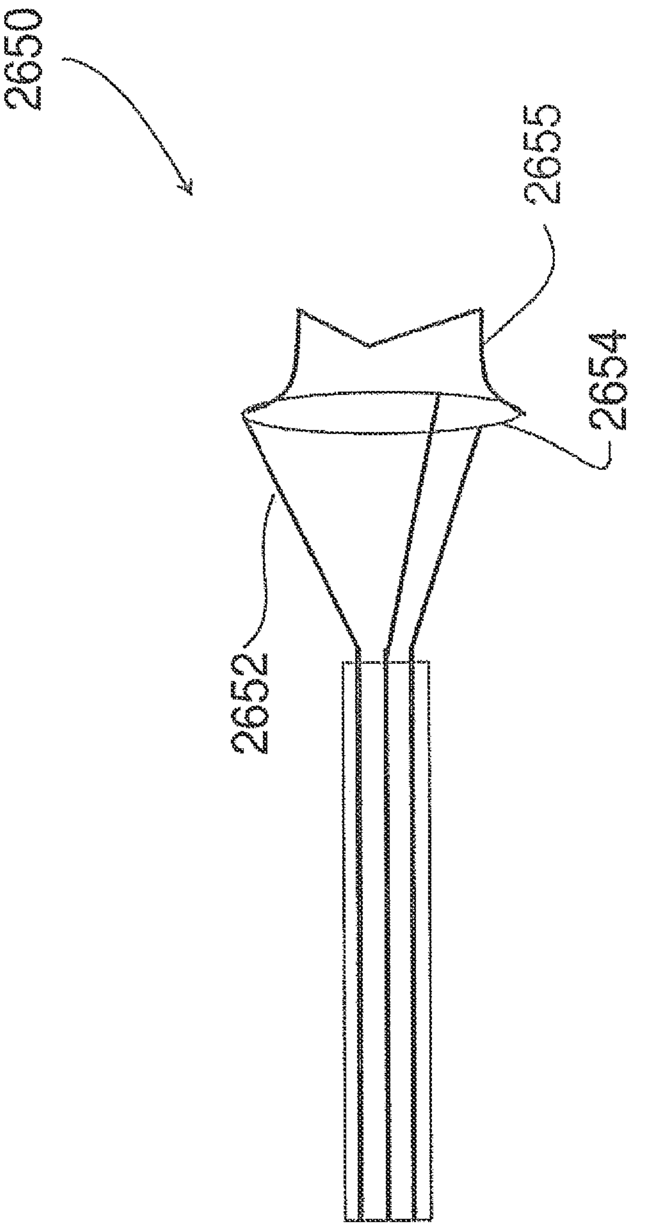
Figure 36E:
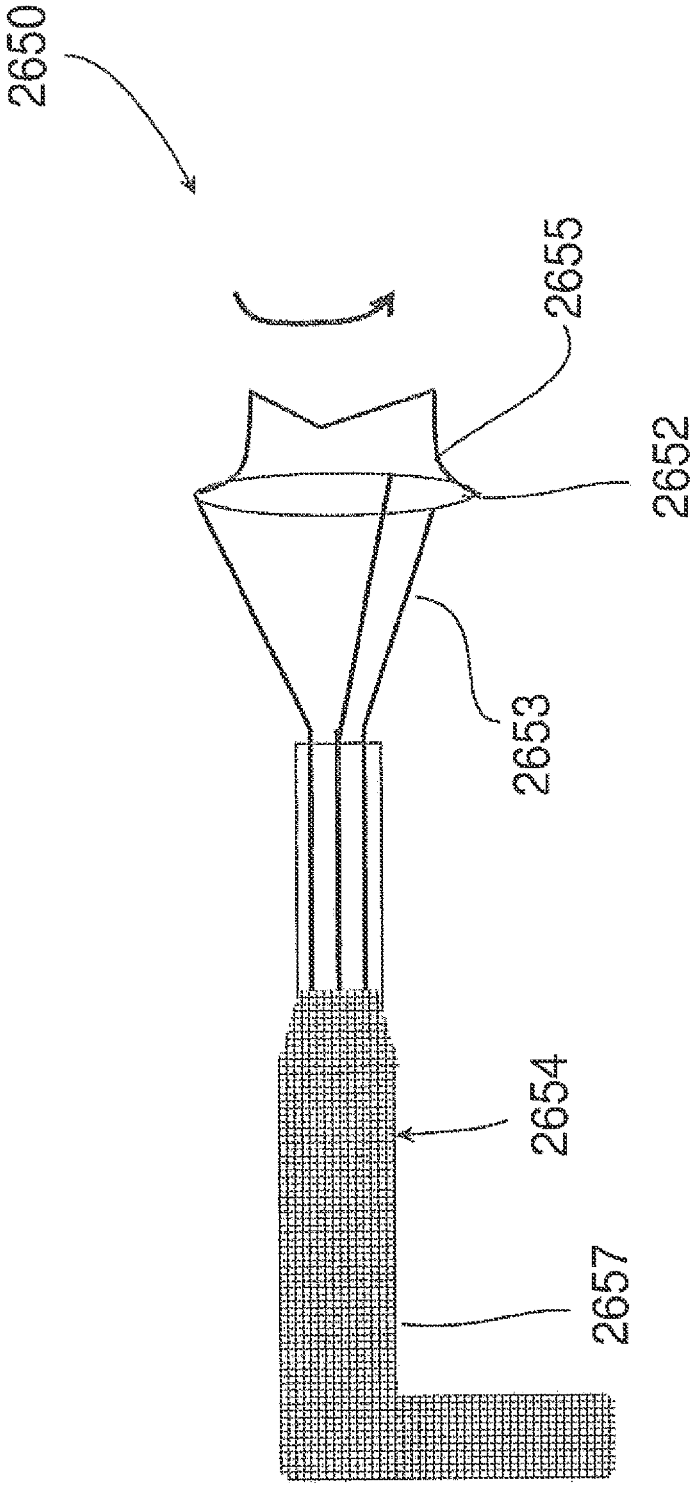
Figure 37:
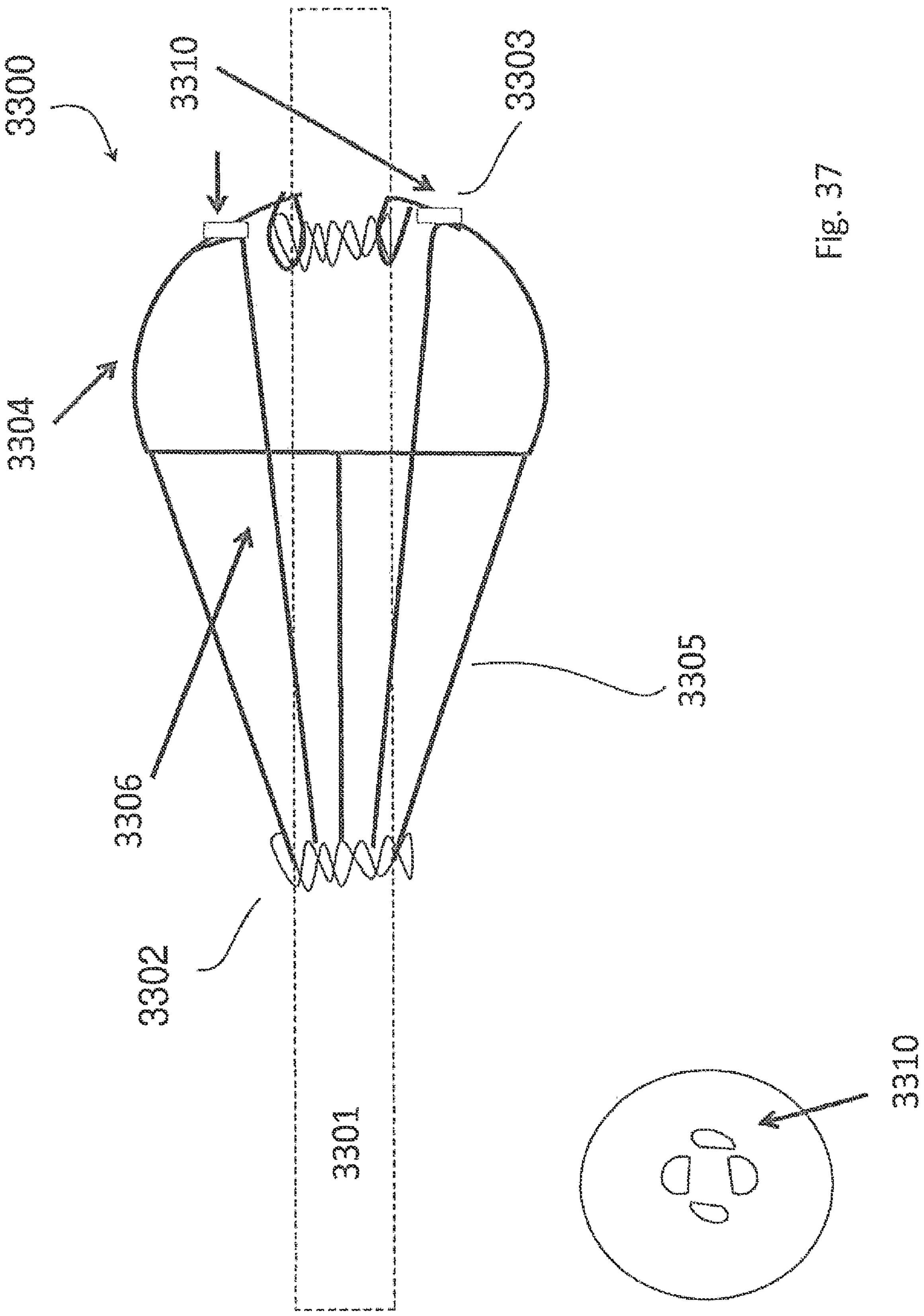
Figure 38:
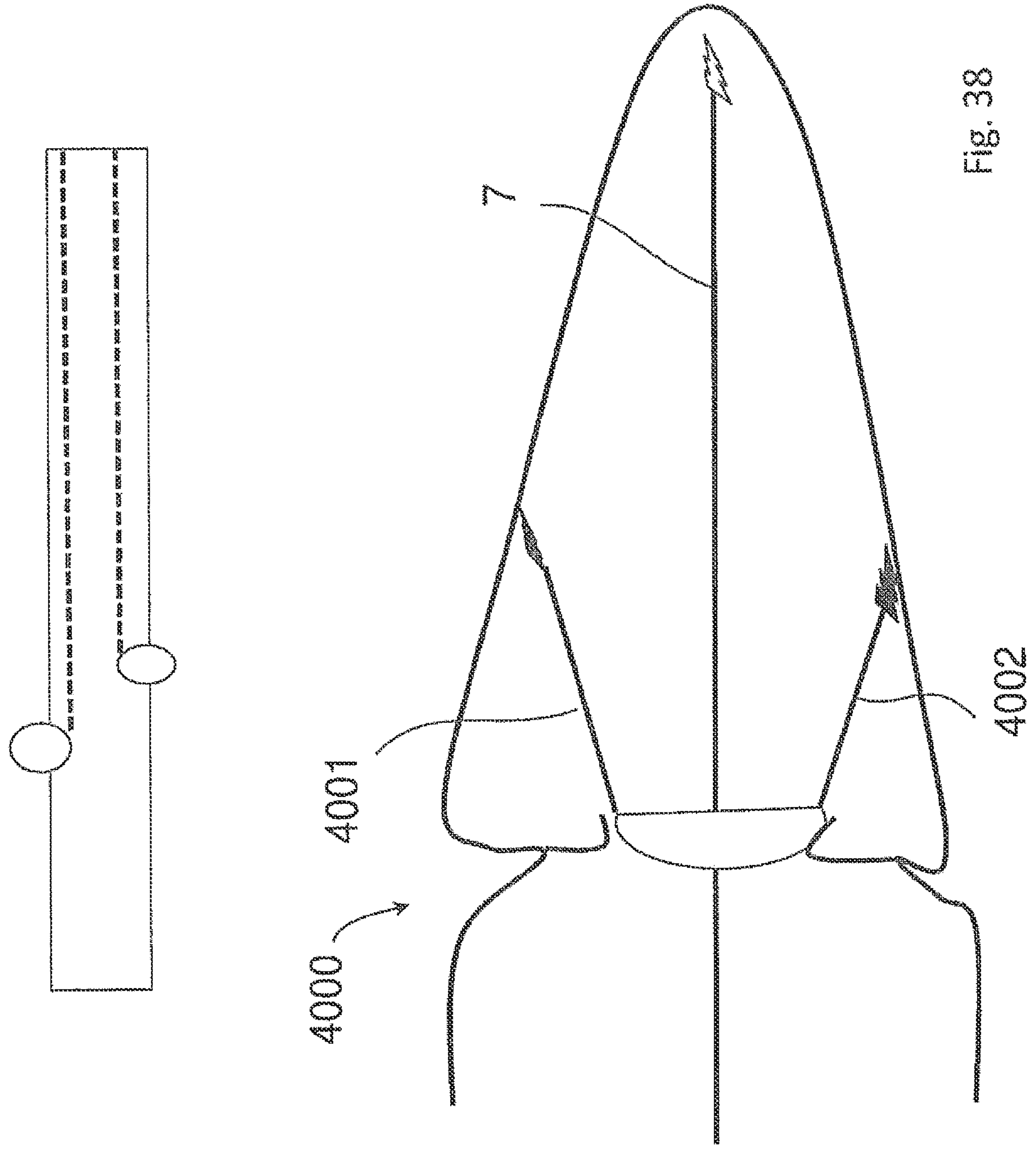
Figure 39:
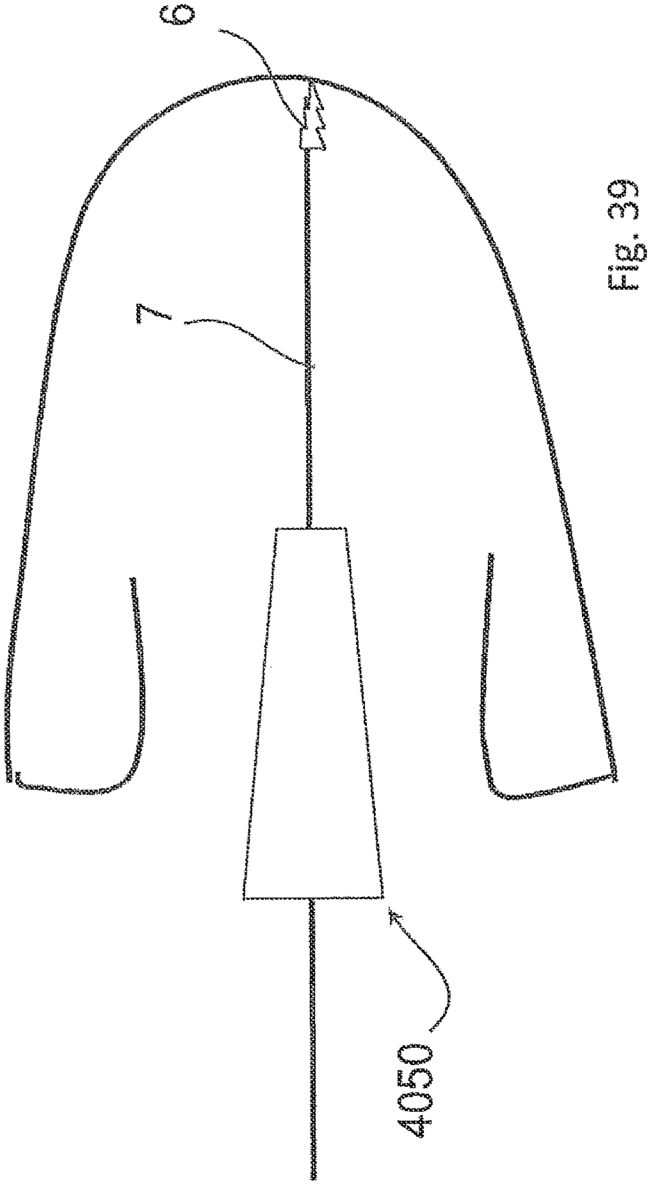
Figure 40:
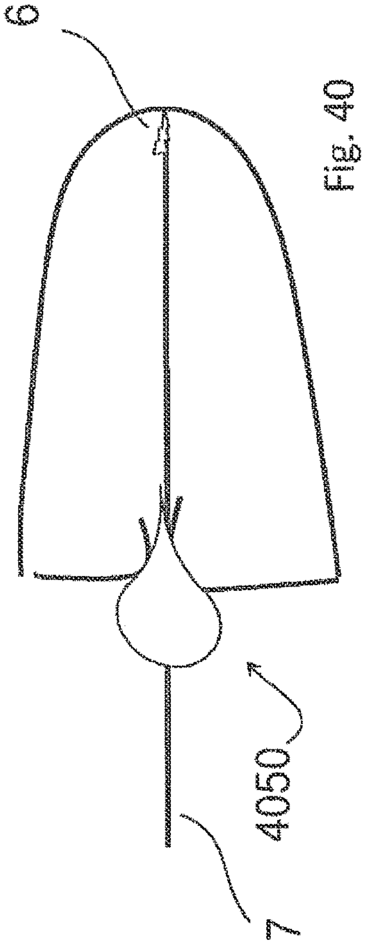
Figure 41:
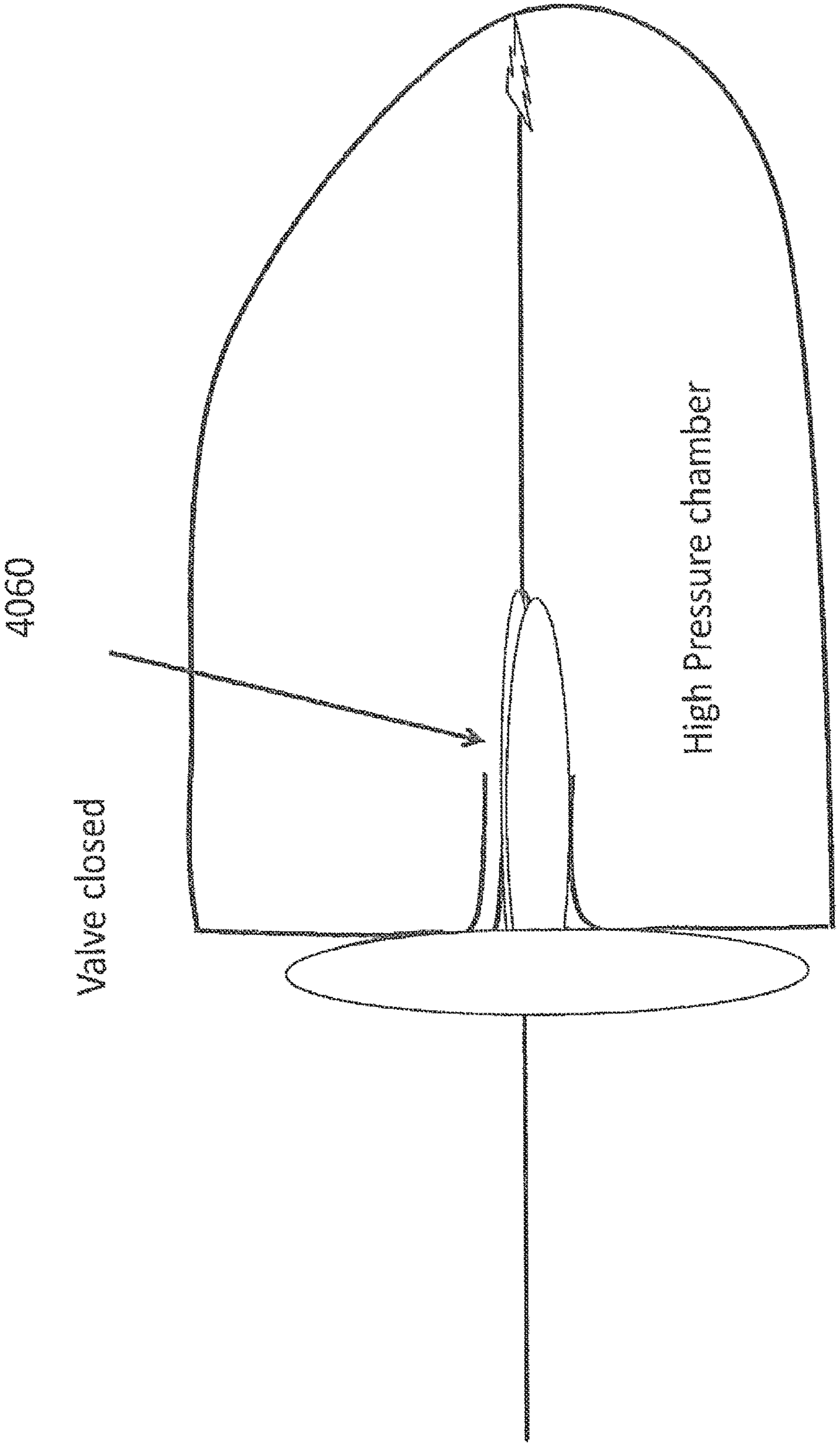
Figure 42:
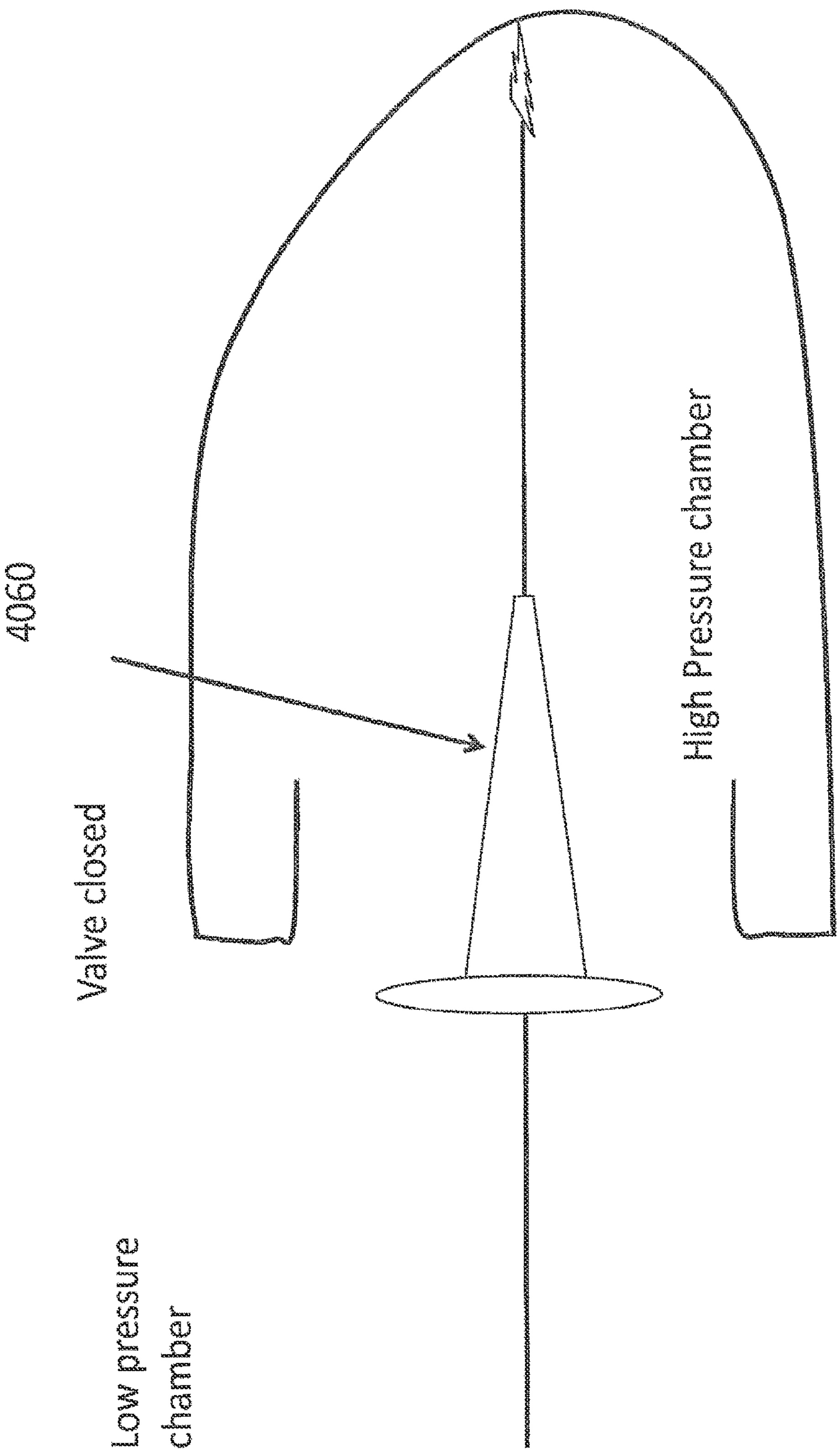
Figure 43:
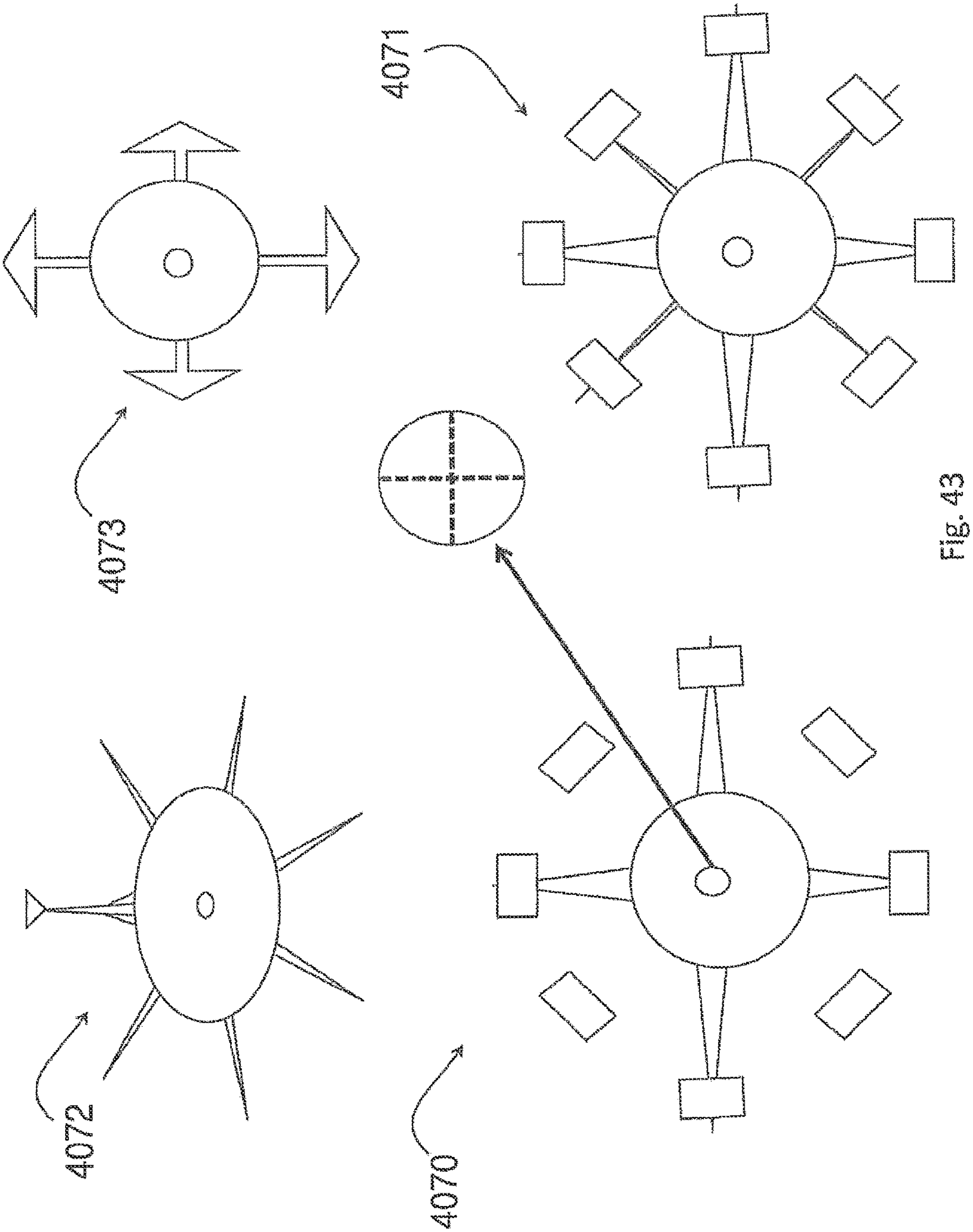
Figure 44:
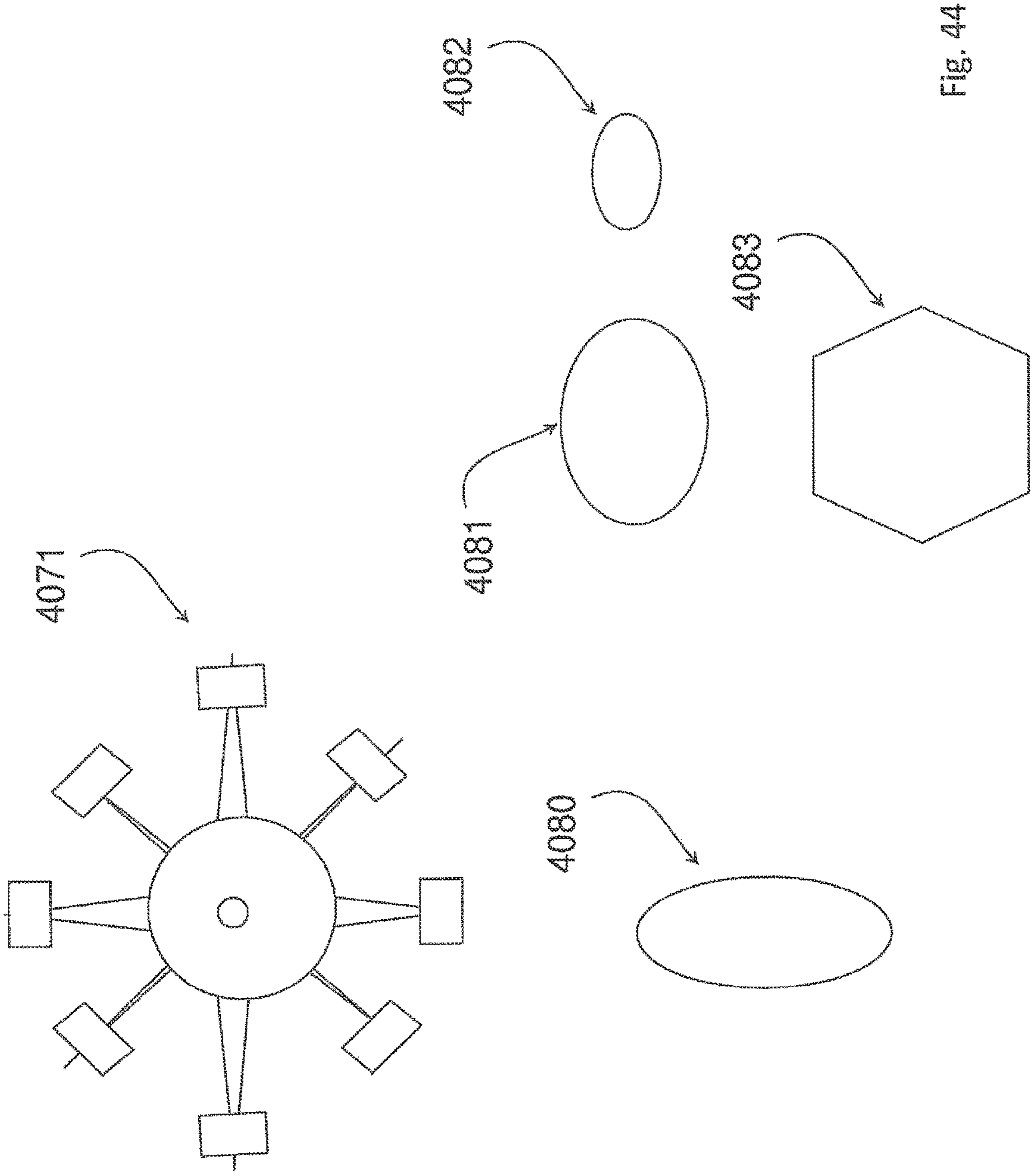
Figure 45:
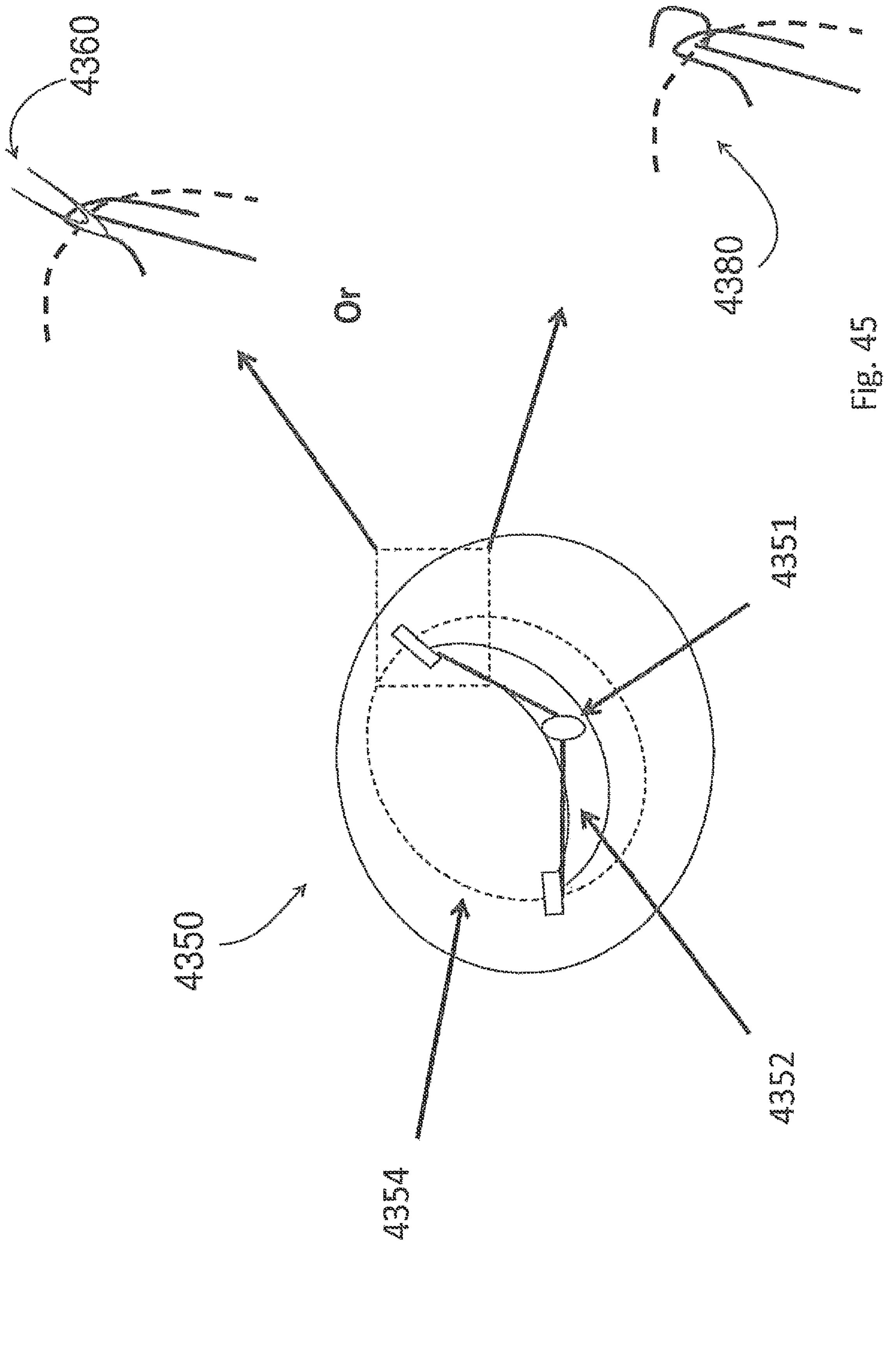
Figure 46:
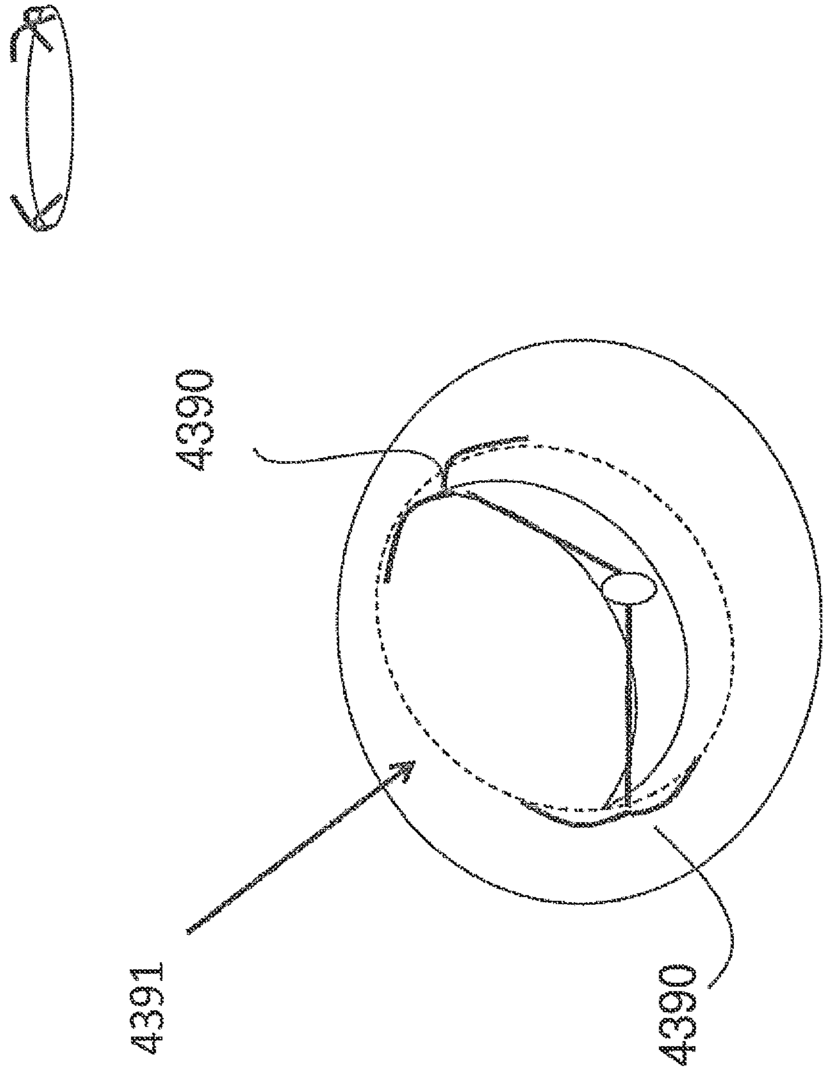
Figure 47:
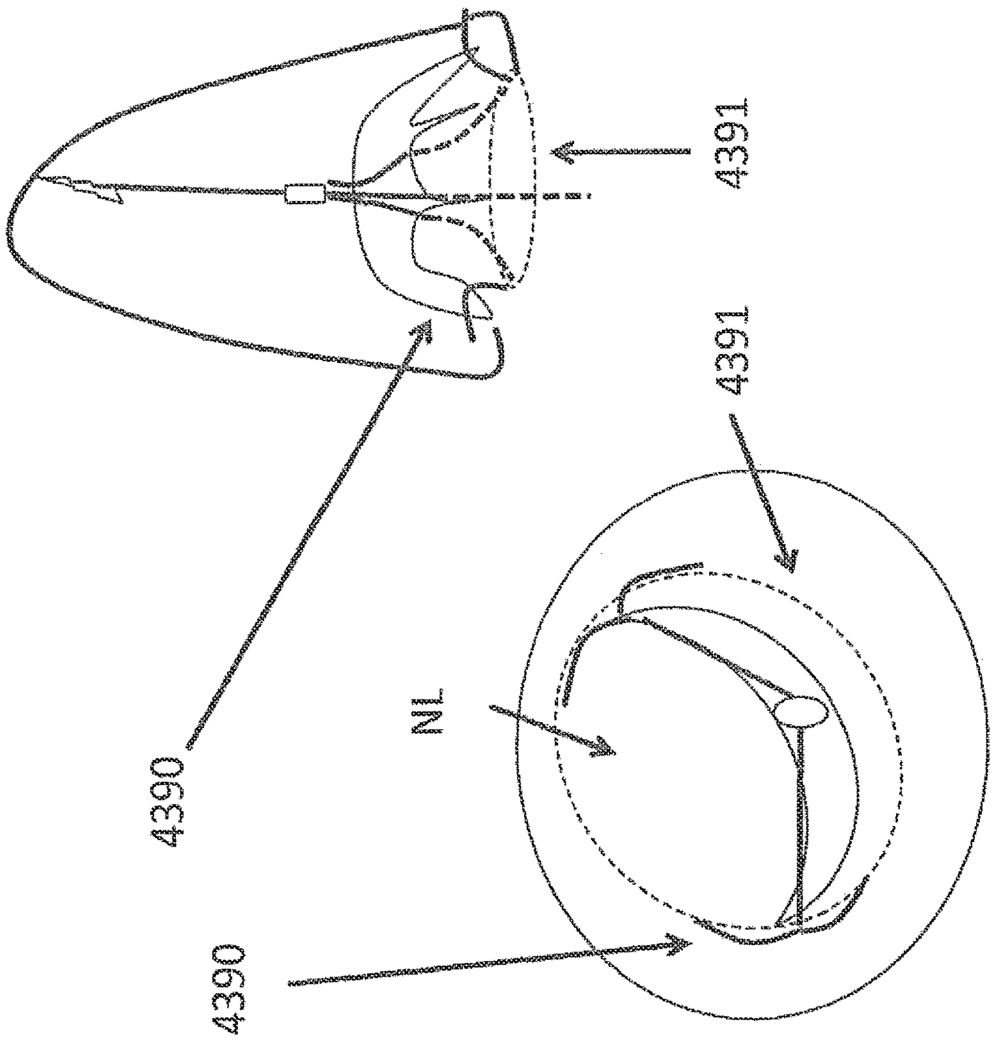
Figure 48:
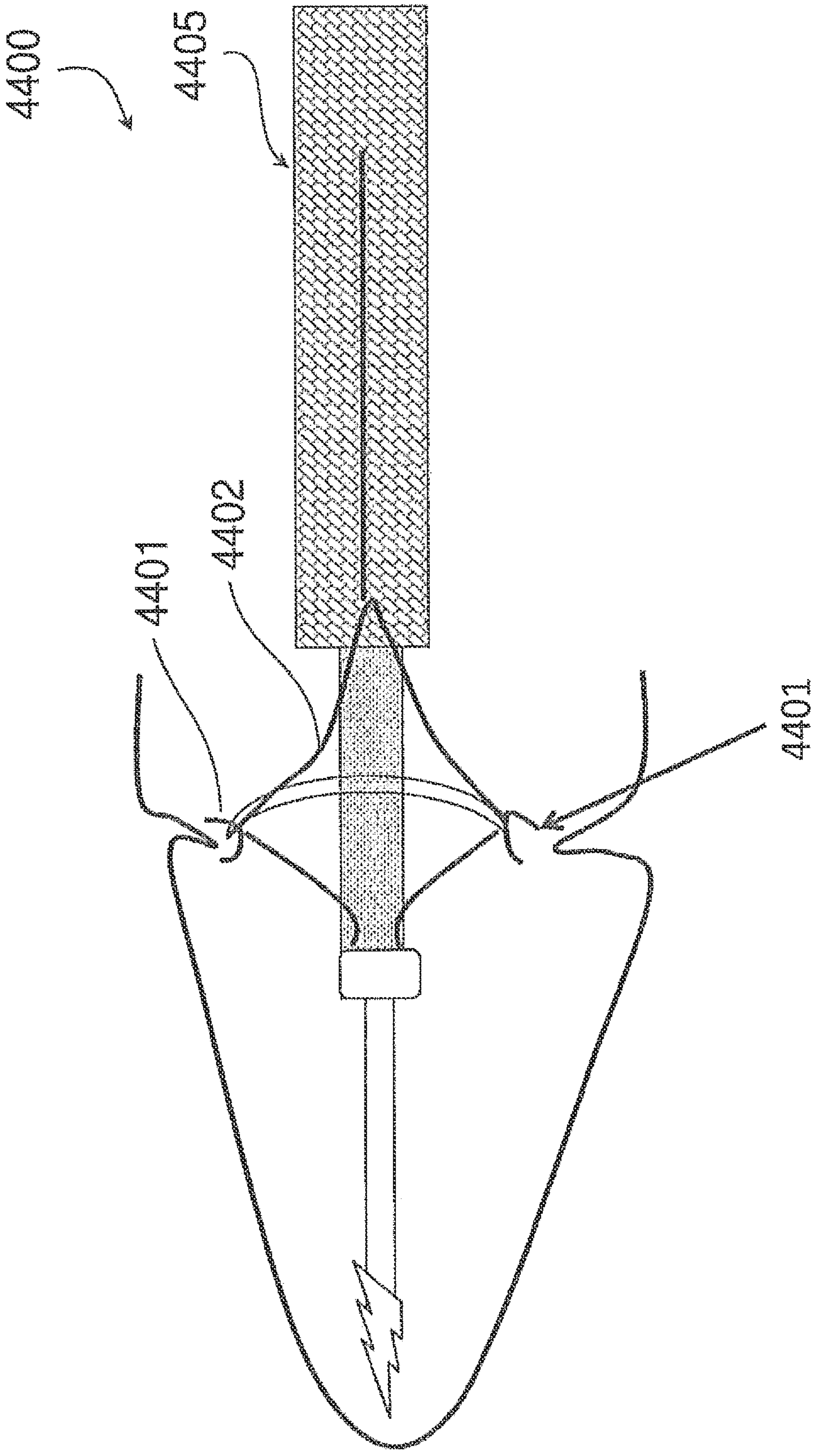
Figure 49:
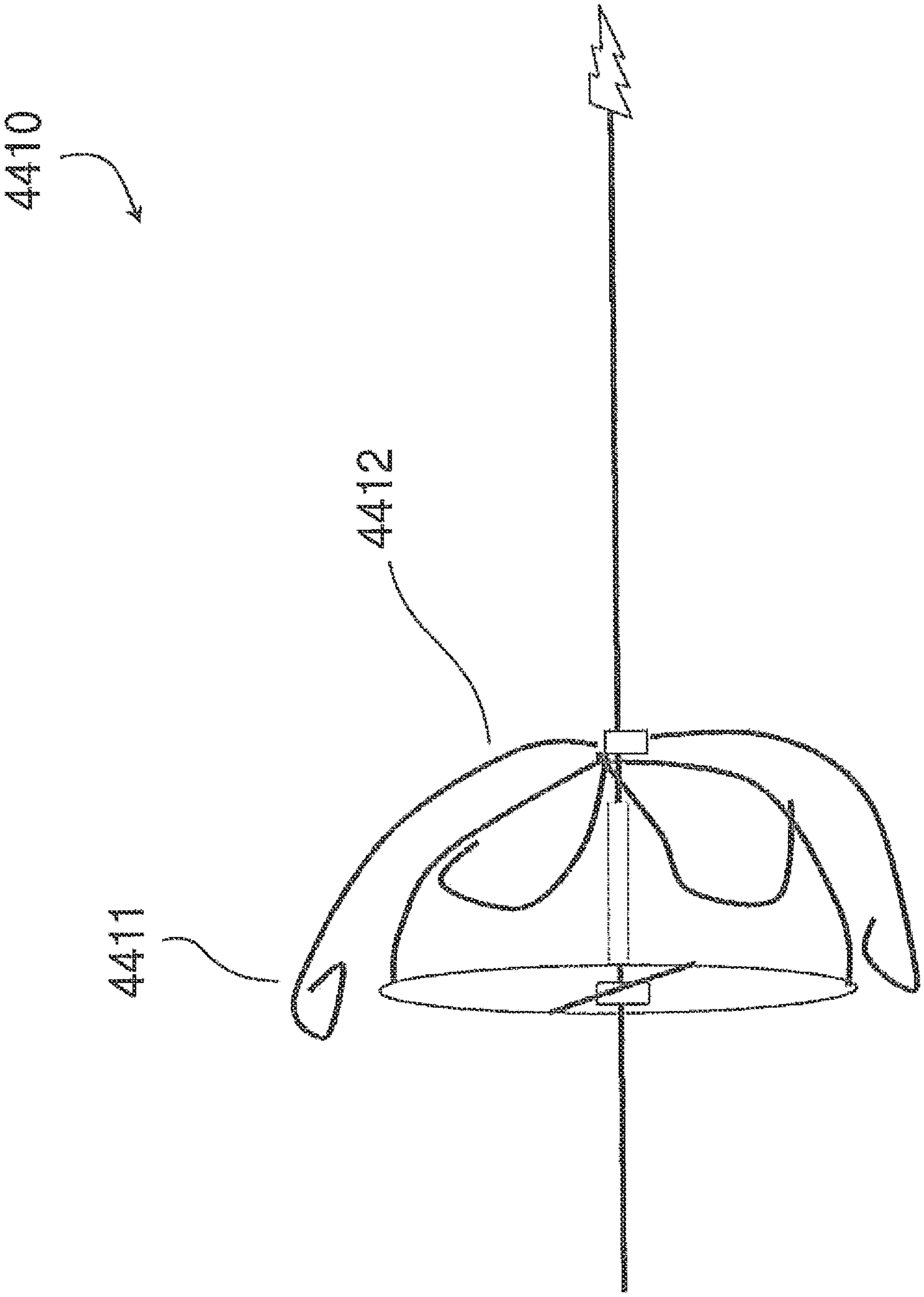
Figure 50:
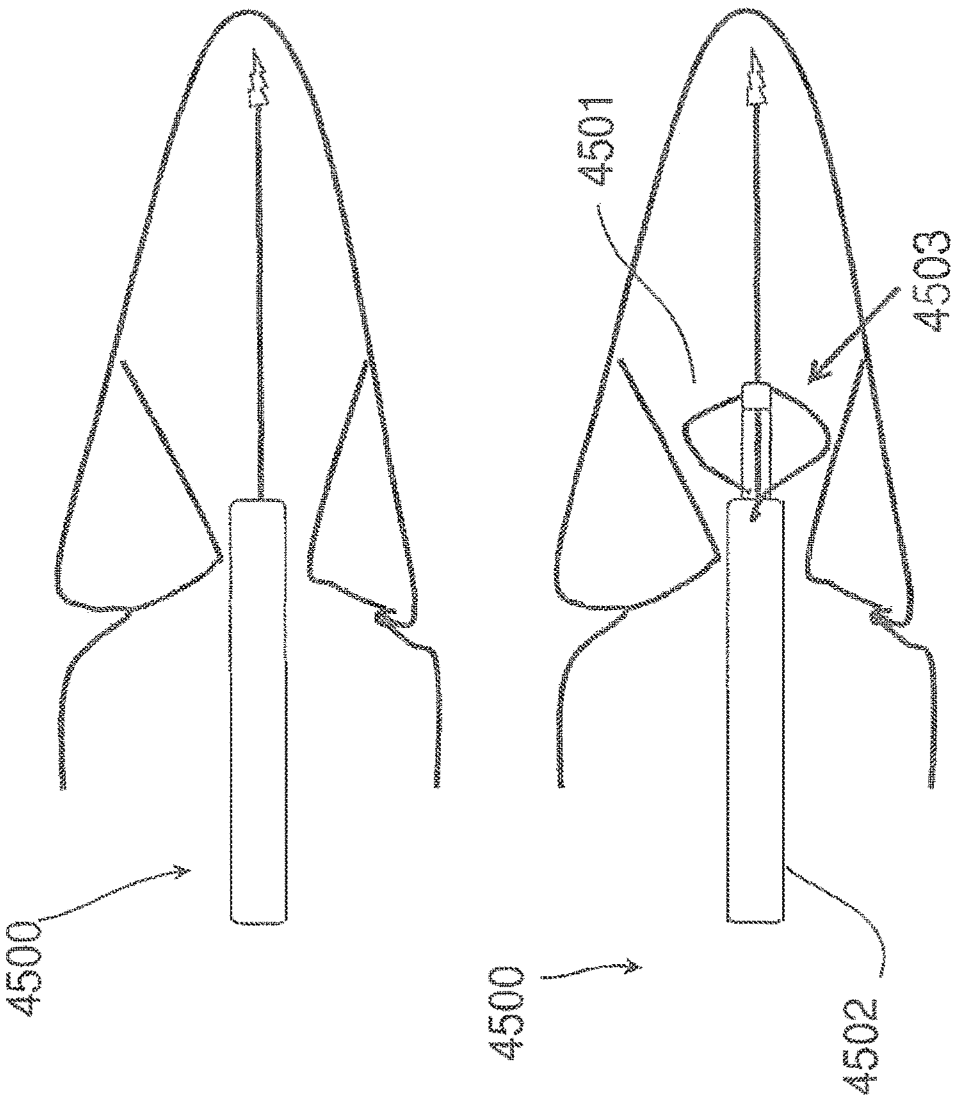
Figure 51:
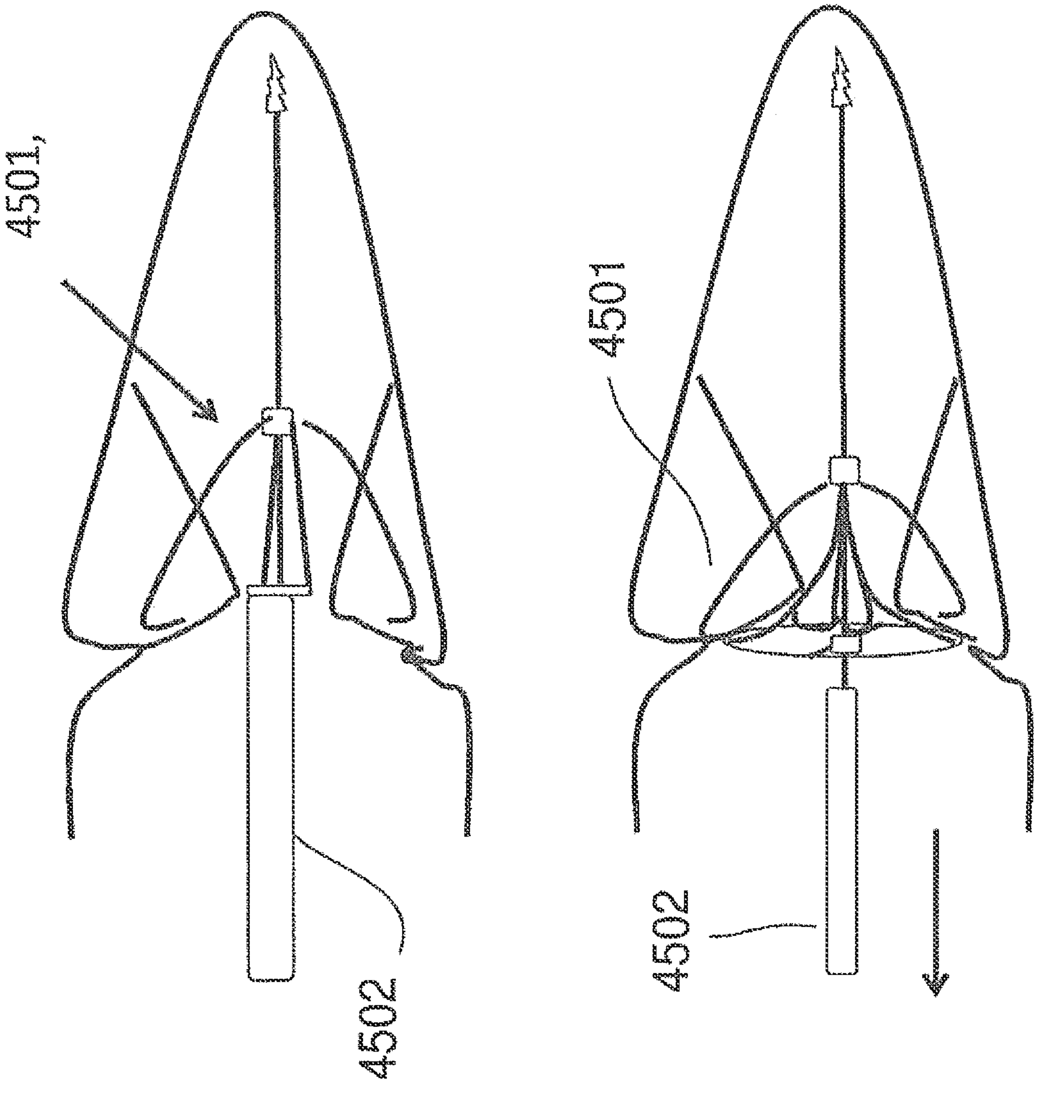
Figure 52:
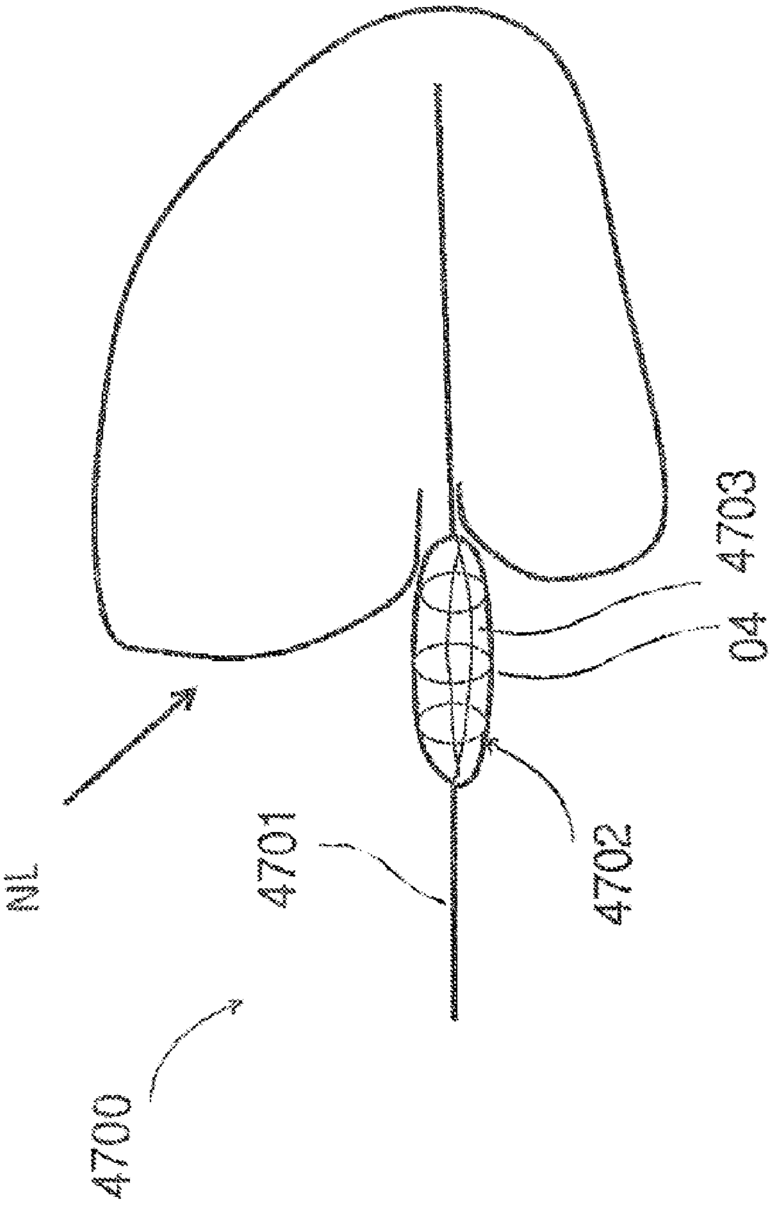
Figure 53:
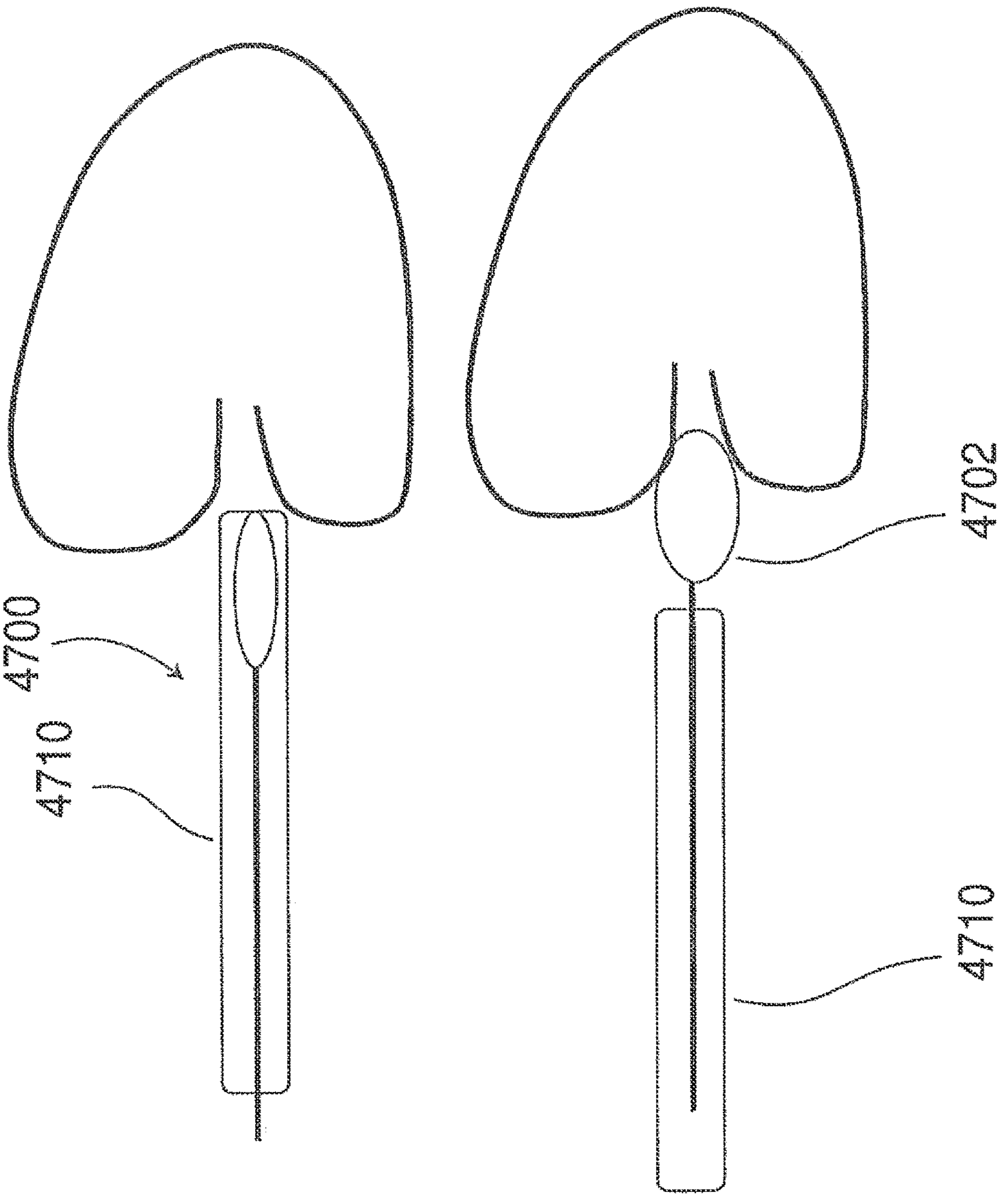
Figure 54:
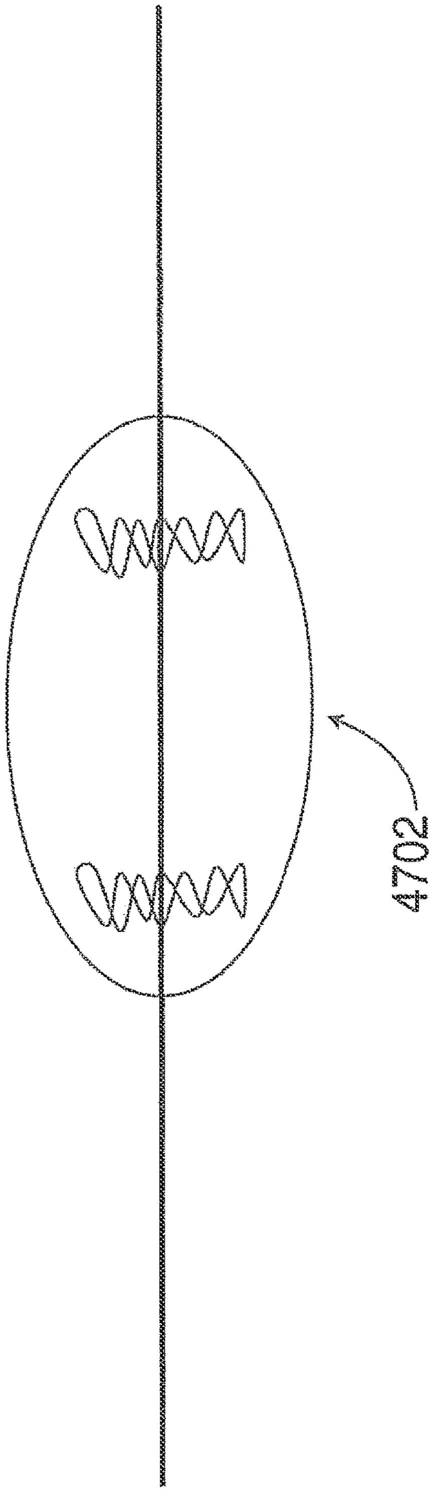
Figure 55:
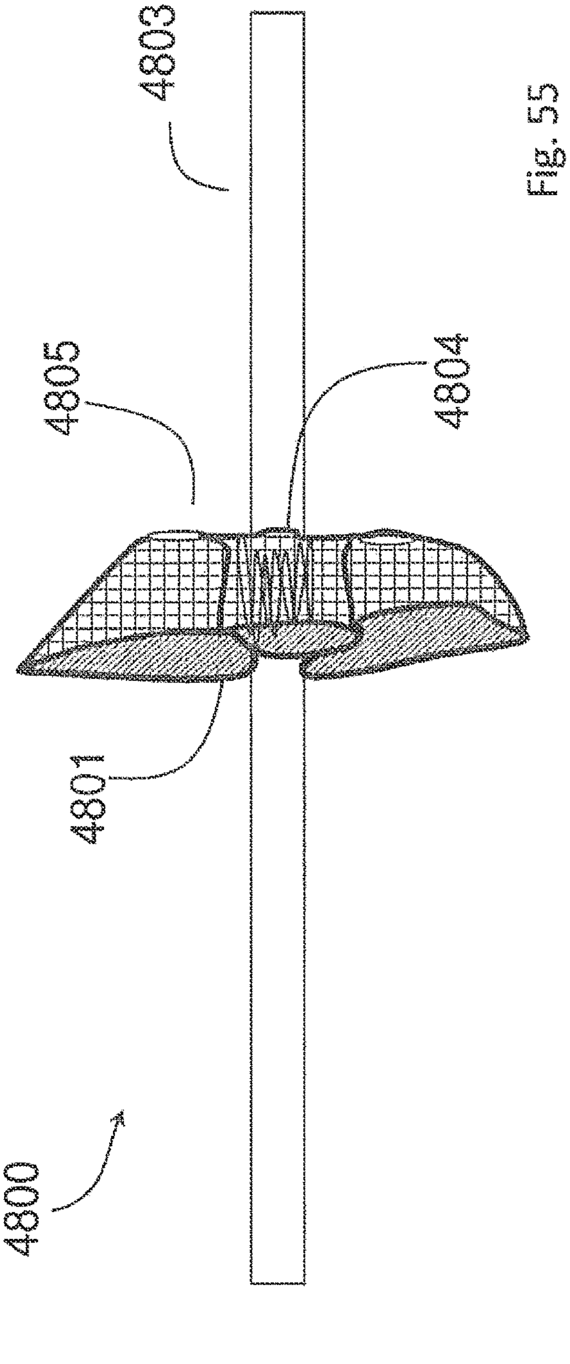

FIGS. 21(*a*) and 21(*b*) are diagrams showing an alternative prosthetic valve in which leaflets extend proximally and radially from a distal coupler for optimum co-aptation;

FIG. 22 shows another valve element with leaflets shaped to match the native leaflets and the orifice;

FIG. 23 is a pair of diagrams showing a valve element which can change orientation about a distal apex at which the anchor is terminated;

FIG. 24 is a set of diagrams showing alternative valve element leaflets;

FIG. 25 is a pair of diagrams showing a valve element having Nitinol or steel supports attached to a ring for engagement in the atrium side;

FIGS. 26 to 29 show devices which are variations of the device of FIG. 25, in open and closed positions, in which:

FIG. 26 is a pair of views of a device with a prosthetic valve in open and closed states, the valve having a support ring attached centrally to the anchor and the ring being arranged for engaging surrounding tissue for additional device support;

FIG. 27 shows this device in situ with the support engaging tissue on the atrium side and native leaflets co-apting against the prosthetic valve leaflets;

FIG. 28 is a pair of views of an alternative device in the open and closed positions, in which there is also a ring-shaped support and additionally this support has spring-loaded clamps on diametrically opposed sides of the ring, this being one example of fixation elements on the ring, alternatives being hooks or barbs; and FIG. 29 shows a device with an outer skirt attached to an atrial ring to prevent regurgitation;

FIG. 30 shows another device having a wire anchor without a fixing element, the anchor-being stiff and adjustable;

FIG. 31 shows a device which has a sub-cutaneous controller;

FIG. 32 shows a device in which a wire anchor has a variable distal end to change position of its prosthetic valve;

FIG. 33 is a set of views showing two valve elements, each having parts extending from a ring across the AV valve into the ventricle;

FIG. 34 shows further valve elements with atrium-side support rings, and FIGS. 35 and 36(*a*)-36(*e*) show further support shapes;

FIG. 37 is a side view diagram showing a device with fenestrations for allowing flow at the base of the leaflets and so help to prevent clot formation;

FIG. 38 is a diagram showing fixing of valve element chords to the wall of the heart;

FIG. 39 is a diagram showing a valve open element in a native state, and FIG. 40 shows forming of a valve-like structure;

FIG. 41 shows how an elastic shape conforms to shape of an orifice to seal between low and high pressure chambers;

FIG. 42 shows return of the elastic shape to its native shape;

FIGS. 43 and 44 show some examples of shapes for various valve elements as they are cut from material during manufacture, particularly parachute-type valve elements;

FIG. 45 is an AV enface view from the ventricle of part of the device of FIG. 28 in use, with a ring on the atrial side and showing a magnified view of a spring-loaded clamp, and a similar view of an alternative fixation device in this case a Nitinol hook configured to engage surrounding tissue on the ventricular side;

FIGS. 46 and 47 are views, also from the ventricular side, showing an alternative pair of diametrically opposed fixation devices, in this case on radial aims or spokes and configured for engaging on the LV side, while a ring engages on the atrium side;

FIG. 48 is a side view of a device being delivered by a catheter so that the fixation devices on a ring are correctly positioned at the AV groove;

FIG. 49 is a side view of a device with fixation devices on support aims to support the device against the force of the blood being pushed back into the atrium, and thereby adding additional support to the anchor screw;

FIG. 50 is a pair of views of a device with strut-like supports being delivered, and FIG. 51 shows the supports in place;

FIG. 52 shows a valve insert having a Nitinol frame with a skin cover, in this case of pericardium, FIG. 53 shows delivery of the valve, and FIG. 54 shows details including clamping of the valve to the elongate support by way of Nitinol springs; and FIG. 55 shows a valve insert without chords.

DESCRIPTION OF THE EMBODIMENTS

A heart valve therapeutic device has a prosthetic valve insert or element which is positioned on an elongate anchor having a longitudinal axis at a desired axial position on the anchor during delivery. The valve element positioning on the anchor is set by the surgeon using an actuator at the proximal end of the anchor. The terms “valve insert” and “valve element” are used in this specification to mean the therapeutic element which is inserted into the AV area to assist the native valve leaflets or in some cases function closer to or as a full valve where the native valve is considerably damaged. In the latter case it may be referred to as a “prosthetic valve”.

In various embodiments, we describe a device with a valve insert to reduce regurgitation, that is inserted through a blood vessel on a deflectable support that may or may not be fixed to the heart wall. The shape and position of the valve insert and of the support can be altered and the support acts against the force pushing the valve insert back into the atrium. The valve insert is designed to allow the native leaflets to continue to move and co-apt against the surface of the valve insert.

Stiff stylets or outer cover/catheter may be employed to stiffen the anchor to support the valve element against the heart wall or atrial septum, and this arrangement may avoid need for fixing to the heart tissue. A deflectable and/or lockable catheter with inherent stiffness may be used to maintain the valve element in position. The catheter is adjustable post-implantation through motorized controls implanted under the skin at the point of exit of the catheter from the vein.

There may be a part of the support which fixes to the heart tissue in the atrium, such as a ring which engages the atrium adjacent and around the AV valve. Hooks may attach to the atrial ring and support the valve from the commissures or the ventricular side of the valve. The valve element may be fixed to the distal end of the anchor, and this may be at a universal-type joint allowing it to pivot or rotate to adjust to the movement of the heart native leaflets.

The support in several embodiments comprises an elongate anchor which extends through a blood vessel and is left in situ, being sutured in some embodiments at a proximal location such as in the shoulder area. It is supported by engaging the heart wall such as by a barb or other fixing element at its distal end, and/or by its inherent stiffness. In the latter case the atrial or vessel wall can provide support at a bend in the anchor. A stylet or collar may be provided to slide along the anchor to provide a desired shape at the valve element and also a desired position.

The position of the device on the anchor may in some embodiments be changed after delivery. Moreover, in some embodiments, the orientation and/or radial/longitudinal position of the valve element may be adjusted either during delivery or afterwards using controls at a proximal end of the elongate anchor.

Advantageously, the position and orientation of the device is not fixed by the requirement to affix it directly to the heart using a tether and fixing element such as a barb or screw, this being avoided by stiffness and locking of the anchor, possibly using support from the atrium wall.

The valve element may have any of a variety of configurations. If the defect is large it may be of the parachute type, operating like a fully-functioning valve. If the defect is not large the valve element may have leaflets or a closed body with a shape suitable for the native valve leaflets to co-apt against it. In some such embodiments, it merely prevents on-axis retrograde flow. Importantly, the invention allows adjustment of axial position of the valve element, and in some embodiments orientation of the valve element on the elongate anchor. This allows the surgeon to achieve optimum position of the valve for its purpose.

The surgeon has visibility of the position of the device during surgery by virtue of a combination of known techniques such as an echo cardiogram and X-ray equipment for visibility of metal parts of the device.

Advantageously, the device may be incorporated in a pacemaker lead, in which case the anchor forms the elongate body of the pacemaker lead, and supports both die valve element in the AV region and the pacemaker electrodes.

Referring to Fugs. 1 to 6 a percutaneous heart valve treatment device 1 is shown at a general level. The device 1 comprises a first sheath 2 with a distal end 3 which is deformable because it has a pulley system within its core which flexes and extends the distal end of the sheath by rotation of the proximal handle.

A proximal handle 4, comprising a haemostatic valve through which the guide wire passes, is used by the surgeon to route the first sheath 2 along the superior or inferior vena cava (SVC). At the end of the travel the sheath distal end 3 crosses the tricuspid or mitral AV valve ("AV") and into the right or left ventricle as illustrated. The guide wire is removed and the sheath is orientated towards the ventricular wall below the level of the defect in the AV valve. FIGS. 1 to 6 show the AV valve denoted "AV", and the atrial wall as "AW".

Figure 15:
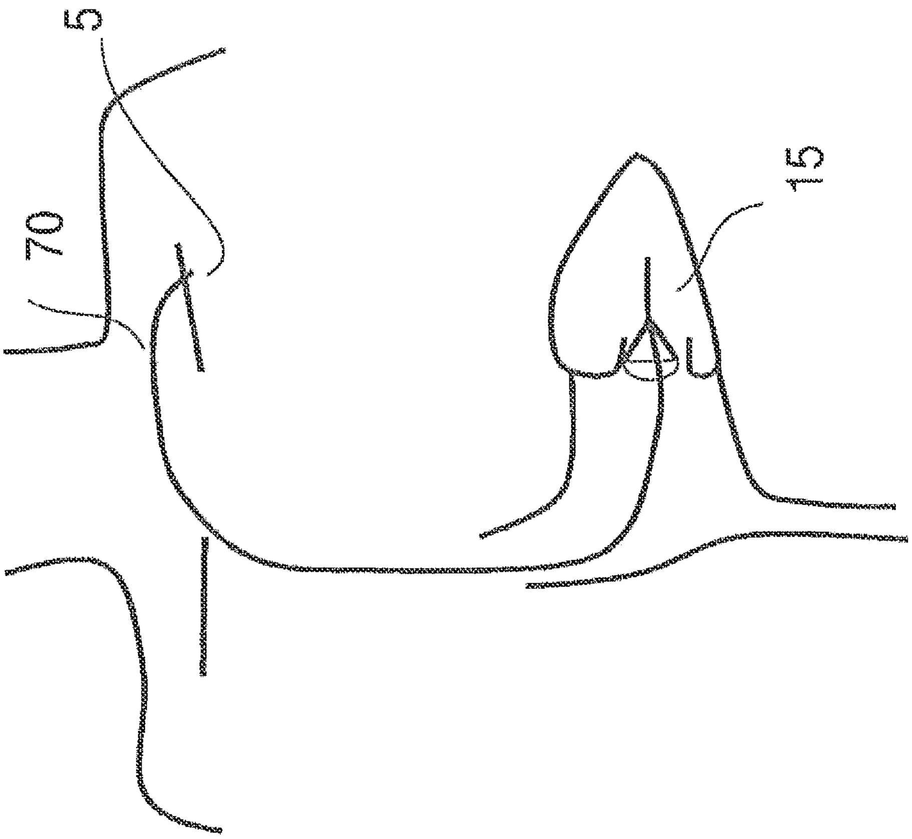
FIG. 15 shows suturing of the anchor guide wire at the proximal end.

A wire anchor 7 is then delivered (FIG. 2) through the first sheath 2 to the ventricle. This is an elongate anchor which is left in situ after the procedure (FIG. 15)

Figure 1:
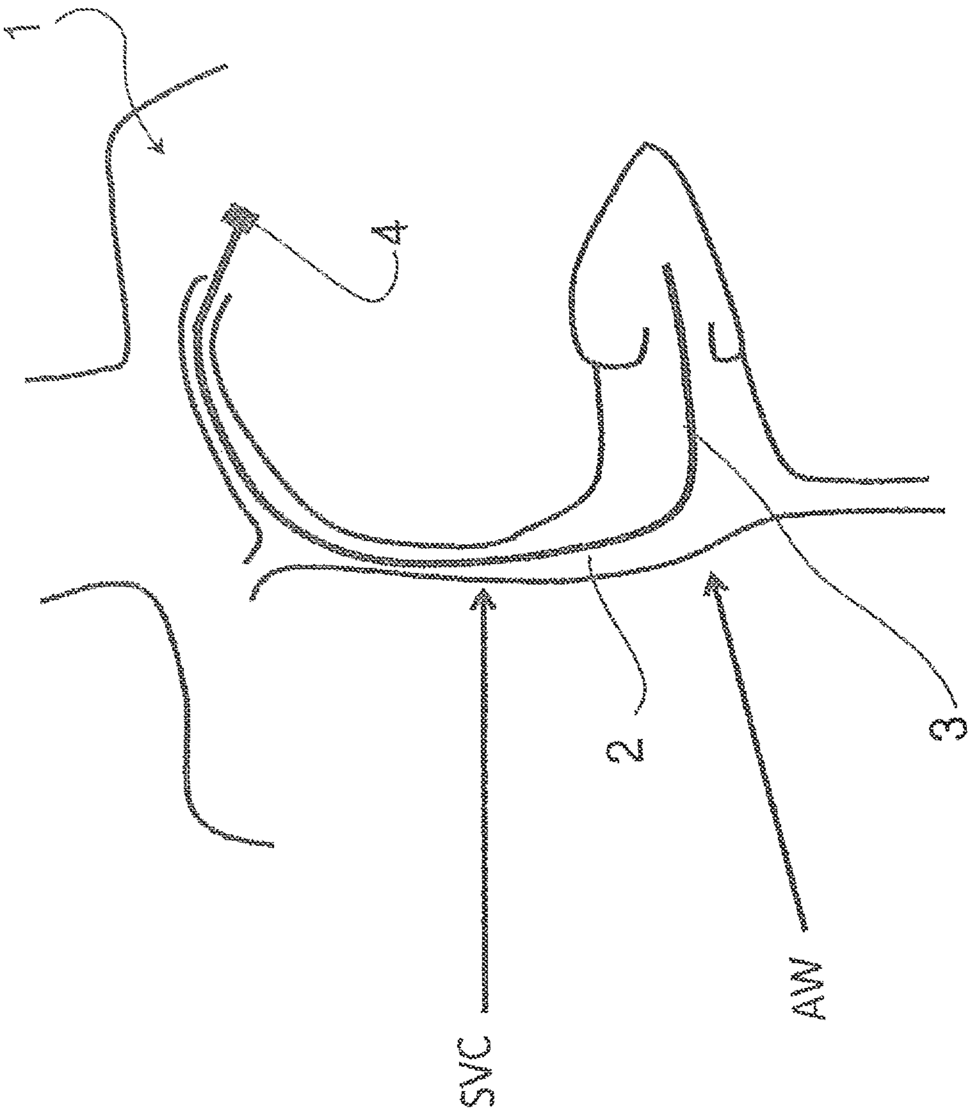
Figure 2:
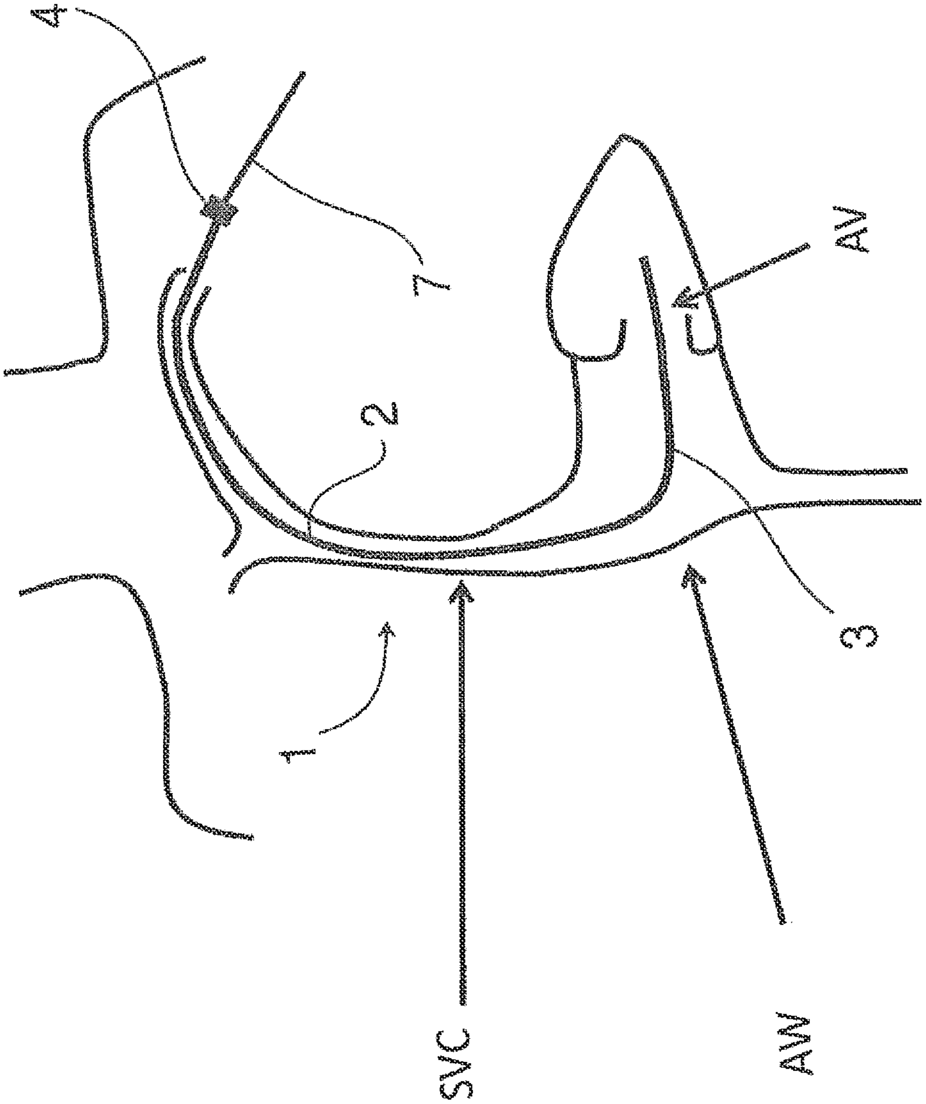
Figure 3:
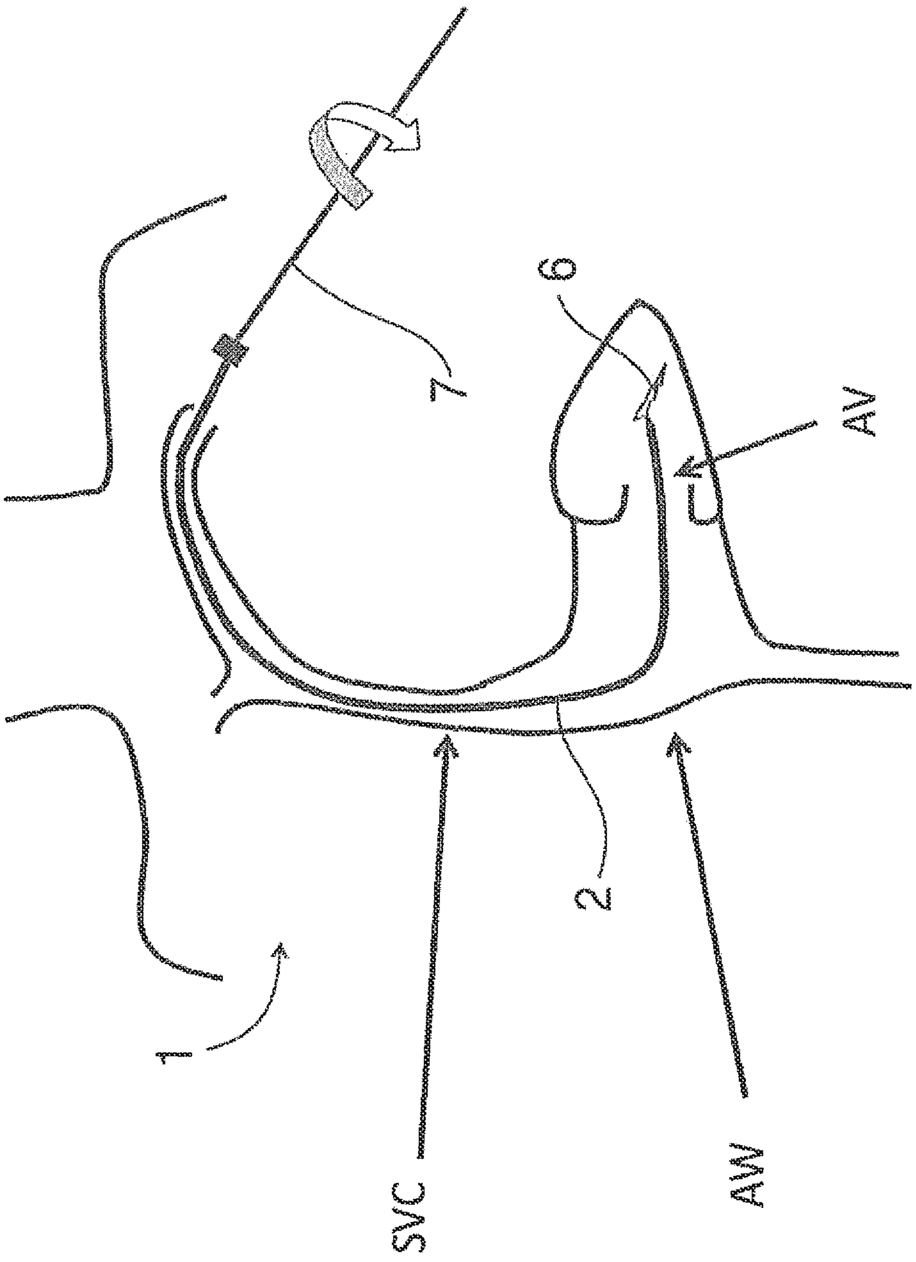

As shown in FIG. 3, rotation of the guide wire anchor 7 delivers an anchor element in the form of a screw 6 to the ventricular wall. Rotation of the anchor 7 causes the anchor element screw 6 to penetrate and lodge in the ventricular-wall. This fixes the elongate anchor 7 in place at the distal end, where it will remain after surgery. The anchor 7 can now be used during surgery for valve delivery and optimum positioning, and subsequently for valve support after surgery.

Figure 4:
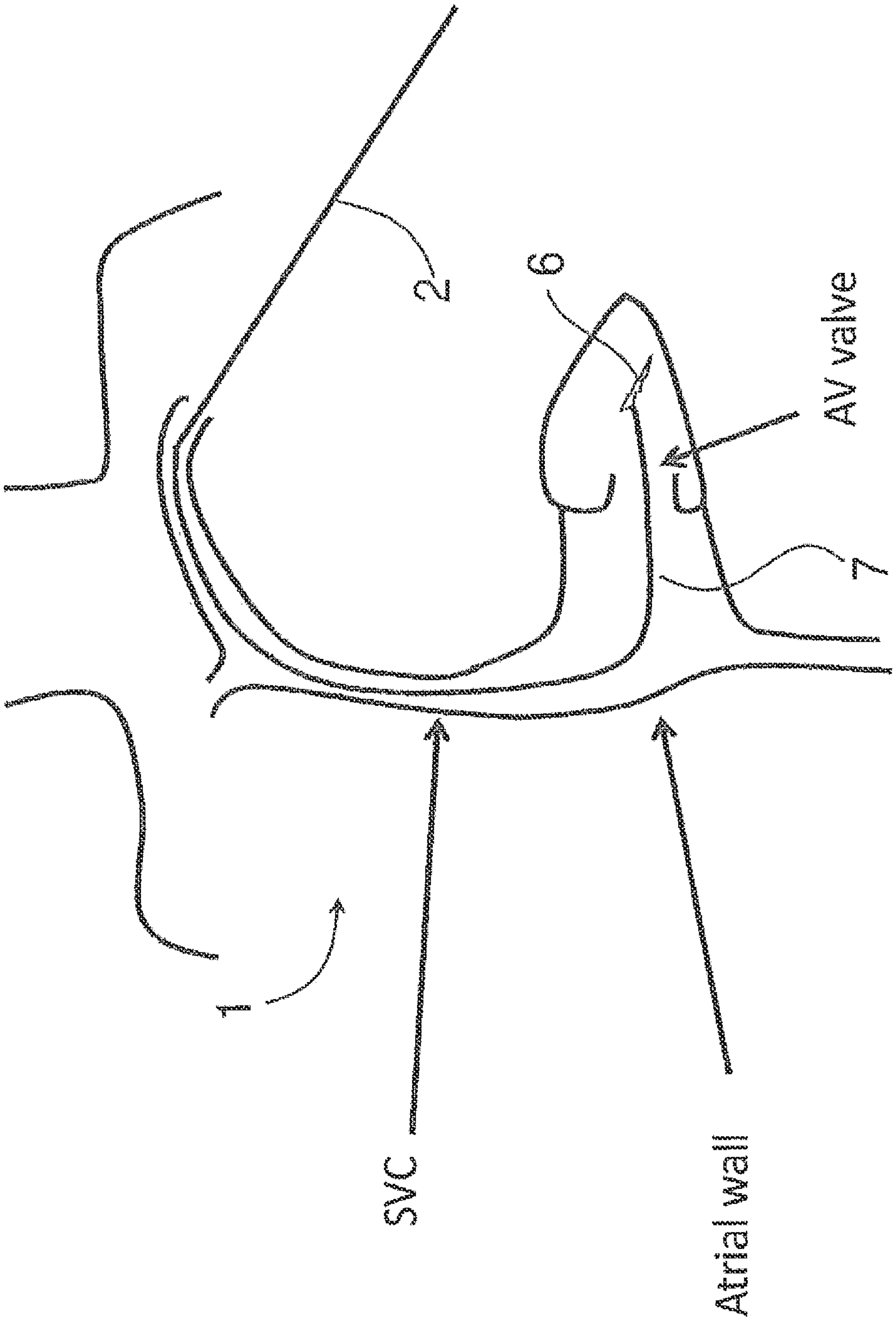
Figure 5:
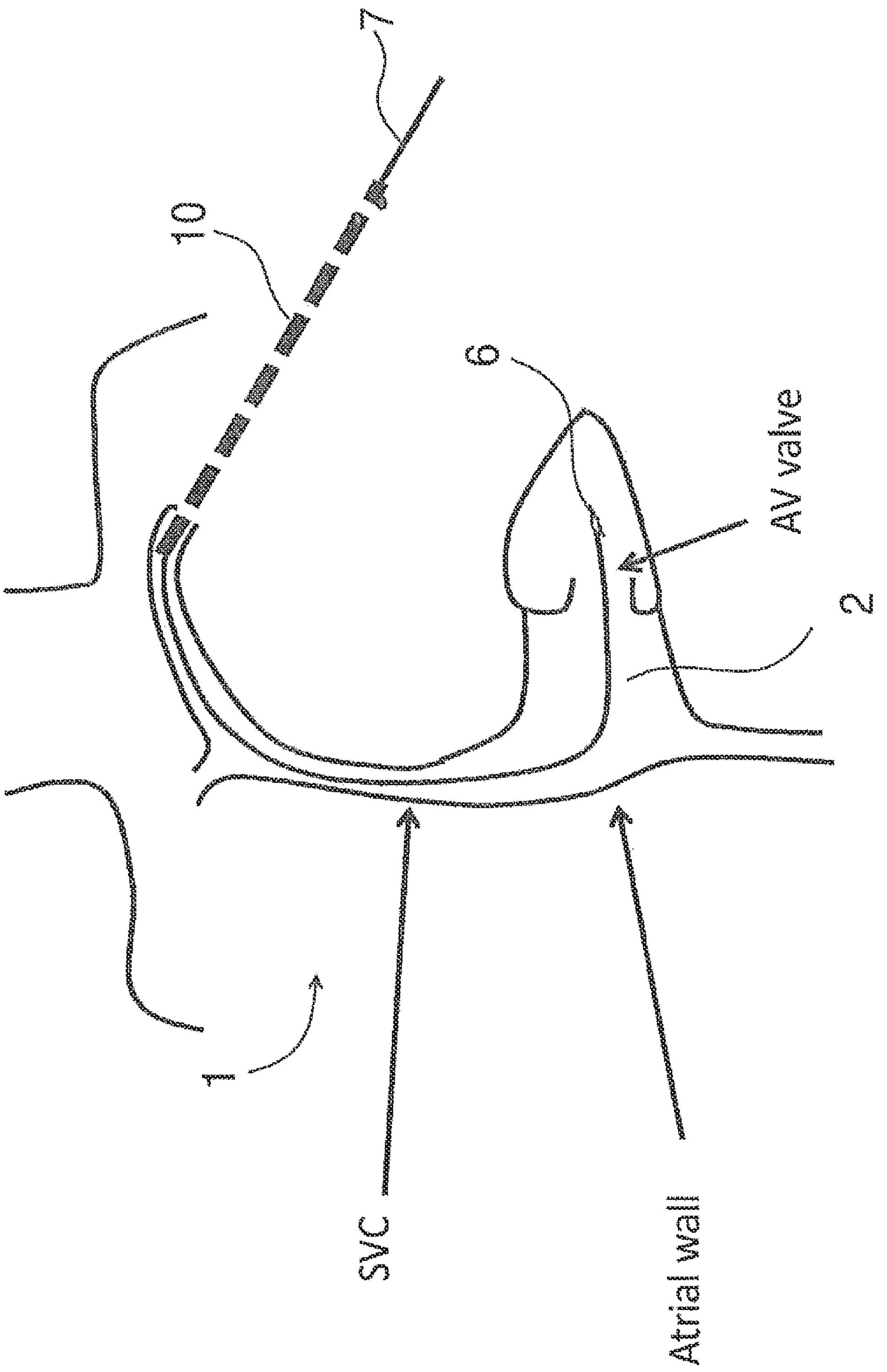
Figure 6:
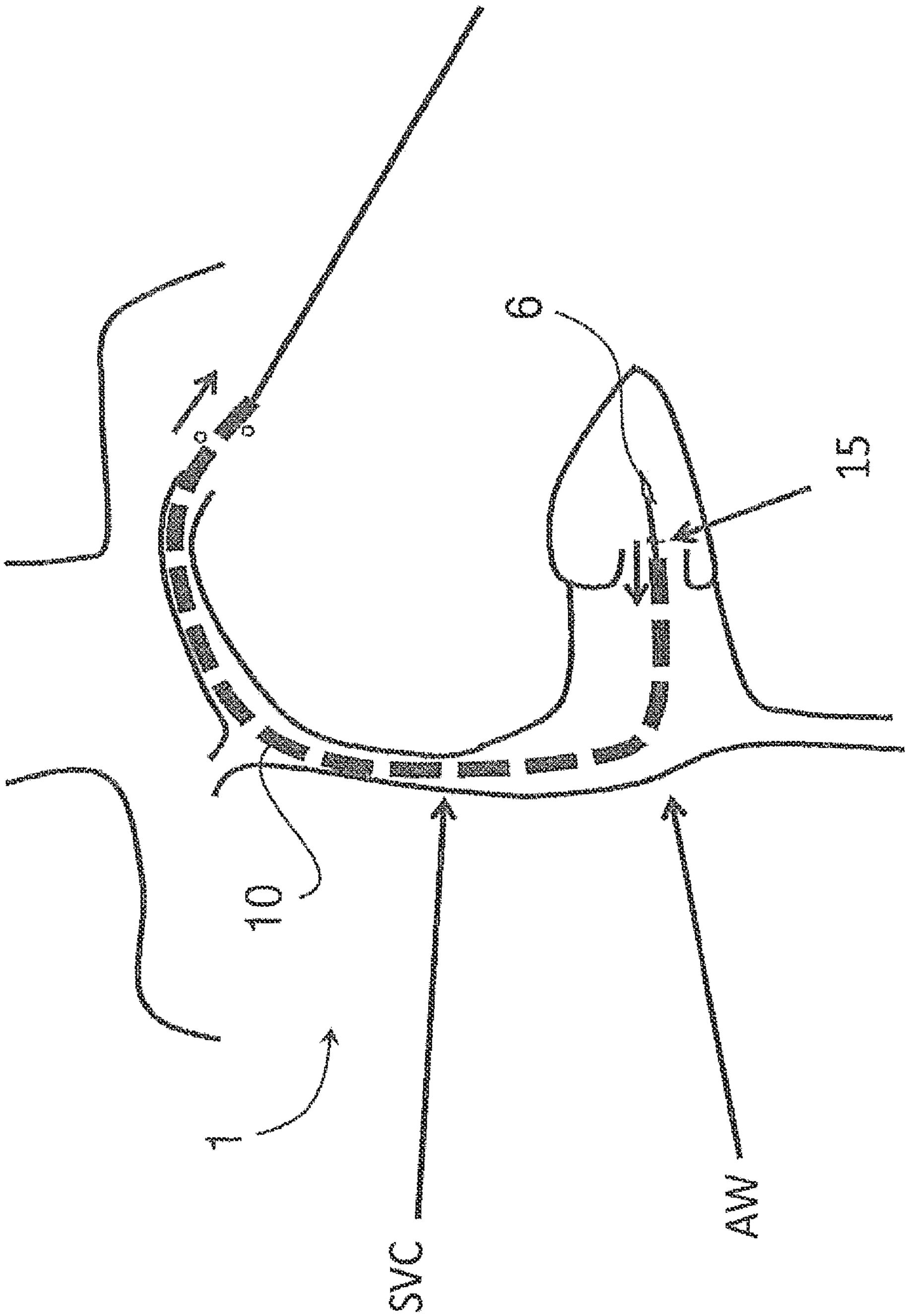

As shown in FIG. 4, with the anchor element screw 6 fixed to the ventricular wall the first (anchor delivery) sheath 2 is removed. A second, device delivery, sheath 10 is then fed in (FIG. 5) using the guide wire anchor 7. When the distal end of the second sheath 10 is in the ventricle the sheath is pulled back (FIG. 6) to deploy a prosthetic valve 15. This deployment, as described in more detail below, is at an optimum longitudinal position on the anchor 7.

The anchor 7 may for example be akin to the Biosense Webstar EZ™ steer catheter. The catheter delivery sheath may for example be the Medtronic™ Attain Deflectable catheter delivery system.

In an alternative embodiment, the first sheath 2 may be left in situ and used as the delivery sheath or support for the prosthetic valve 15.

Figure 7A:
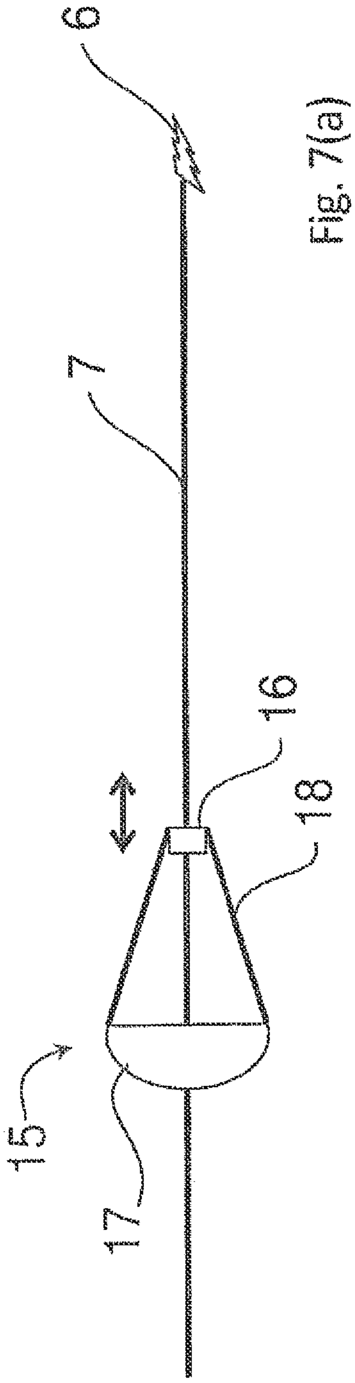
Figure 7B:
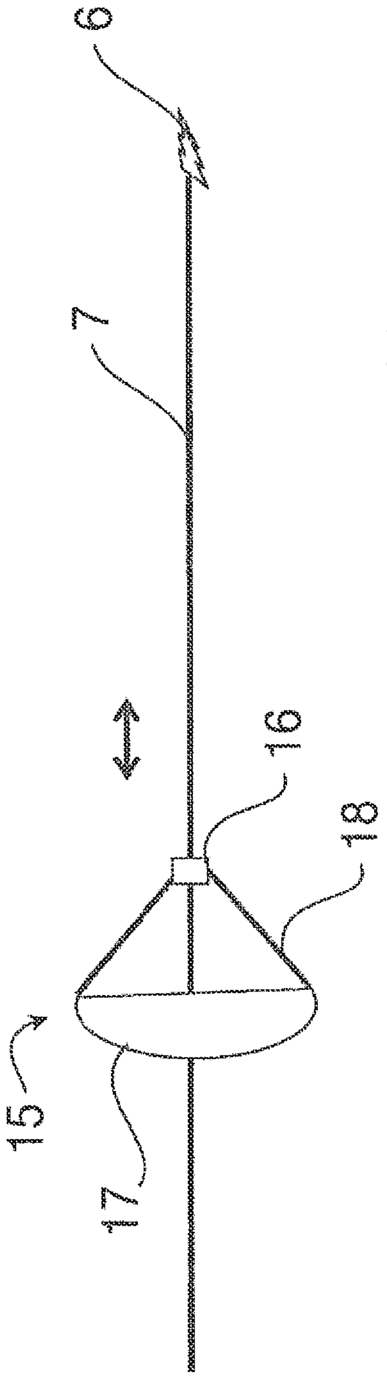

Referring to FIGS. 7(*a*) and 7(*b*) the valve element is a prosthetic valve 15 which comprises a coupler 16 of Nitinol which locks onto the guide wire anchor 7 upon release from the delivery sheath 10, due to its shape-memory characteristic in which the Nitinol reassuming the tighter shape in body temperature to lock down on the anchor. The valve 15 also comprises leaflets 17 of bovine or porcine pericardium or other material connected to the coupler 16 by chords 18. As shown, the coupler 16 is slidable and lockable on the guide wire anchor 7 under control of an actuator so that the valve area encompassed by the leaflets 17 can be changed. Instead of Nitinol, stainless steel or other suitable biocompatible material may be used.

Figure 8:
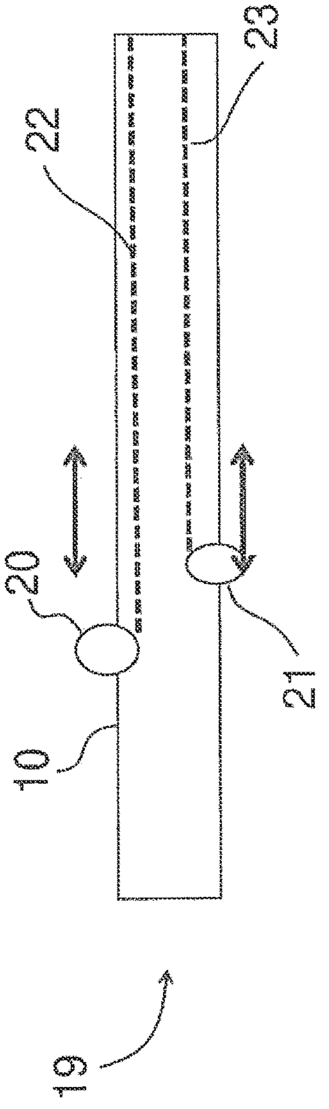
FIG. 8 is a diagram showing an actuator at a proximal end of the device.

FIG. 8 shows the actuator, 19, at the proximal end of the second sheath (catheter). There are two knobs 20 and 21 which are slidable on the sheath to axially move control cables 22 and 23. This alters the distance between the valve leaflets and the chord support coupler 16.

Figure 9:
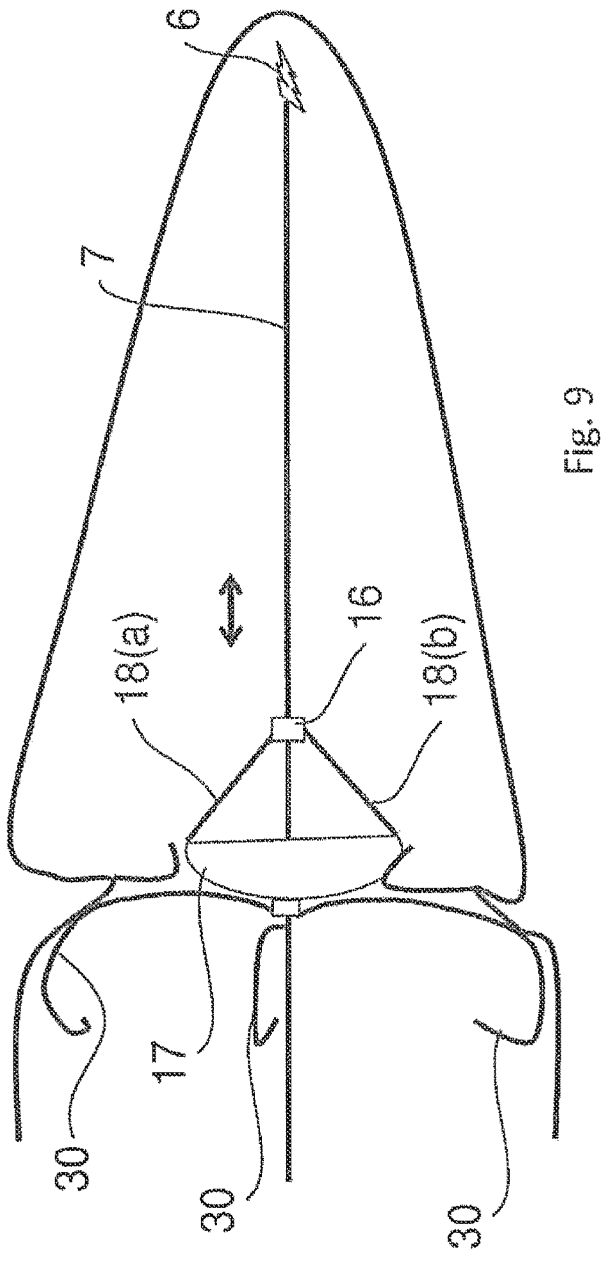
FIGS. 9 and 10 are diagrams illustrating differential adjustment of the prosthetic valve to provide a non-symmetrical configuration to suit the clinical situation.

FIG. 9 shows the effect of operation of the actuator 20/21 for X (axial) adjustment. There is a second coupler in the form of Nitinol prongs 30 at the level of the valve. The adjustable axial supports move the valve 17 and coupler in the X and Y axes. They are lockable within the anchor support as the Nitinol within the support changes shape within the anchor 7 to lock the support in place. In other embodiments, a proximal collet arrangement may be used.

Figure 10:
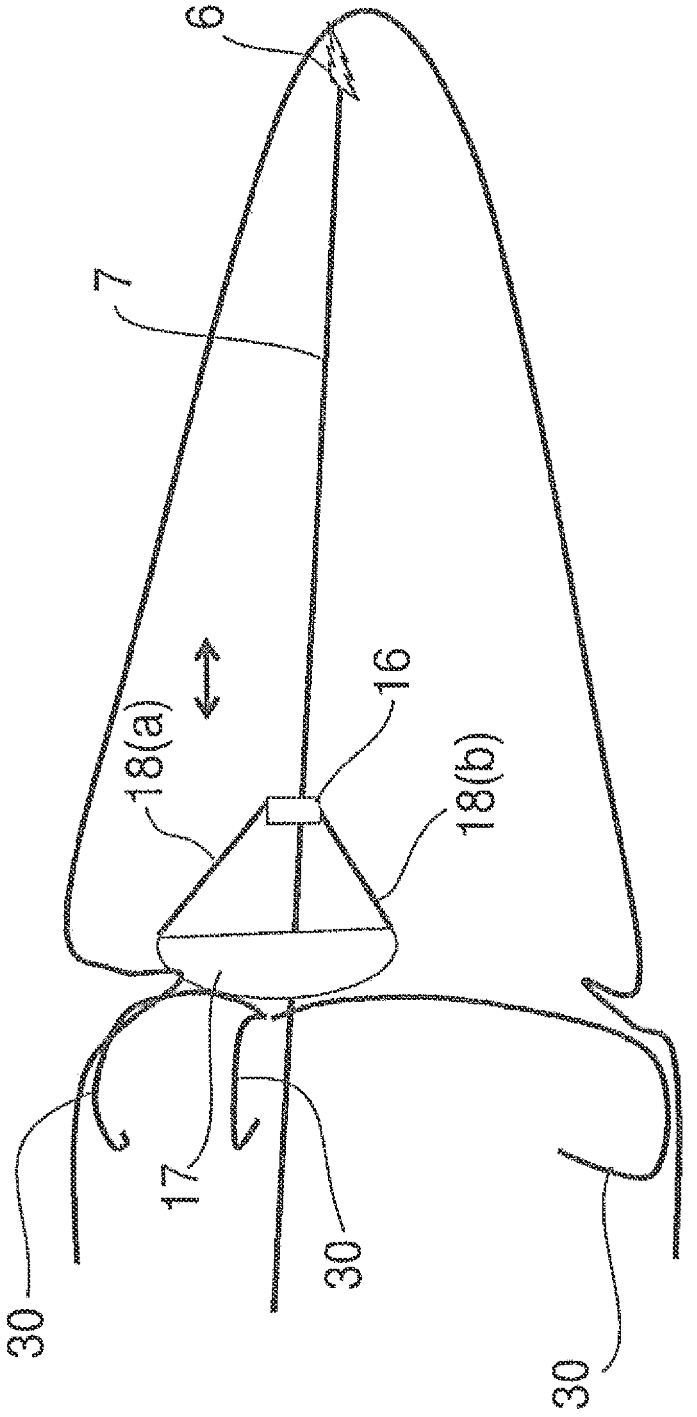

Also, as shown in FIG. 10 there is movement of the anchor 7 with the valve attached in the Y direction.

Figure 11:
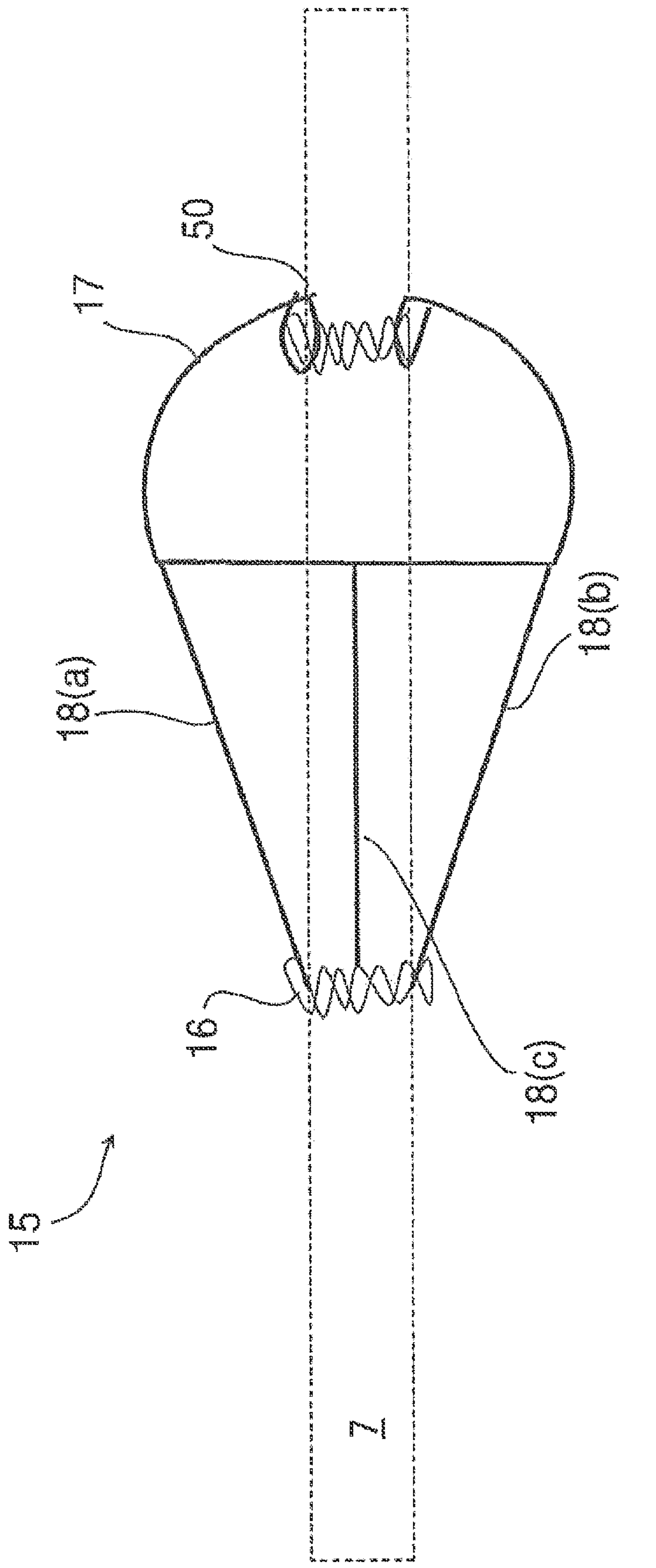
FIG. 11 shows specific a example of the fixing devices of the treatment device and FIG. 12 is a pair-of diagrams illustrating a principle of operation of couplers on the anchor.

Referring to FIG. 11 the valve 15 is shown in more detail. The coupler 16 is of Nitinol or stainless steel and there is a similar coupler, 50, for the leaflets 17 at the opposite (distal) end of the valve 15.

Figure 12:
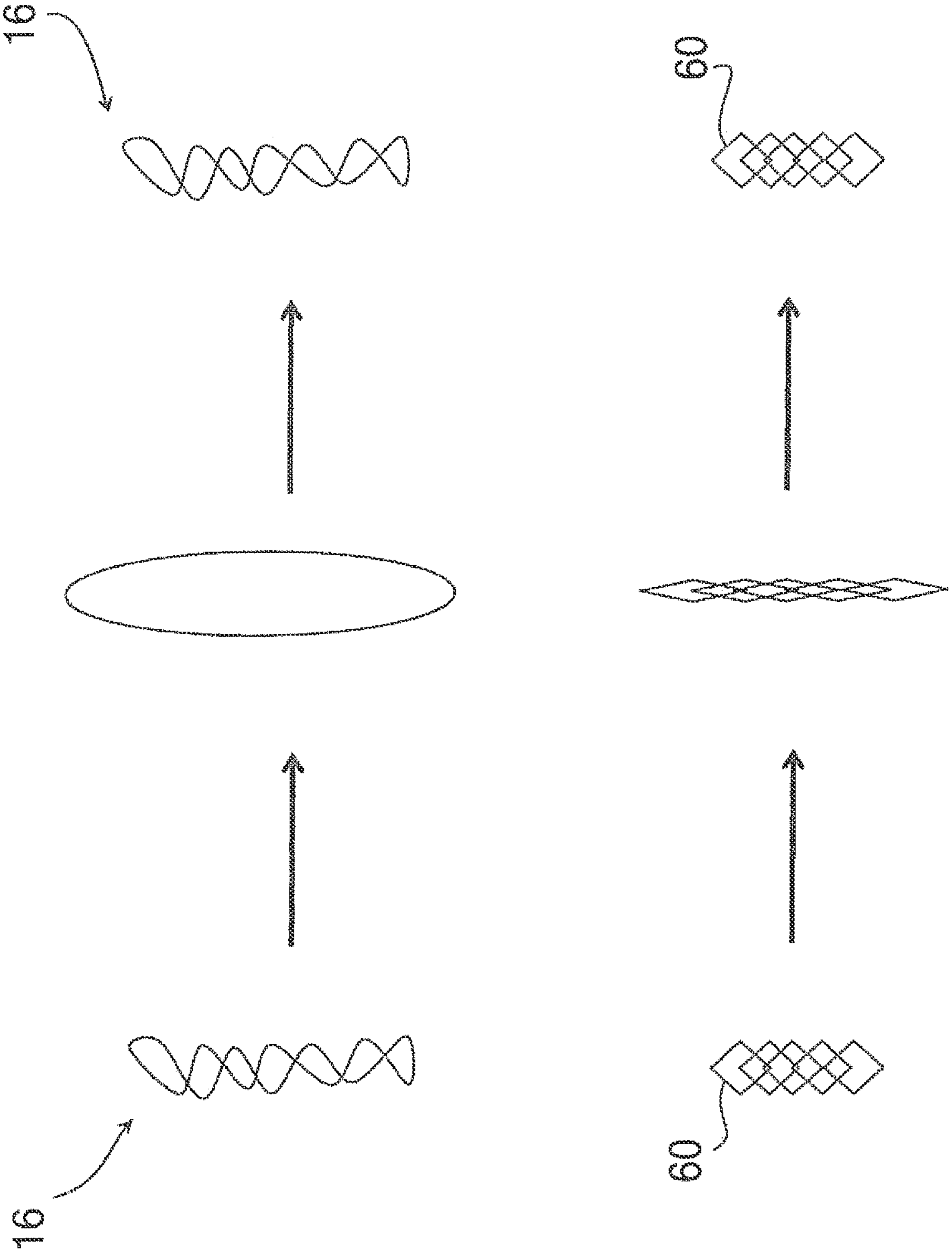

As shown in FIG. 12, the coupler 16 is a spring maintained in an expanded state by the second sheath 10, withdrawal of which causes it to contract onto the guide wire 7 when the valve is in the correct position. Each coupler is held open by the sheath/tube and pulling back the sheath allows the coupler to lock down on the anchor. The inner tube is pulled back much the same way as a Nitinol stent or valve is delivered, however instead of expanding to fill an orifice it contracts down on the anchor. FIG. 12 also shows a coupler 60 transitioning between the contracted and expanded positions.

Figure 13:
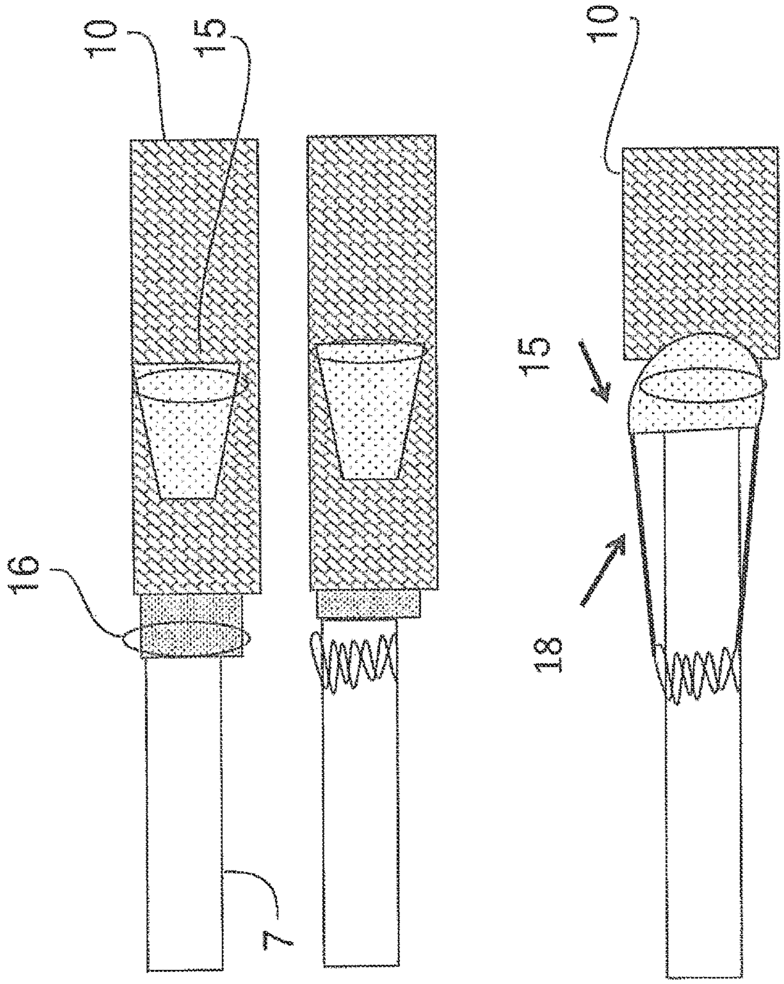
FIG. 13 shows the mechanism in more detail.

Valve delivery is also shown in FIG. 13, withdrawal of the delivery sheath 10 causing the coupler-16 to contract from a position supported by a tube within the sheath onto the anchor 7. The axial position of the leaflet coupler 16 can be chosen and adjusted for optimum effectiveness of the prosthetic valve. This is determined by observing when regurgitation is maximally reduced. The valve is delivered out of the sheath first and the ideal position along the anchor identified, then the fixation devices or couplers are released, first the distal and then the proximal or vice versa.

Figure 14:
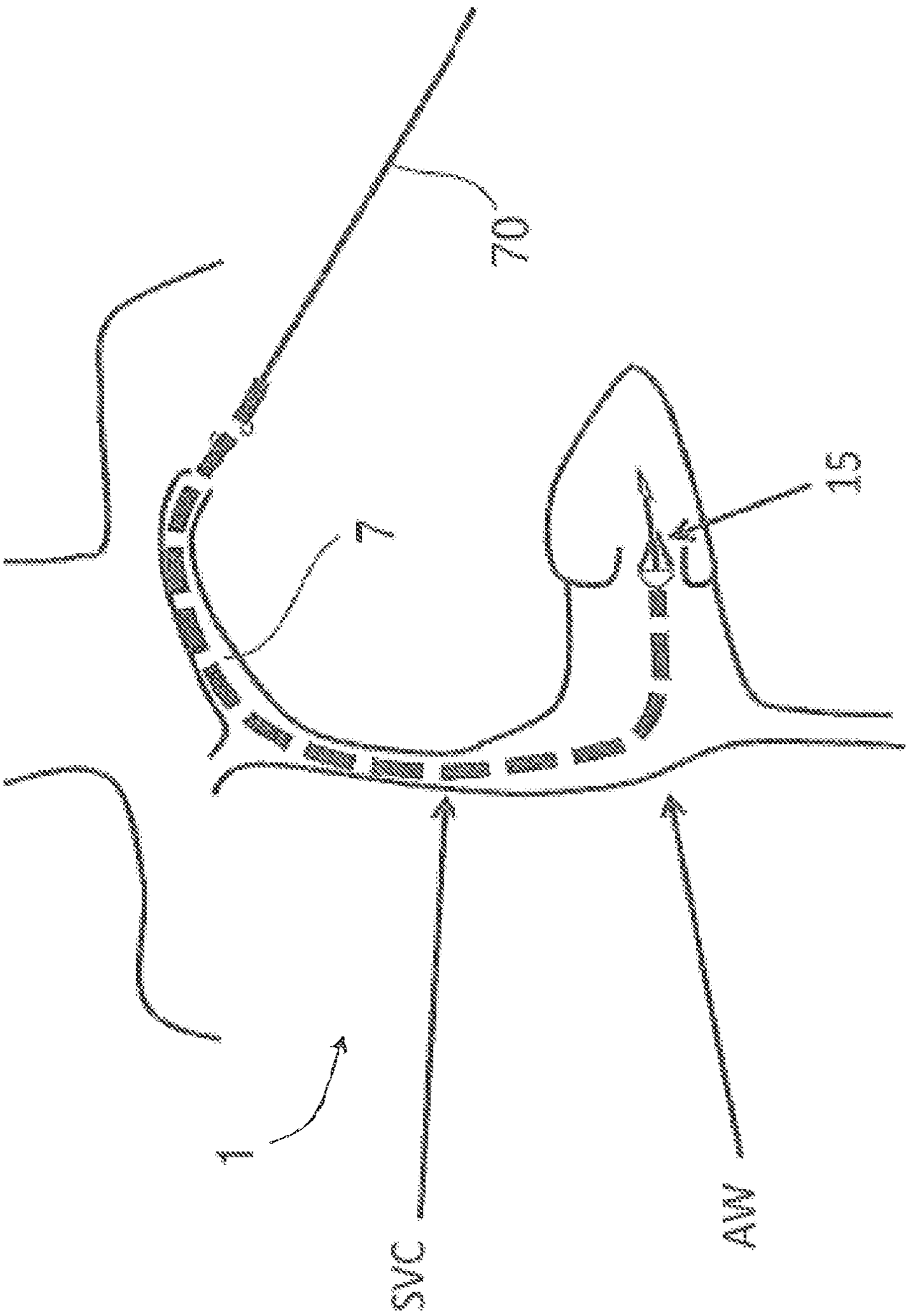
FIG. 14 is a diagram showing addition of stylets to achieve a desired shape in the atrium.

Referring to FIG. 14, one or more stylets or collars 70 can be introduced along the guide wire anchor 7 to change shape of the device in the atrium. These stylets or collars are shapeable and are inserted through the core or outside of the guide wire anchor to change the orientation of the anchor and support it against the atrial or vessel wall. Where a collar is used it may be sized to fit around the anchor and slide along the anchor to support the valve against the force of the valve regurgitation. The collar may be sutured to the subcutaneous tissue around the anchor to maintain its position, similar to collars used to fix pacemaker leads to the subcutaneous tissues as would be understood by a person skilled in the art. Hence, the atrial shape of the anchor can be altered by shapeable stylets or collars 70 that are inserted into the inner core or outside of the anchor guide wire. This provides an additional support for the anchor 7 and the prosthetic valve 15, in some cases avoiding need for the anchor to fix to heart tissue. In this case the stiffness of the anchor and the foundation provided by the atrium wall provide the necessary resistance to the forces applied to the valve element from the ventricular side.

Referring to FIG. 15, after delivery, the proximal end of the guide wire anchor 7 is sutured along a suture line 5 to subcutaneous tissue to prevent migration and to allow re-access to the prosthetic valve 15. This allows repeated access to the device to move or remove the valve 15.

Figure 16:
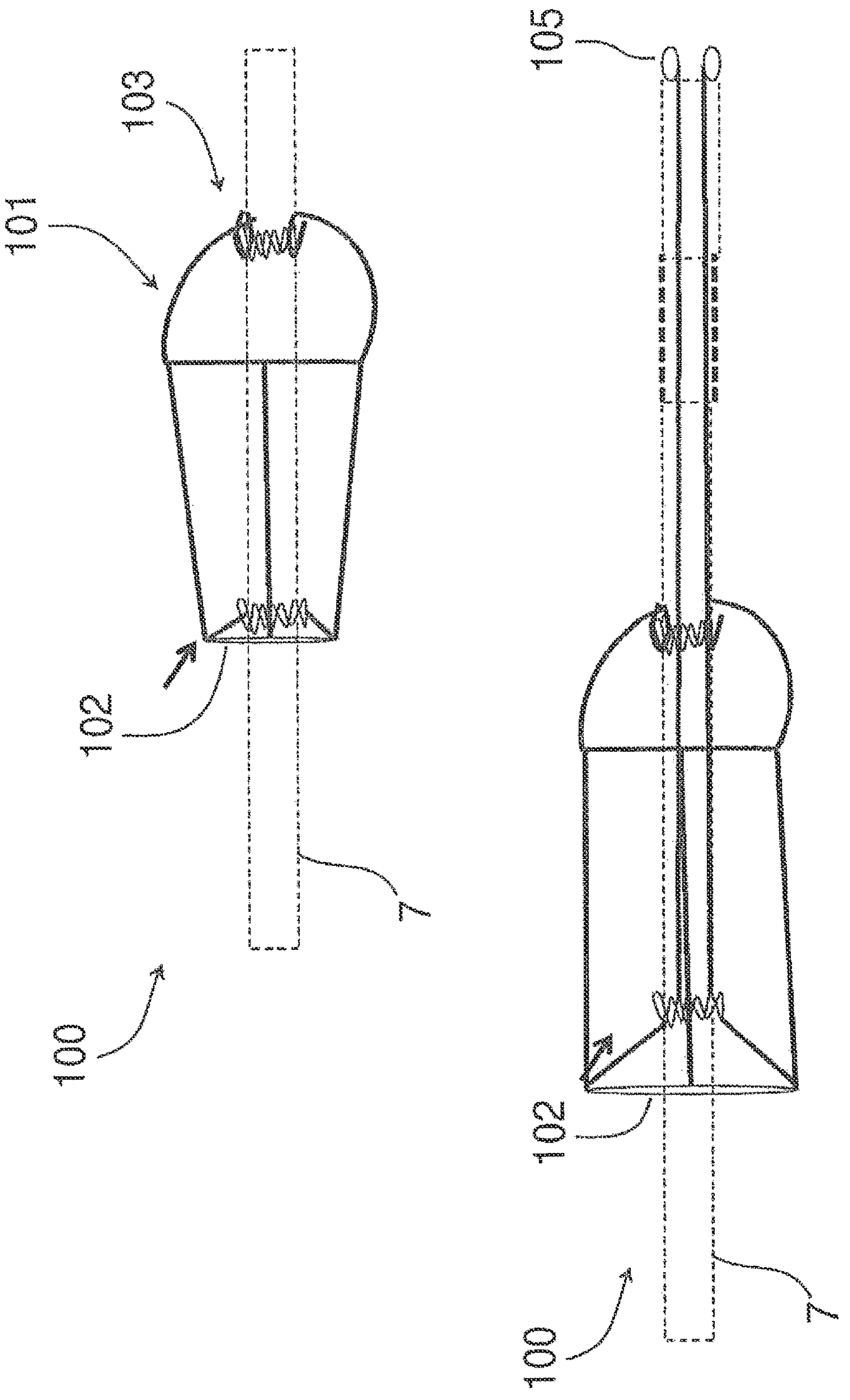
FIG. 16 is a pair of diagrams showing a treatment device with a chordal support with adjustable width.

Referring to FIG. 16, an alternative device, 100, has a valve element 101 with coupler 102 which is radially expandable in addition to being axially moveable on the guide wire anchor 7. There is also a coupler 103 at the other end of the device 100. The length and width of the coupler 102 can be varied by movement of knobs 105 on the proximal end. When width is correct, this is locked in position.

Figure 17:
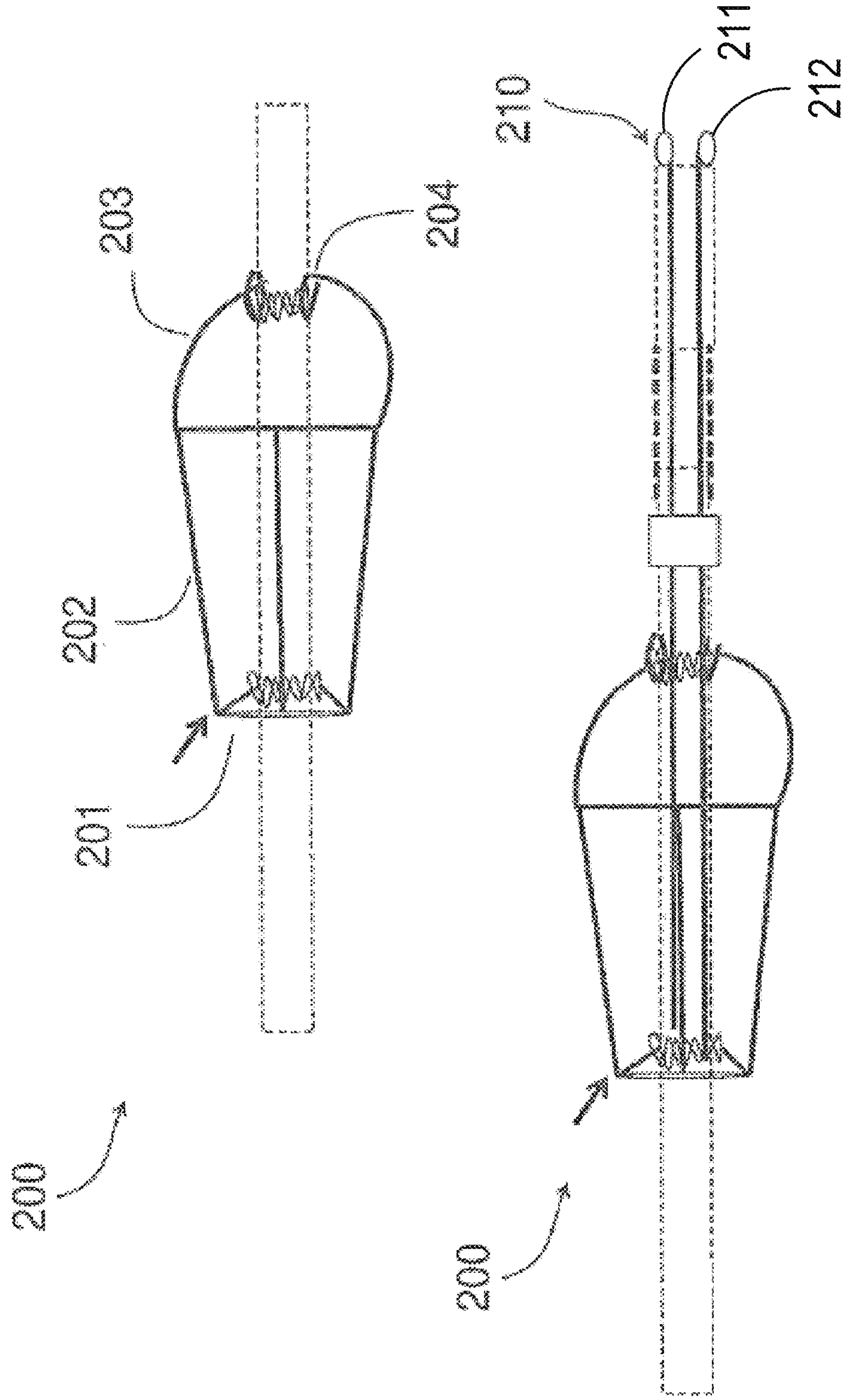
FIG. 17 is a pair of diagrams showing a treatment device of another embodiment with chordal length adjustment.

FIG. 17 shows a device 200 having a distal coupler 201, from which extend chords 202 to a valve treatment element 203 connected to the anchor by a proximal coupler 204. There is a mechanism 210 to vary length of chords 202. An actuator of the mechanism 210 at the proximal end of the catheter is rotated or moved to lengthen or shorten the chords 202. The rotation/movement of the actuator knobs 211 and 212 varies length of the chords by virtue of cables/wires within the elongate anchor. The chords are attached to the chordal support on the anchor 7 which can be locked down onto the anchor similar to locking the valve.

In various embodiments a valve element may be delivered and Fixed to a wire/lead anchor. The valve element may be a prosthetic valve of the "parachute" type supported by chords that are adjustable. The support frame of the chords may be adjustable and Fixable. The chords in some embodiments may be Fixed to the wall of the heart. The atrial configuration of the anchor may be adjustable and can be fixed through the delivery of stiff wire stylets or collars. The valve can be made as leaflets or a deformable material that deforms due to the pressure in the ventricle to form the valve support.

Figure 18:
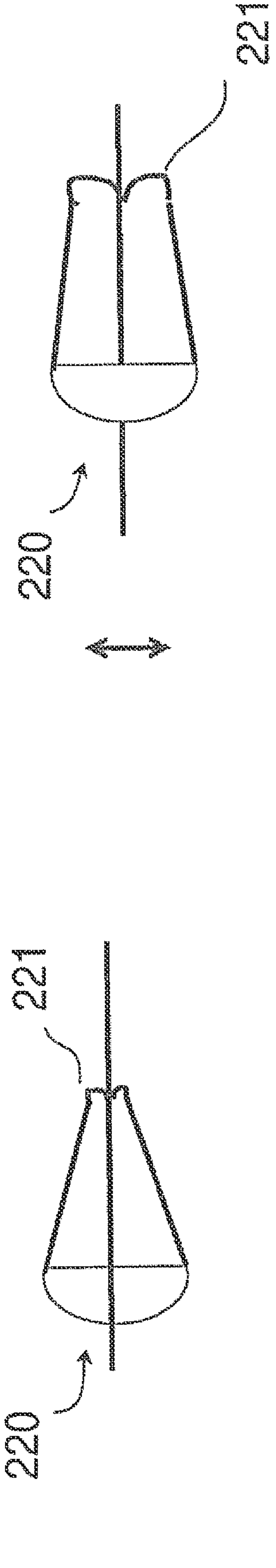
FIG. 18 is a diagram showing altering the position of chordal supports.
Figure 19:
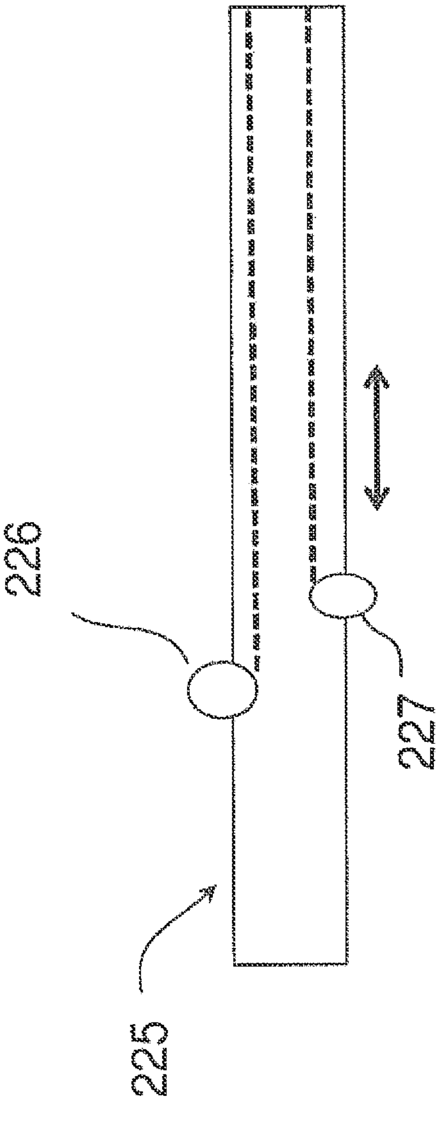
FIG. 19 is a diagram showing a user actuator for this altering.
Figure 20:
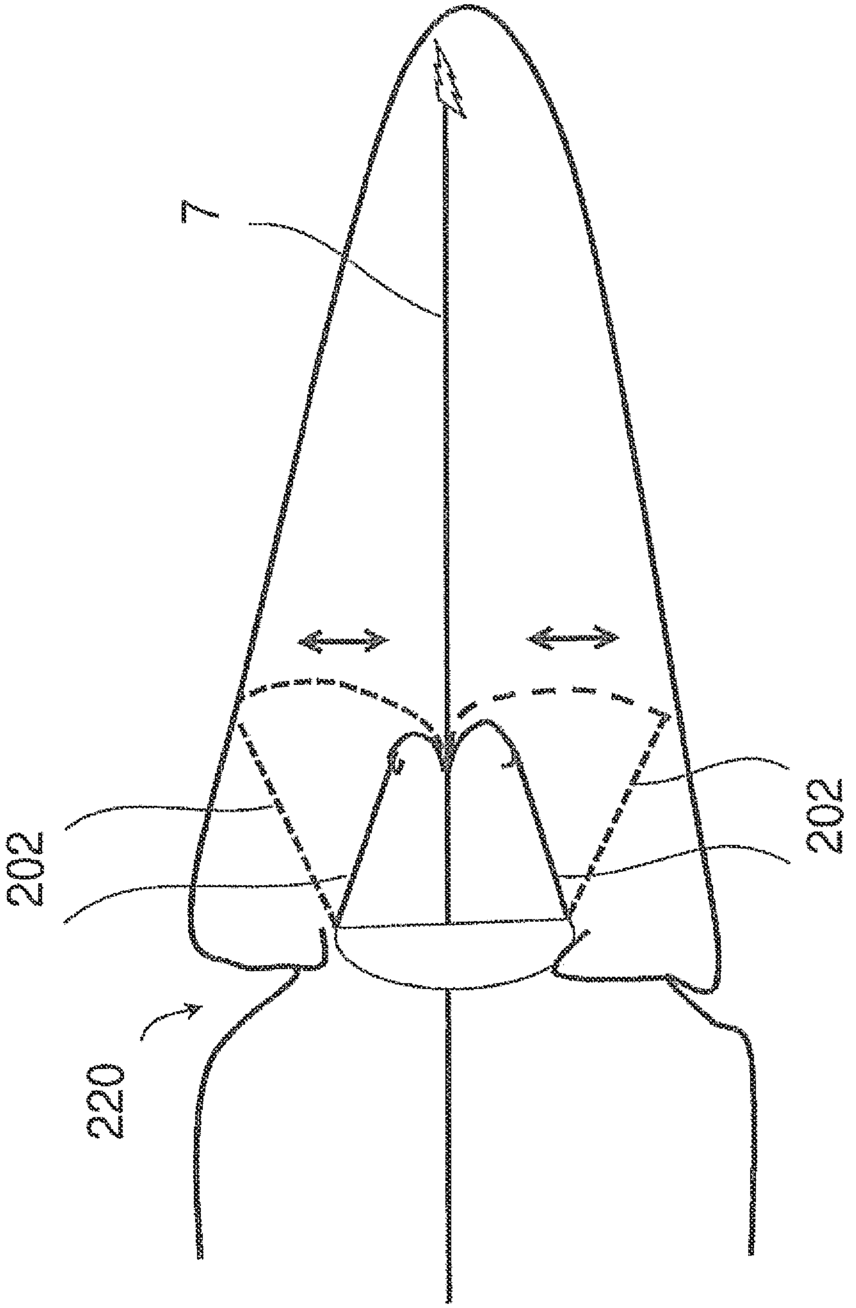
FIG. 20 is a diagram showing adjustment of chordal supports.

FIG. 18 shows in a device 220 altering of the position and configuration of a chordal support coupler 221, in which the coupler 221 expands radially. The coupler 221 is made of preformed Nitinol and takes up a curved shape as it exits the catheter, sliding knobs on the proximal end of the catheter delivers more of the Nitinol support from the distal end thus changing the position of the chordal support and FIG. 19 shows an actuator 225 having knobs 226 and 227 which are slid to alter the distance between the chordal support and the coupler. The extent of variation is shown in FIG. 20 by the interrupted lines.

FIGS. 21(*a*) and 21(*b*) show a valve element 235 in the closed and open positions. Valve leaflets 240 are supported on the proximal end on an atrial ring 241 and at the distal end they form an apex where they are supported on the anchor by a coupler 243. The valve element 235 opens through the centre. Chords 242 are attached to the chordal support (or "coupler") 243 but the leaflets 240 are attached in the alternate fashion so that the blood flows through the centre of the valve next to the anchor 241. The bases of the prosthetic leaflets 240 are attached to the Nitinol support that sits on the atrial side of the AV valve. When the ventricle contracts blood flow and the change in pressure in the ventricle causes the leaflets 240 to close against each other and the native heart leaflets co-apt against/on the prosthetic leaflets 240. When the heart relaxes the pressure drops in the ventricle below the pressure in the atrium and the valve leaflets 240 open to allow blood flow into the ventricle. The ring holds and supports the leaflets on the atrial side on the valve. It is flexible in that it is Nitinol and can be compressed into a delivery catheter for delivery and then returns to its ring-like shape post-insertion.

FIG. 22 shows a view from the left atrium into the ventricle a valve 900 having leaflets 901 and 902 which are shaped to match the shape of the native valve leaflets NL (also shown for illustration purposes). A valve support 904 is shown. The perimeter of the valve is defined by a Nitinol ring 903 which may for example, reside on the atrial side of the valve and may he sized to the line of insertion of the native valve leaflets in the atrium. The leaflets 901 of the implantable valve are shaped to match the shape of the native valve leaflets. There may be fenestrations 905 at the bases of the valve leaflets to allow as much blood flow through the device to prevent thrombosis.

Referring to FIG. 23, this illustrates an aspect whereby a support has an anchor 1000, ring 1001, and a ball and socket joint distal coupler 1002. This allows the valve leaflets 1003 to rotate and pivot to follow the movement of the heart, and the valve 1003 is only connected to the support at the distal end. The support anchor 1000 has a stiffness such that the valve 1003 may be moved to fit the shape of the native valve structure, by rotation of the support anchor 1000.

FIG. 24 shows a configuration of valve 1100 having a Nitinol atrial ring 1102 supporting leaflets 1101 moved by chords 1103 attached to a ring Nitinol support with support posts 1104 which extend into the ventricular-side of the valve. In this case the leaflets 1101 are shaped and sized to match the native leaflets. The two lower diagrams are views from the ventricle of the open and closed valve.

FIG. 25 shows a valve in the open configuration 1200 having a wire support 1201 at the distal end of which there are Nitinol supports 1202 which extend radially and distally to their ends which are attached to a support ring 1203 (also of Nitinol). The valve leaflets are attached at their base to the Nitinol ring 1203. The apex of the leaflets are attached to the coupler on the anchor 1204.

FIGS. 26 to 28 show a device 1350 having an anchor 1351, a distal coupler 1352, a proximal coupler 1353, chords 1354, and leaflets 1355 with the leaflets fixed at their base to the Nitinol or an inflatable ring 1358. The ring 1358 may be supported by one or more struts 1357 which attach to the anchor via the proximal coupler or may be attached to the distal coupler 1352 by a Nitinol struts.

There is an expandable support having radial spokes 1357 extending from the proximal coupler 1353 to the ring 1358. The support 1353, 1357, and 1358 provides support for the device in use in addition to or instead of the fixation device at the distal end of the anchor. The support 1353/1357/1358 and the leaflets 1355 are sewn or glued to the ring 1358 and the chords are tied or sewn or clamped or glued onto the chordal support 1352. The chords may be integral parts of the material used to form the leaflets and the leaflets are cut in such a way as to form the chordal supports attached to the chords 1354.

The leaflets 1355 are hook-shaped, extending at their ends distally and radially. This provides more surface area to prevent regurgitation with less assistance from co-apting native leaflets, which may be badly damaged, As shown in FIG. 27, the native leaflets NL (native chords C also shown) co-apt against the valve leaflets 1355 within the ventricle, while the support ring 1358 engages the atrium wall immediately proximal of the native valve. The top diagram shows the valve open, while the bottom diagram shows it closed.

FIG. 28 shows a device 1359, in which like parts are indicated by the same reference numerals, and in which there are spring-loaded clamps 1360 on radial arms or spokes 1361.

FIG. 29 shows a device 1600 with an outer skirt 1605 attached to an atrial ring to prevent regurgitation between the native leaflets and the valve. Otherwise, the arrangement of the valve leaflets sand their chords is as described above.

Referring to FIG. 30 a device 1700 comprises an elongate wire anchor 1701 supporting at its distal end a prosthetic valve 1702. The valve 1702 has a parachute-shaped valve member 1702 linked by chords 1704 to a coupler 1705 on the anchor 1701. The anchor 1701 does not need, for some uses at least, to be fixed to the heart wall by a fixing element. Instead, anchoring support is provided by stiffness of the anchor 1701. The anchor 1701 rests against, for example, posterior atrial tissue (atrial wall, AW) or the inter-atrial septum.

Referring to FIG. 31 a device 1750 also has an anchor 1751 which does not need a fixing element, supporting a prosthetic valve 1752. In this case there is a sub-cutaneous motorized controller 1753 which can deflect the positions of the anchor 1751 and the valve 1752 post implantation.

Referring to FIG. 32, a device 1800 also has an anchor 1801 which does not need a fixing element. There is a support element 1802 for retaining the anchor at a particular position as it passes through a wall, by clamping opposed sides of the wall. The support element 1802 is akin to an ASD closure device with a central aperture through which the support passes. As shown, the anchor 1801 at the distal end 1805 bends through 90° in a variable manner so that the positions of the valve (1803) can be changed. The shape of the distal segment of the support is variable so that the position of the valve can be changed. Once in the correct position the shape of the support is lockable FIG. 33 shows leaflet supports 2300 and 2350. The support 2300 has a ring and posts extending from the ring across the AY valve into the ventricle. The support 2350 has a ring and an arch extending across the ring and into the ventricle.

Referring to FIG. 34, a leaflet support 2400 for a valve has only a ring. Also, a support 2450 has a ring 2451 and member 2452 connected at diametrically opposed sides of die ring 2451 extending into the ventricle with a shape of the AV valve co-apting line. This is a Nitinol atrial ring to which the leaflets are sewn. These diagrams show that the ring can have a chord or leaflet support that extends in an arc from the ring into the ventricle.

FIG. 35 shows alternative supports 2500 and 2550. The support 2500 is crescent (saddle) shaped in enface view, whereas the support 2550 is oval in enface view.

FIG. 36(*a*) shows a support 2600 having a ring 2601 and valve leaflets 2603 are sewn to posts 2602 extending across the valve. This is a ring member and two post supports to which the leaflets are attached.

FIGS. 36(*b*) to 36(*e*) show a device 2650, similar to the device in FIG. 36 (*a*) having an elongate anchor 2651 with proximal-end actuators. At the distal end there is an atrium support ring 2652 linked by Nitinol supports 2653 to a distal actuator 2654. There are also axial support arms 2655 which in use extend across the valve and support leaflets 2656.

Movement of all the proximal actuators together moves the valve more apically or more into the atrium. Actuators are connected via wires to the atrial support ring of the valve.

Movement of one of the proximal actuators tilts the valve.

FIG. 36(*c*) shows the open and closed valve with native leaflets co-apting on the valve leaflets.

FIG. 36(*d*) shows a magnified view of the support cables for an atrial ring of the valve running the length of the support.

As shown in FIG. 36(*e*), there is an outer deflectable support sheath 2657. This diagram also shows an inner support tube can rotate within outer deflectable support sheath. The valve is rotated to align with the commissures of the native valve.

Referring to FIG. 37, a device 3300 has an anchor 3301, Nitinol couplers 3302 and 3303, valve leaflets 3304, and chords 3305. There are also secondary chords 3306 extending from the distal coupler 3302 to the proximal sides of the leaflets 3304. The leaflets 3304 have fenestrations 3310 arranged around the axis close to the coupler 3303. The fenestrations 3310 allow washing jets as the pressure in the ventricle rises and the valve closes causing blood flow from the high pressure ventricular side of the valve to the lower pressure atrial side of the valve, ensuring small amounts of blood flow at the base of the valve to prevent clot formation.

FIG. 37 includes, on the bottom left, a view of the valve from the atrium, showing the fenestrations 3310 more clearly.

As shown in FIG. 38, in a device 4000 rotation of the knobs causes chords 4001, 4002 to be fixed to the wall of the heart by way of fixation devices at the ends.

FIGS. 39 and 40 show a valve element 4050. It has a native state shown in FIG. 39 which is frusto-conical with the narrow end facing into the chamber, and has a resilience such that when pressure rises in the chamber it narrows to a point facing into the chamber and the larger outer end seals the chamber as shown in FIG. 40.

FIGS. 41 and 42 show a valve element 4060 in which the element has an elastic shape which conforms to the shape of the orifice under high pressure and returns to its native state under chamber low pressure conditions. The overall shape is T-shaped in cross-section, with a disc-shaped head outside and a stem inside.

FIGS. 43 and 44 are diagrams showing various alternative configurations 4071, 4072, 4073, 4074 of material cuts during manufacture to suit the nature of the valve defect. The valve and chords may be made from a single piece of pericardium or other suitable biocompatible material, or alternatively suture material or the like may be sewn into the leaflets to form the chords. The shapes in end view may have 4, 8 or any desired number of aims, and the leaflets may have any desired configuration of end shape at the radial outer position. The central part, for engaging the native valve leaflets, may have a round, oval (4080, 4081, 4082), or polygonal (4083) shape when viewed in the axial direction.

FIG. 45 shows a view from within the ventricle in use, of a device with an anchor coupler 4351 and chords 4352 from the coupler 4351 to an atrial ring 4354. There may be a spring-loaded clamp 4360 fixed onto the commissure. This support arrangement effectively clamps on both sides of the native valve, the arms and clamps 4360 on the V side and the ring on the A side. An alternative is also shown, namely a Nitinol hook 4380 on the ventricular side of the AV valve, within the delivery catheter there are two smaller sheaths that maintain the Nitinol clamps in an open state. When the clamps are in the correct positions the sheaths are pulled back to release the Nitinol to engage the heart tissue.

FIGS. 46 and 47 show Nitinol supports 4390 for engagement on the LV side of the valve. The supports 4390 are Y-shaped, with two radially distal branches for engaging within the tissue, they extend from a ring 4391 on the atrium side in use. FIG. 47 is a ventricle-side view.

FIG. 48 shows delivery of a device 4400 with clamp/hook like valve supports to AV groove. Hooks 4401 being delivered in a compressed state in a delivery catheter 4405. Chords 4402 are shown. The hooks 4401 or spring-loaded clamps are delivered in a compressed state in delivery the catheter and are released/positioned in the commissures of the valve at the AV groove.

FIG. 49 shows a device 4410 having hook-like supports 4411 at the ends of chords 4412. The Nitinol supports 4411 are attached to chordal supports on the LV side of the AV groove.

FIGS. 50 and 51 show delivery of a device 4500 with spring-loaded wing-like supports 4501. These engage the LV side of the annulus. Nitinol wings 4503 are attached to the chordal supports 4501 and are delivered by pulling back the sheath 4502.

Referring to FIG. 52, a device 4700 has an elongate anchor 4701 and a valve element 4702 comprising a Nitinol frame 4703 covered by a cover 4704. The cover may be of any biocompatible material such as pericardium. The shape is to allow the native valve leaflets to co-apt against it. As shown in FIG. 53, the device is delivered by a catheter 4710, in which retraction of the delivery sheath allows the valve element to expand. As shown in FIG. 54, when the device is in the optimal position on the elongate anchor Nitinol springs are released to clamp the device at this position.

FIG. 55 shows an alternative arrangement of parachute valve 4800 without leaflet chords. Leaflets 4801 are cup-shaped and are sewn or glued directly to a Nitinol support frame 4804 which attaches to an anchor 4803. There may be fenestrations 4805 at the base of the leaflets to allow the washout of blood to prevent thrombosis.

In various embodiments the valve support of the device has one or more of the following features.

- Lead like structure which anchors in the ventricle.
- Stiff stylets or outer cover/catheter that stiffens the anchor to support the valve element against the heart wall or atrial septum
- Deflectable/lockable catheter with inherent stiffness that maintains valve element in position
- Catheter is adjustable post implantation through motorized control implanted under the skin at the point of exit of the catheter from the vein.
- Nitinol plug with central lumen through which the support catheter is delivered, similar to amplatzer ASD device may be placed across the atrial septum to provide support to the catheter as it crosses the atrial septum
- Hooks which attach to atrial ring of valve and support the valve from the commissures or the ventricular side of the valve
- Valve element is fixed to the distal end of the support or is moveable along the support and fixable to the support when in the correct position
- Chords and atrial ring may be fixed separately to the support and adjustable along the support
- Valve element may pivot or rotate to adjust to the movement of the heart/native leaflets The valve may have one or more of the following features.

- Parachute valve shape with multiple chords holding valve leaflets against the regurgitant flow of blood
- Chords are supported by chordal supports
- Chords and chordal supports may be adjustable in length and position and fixable on anchor
- Valve element may have one, two, three or more leaflets
- Valve element may be shaped to replicate the shape of the native leaflets and commissure
- Valve element may have atrial ring to which the leaflets are attached and the orifice of the valve is in the center
- Valve element may have only one leaflet attached to atrial support
- Valve element may have skirt or lip on atrial ring to prevent regurgitation around the valve
- The atrial ring sits against the atrial side of the native leaflets.
- The native leaflets co-apt onto the atrial ring and leaflets of the prosthetic valve It will be appreciated that the invention achieves a percutaneously-delivered valve made up of one or more leaflets, which can be made from porcine or bovine pericardium or other materials, which is attached to an anchor by one or more supports either on a ring on the atrial side of the native valve or directly to the anchor. The stiffness of the anchor resists the force pushing the valve into the atrium and maintains the valve in the desired position.

Versatility to suit the individual clinical conditions is achieved because the leaflets may be supported by chords which can be varied in length and position and may also be fixed to the wall of the heart. The valve may be supported by an anchor which is fixed to the wall of the heart. The valve may be supported by a portion of the anchor against the atrial wall, due to stiffness of the anchor. This can be reinforced by the use of stylets or collars within or around the anchor. The valve may additionally or alternatively be supported by struts or hooks on the LV (distal) side of the valve.

Where the device has fenestrations it allows blood flow back into the atrium. This is a very simple and effective mechanism to prevent clot formation.

Also, it is envisaged that the leaflets and chords may be attached to a single elongate support that attaches to the anchor. In this case the distance between the leaflets and chords is fixed and there are different sizes of device that are implanted depending on the size of defect in the valve.

Also, it is envisaged that there may be a support from the atrial or interatrial wall which supports the valve (and possibly also an anchor) and prevents it prolapsing back into the atrium. The support is delivered over the anchor to rest against the posterior atrial wall. The support may be hollow and fit around the anchor or the valve may be attached to the distal end of the support. The distal end of the support is deflectable by means of a mechanism such as a pulley system within its core that alters the tension in elements within its wall. The shape of the distal end of the support may be lockable. The support may abut against the coupler of the valve attached to the anchor. The support has an inherent stiffness that serves to maintain the valve in the desired position. For a support for the left sided AV valve there will be a fixed angle bend in the support as it crosses the interatrial septum and the distal end of the support is deflectable as well.

Also, arms to position the valve in the superior/inferior axis can be fed through to rest against the posterior atrial wall to support the valve.

The invention is not limited to the embodiments described but may be varied in construction and detail. Any part of the device (such as a coupler or chord) may be of a material which is visible to equipment such as echo or X-ray imaging equipment. Also, the prosthetic valve adaptation may not be under user control, even where it has leaflets. For example pressure differential may be availed of to cause adaptation of the leaflets to suit the nature of the defect in the heart valve. The device may further comprise a controller arranged to be implanted subcutaneously on the supports to allow the position of the valve element and the couplers to be changed after insertion. Electromagnetic switches may be used to activate motors which increase the tension in the wires within the wall of the support to alter the shape/position of the distal end of the anchor/support.

What is claimed:

1. A method of repairing a native heart valve of a heart, the method comprising:

intravascularly delivering a prosthetic device to the native heart valve, the prosthetic device comprising a frame having a support ring and a prosthetic valve having a plurality of prosthetic leaflets configured to open and close during a cardiac cycle, the support ring attached to a base of the plurality of prosthetic leaflets to define an opening of the prosthetic valve when the plurality of prosthetic leaflets open during the cardiac cycle, the plurality of prosthetic leaflets arranged to permit blood flow through the opening of the prosthetic valve when the plurality of prosthetic leaflets are open during the cardiac cycle;

transitioning the prosthetic device from a delivery state to a deployed state;

positioning the prosthetic device at a target position within the native heart valve via a support coupled to the prosthetic device; and locking the support catheter to suspend and maintain the prosthetic device within the native heart valve such that native leaflets of the native heart valve open during the cardiac cycle and close to co-apt against the prosthetic valve, wherein the support catheter remains in situ after delivery of the prosthetic device.

2. The method of claim 1, wherein intravascularly delivering the prosthetic device to the native heart valve comprises percutaneously introducing the prosthetic device in a delivery catheter via a blood vessel coupled to the heart and moving the prosthetic device until the prosthetic device is positioned across the native heart valve.

3. The method of claim 1, wherein intravascularly delivering the prosthetic device to the native heart valve comprises intravascularly delivering the prosthetic device to a tricuspid valve of the heart.

4. The method of claim 1, further comprising permitting blood to flow through the prosthetic valve when the plurality of prosthetic leaflets are open during the cardiac cycle.

5. The method of claim 1, wherein transitioning the prosthetic device from the delivery state to the deployed state comprises transitioning the support ring from a compressed delivery state to an expanded deployed state.

6. The method of claim 1, wherein the prosthetic device co-apts with native leaflets of the native heart valve when the native leaflets close to reduce regurgitation.

7. The method of claim 1, wherein positioning the prosthetic device at the target position comprises positioning the prosthetic device at the target position to, in a first cardiac state, form a gap between the prosthetic device and the native heart valve and to, in a second cardiac state, co-apt with the native heart valve.

8. The method of claim 1, wherein the prosthetic device comprises a cover coupled to the frame, and wherein transitioning the prosthetic device from the delivery state to the deployed state comprises transitioning the frame from a compressed delivery state to an expanded deployed state.

9. The method of claim 1, wherein positioning the prosthetic device at the target position within the native heart valve comprises deflecting the support catheter.

10. The method of claim 9, wherein locking the support catheter comprises locking a shape of the deflected support catheter.

11. The method of claim 1, wherein positioning the prosthetic device at the target position within the native heart valve comprises extending the prosthetic device from a blood vessel coupled to the heart to the target position within the native heart valve via the support catheter.

12. The method of claim 1, wherein locking the support catheter comprises locking the support catheter to suspend and maintain the prosthetic device within the native heart valve without anchoring to either an atrial or ventricular wall of the heart.

13. The method of claim 1, wherein positioning the prosthetic device at the target position within the native heart valve comprises actuating one or more actuators to control axial positioning of the prosthetic device.

14. The method of claim 1, wherein the support catheter further comprises at least one of a stylet, a shaped collar, or a stiff collar configured to provide a shape for implantation.

15. The method of claim 1, wherein the support catheter comprises a stiffness sufficient to hold a shape for implantation.

16. The method of claim 1, wherein the support catheter comprises an outer support sheath and an inner support tube, and wherein positioning the prosthetic device at the target position within the native heart valve comprises rotating the inner support tube within the outer support sheath.

17. The method of claim 16, wherein locking the support catheter comprises locking the inner support tube to the outer support sheath.

* * * * *